(12) United States Patent
Yeh

(10) Patent No.: US 11,015,213 B2
(45) Date of Patent: May 25, 2021

(54) METHOD OF PREPARING CELL FREE NUCLEIC ACID MOLECULES BY IN SITU AMPLIFICATION

(71) Applicant: CIRCULOGENE THERANOSTICS, LLC, Birmingham, AL (US)

(72) Inventor: Chen-Hsiung Yeh, Birmingham, AL (US)

(73) Assignee: CIRCULOGENE THERANOSTICS, LLC, Homewood, AL (US)

( * ) Notice: Subject to any disclaimer, the term of this patent is extended or adjusted under 35 U.S.C. 154(b) by 284 days.

(21) Appl. No.: 15/752,178

(22) PCT Filed: Aug. 12, 2016

(86) PCT No.: PCT/US2016/046875
§ 371 (c)(1),
(2) Date: Feb. 12, 2018

(87) PCT Pub. No.: WO2017/027835
PCT Pub. Date: Feb. 16, 2017

(65) Prior Publication Data
US 2019/0024127 A1   Jan. 24, 2019

Related U.S. Application Data

(60) Provisional application No. 62/204,268, filed on Aug. 12, 2015.

(51) Int. Cl.
| | | |
|---|---|---|
| *C12Q 1/68* | (2018.01) | |
| *C12P 19/34* | (2006.01) | |
| *C40B 40/06* | (2006.01) | |
| *C40B 50/06* | (2006.01) | |
| *C12Q 1/6844* | (2018.01) | |
| *C12Q 1/6806* | (2018.01) | |

(52) U.S. Cl.
CPC ........... *C12P 19/34* (2013.01); *C12Q 1/6806* (2013.01); *C12Q 1/6844* (2013.01); *C40B 40/06* (2013.01); *C40B 50/06* (2013.01); *C12Q 2521/101* (2013.01); *C12Q 2521/131* (2013.01); *C12Q 2521/307* (2013.01); *C12Q 2521/319* (2013.01); *C12Q 2521/501* (2013.01); *C12Q 2521/531* (2013.01); *C12Q 2525/155* (2013.01); *C12Q 2543/101* (2013.01); *C12Y 207/01078* (2013.01); *C12Y 207/07007* (2013.01); *C12Y 207/07049* (2013.01); *C12Y 302/02027* (2013.01); *C12Y 605/01001* (2013.01)

(58) Field of Classification Search
CPC ................ C12Q 1/6806; C12Q 1/6844; C12Q 2525/155
See application file for complete search history.

(56) References Cited

U.S. PATENT DOCUMENTS

| | | |
|---|---|---|
| 2002/0055148 A1 | 5/2002 | Hong |
| 2002/0169104 A1 | 5/2002 | Frank et al. |
| 2007/0083334 A1 | 4/2007 | Mintz et al. |
| 2010/0009364 A1 | 1/2010 | Fantl et al. |
| 2012/0316074 A1 | 12/2012 | Saxonov et al. |
| 2015/0079637 A1* | 3/2015 | Makarov ............ C12P 19/34 435/91.21 |
| 2016/0265064 A1* | 9/2016 | Das ................. C12Q 1/6827 |

FOREIGN PATENT DOCUMENTS

| | | | |
|---|---|---|---|
| EP | 2770090 | 8/2014 | |
| WO | WO-9611271 A1 * | 4/1996 | ......... C07K 14/4359 |
| WO | WO-2015013465 A2 * | 1/2015 | ............. C12Q 1/689 |

OTHER PUBLICATIONS

Lowe et al. (Nucleic Acids Research, 1990, 18(7):1757-1761) (Year: 1990).*
Miura et al. (J Hum Genet, 2006, 51:412-417) (Year: 2006).*
Copenheaver, Blaine R. "International Search Report and Written Opinion—PCT/US2016/046875" USPTO as ISA; dated Oct. 13, 2016; pp. 1-18.

* cited by examiner

*Primary Examiner* — Stephanie K Mummert
(74) *Attorney, Agent, or Firm* — Maynard Cooper & Gale, P.C.

(57) ABSTRACT

Methods for in situ amplification (ISA) of cfNA, such as cfDNA, in a sample are provided wherein the cfNA in the sample is not subject to a nucleic acid purification step. The methods disclosed may be used to generate an analyzable pool of cfNA present in the sample. The analyzable pool may be used with a variety of analytical techniques to characterize the nucleic acid in the sample. Methods of diagnosis, determining a therapeutic intervention and monitoring of a subject are also provided.

35 Claims, 10 Drawing Sheets
Specification includes a Sequence Listing.

METHOD OF PREPARING CELL FREE NUCLEIC ACID MOLECULES BY IN SITU AMPLIFICATION

CROSS-REFERENCE TO RELATED APPLICATIONS

This application is a national stage under 35 U.S.C. 371 of International Application No. PCT/US2016/046875 having an international filing date of Aug. 12, 2016 (currently published). International Application No. PCT/US2016/046875 cites the priority of U.S. provisional patent application No. 62/204,268, filed Aug. 12, 2015.

BACKGROUND

It is estimated that 1.6 million new cases of cancer will be diagnosed this year, leading to over a half a million death from cancer. This translates to about 1,600 people per day, accounting for 1 out of 4 deaths in the US. Major advances in genetic testing of solid tumor biopsies have changed how cancers are targeted and treated leading to improved survival rates.

Currently, tissue biopsy, generally from the primary tumor, is used to determine the molecular profile of a cancer at a single time point, before targeted therapy commences. However, solid tumor sampling suffers from several drawbacks and limitations. First, solid tumor sampling is an invasive procedure and presents a risk to the patient in many instances. Second, in some cases solid tumor sampling is either not an option or is impractical due to the location and/or size of the tumor. Third, tumor heterogeneity may not be adequately addressed as solid tumor sampling is limited both spatially to the region biopsied, and temporally to the state of tumor at the time of biopsy. Tumor genomes are remarkably unstable and prone to clonal expansion under selection pressure. Therefore, the genomic signature of the cancer changes both spatially and temporally and is not static in nature. Fourth, the identification of relevant information from solid tumor sampling for making treatment decisions can take from days to weeks or even months, complicating the use of the information for therapeutic applications. Fifth, solid tumor sampling is costly to undertake, thereby limiting its application in many cases. Finally, solid tumor sampling is not practical for longitudinal monitoring of cancer therapy due to a number of factors such as time needed for the analysis, cost of the analysis and the invasive nature of obtaining a sample for analysis. Therefore, genomic characterization of tumor tissue remains a major challenge in the treatment and management of cancers.

Blood biopsy (also referred to as liquid biopsy), particularly of circulating cell-free DNA (cfDNA), is emerging as a non-invasive method for identification of specific genetic alterations present in a tumor. Such methods are being studied to identify those mutations that are treatable by known cancer therapies and to develop targeted therapy for treatment. Advanced technology to isolate, quantify, and analyze cfDNA in the blood has led to the identification of cancer-specific aberrations in the circulation such as chromosomal abnormalities, gene mutations, differences in methylation patterns and copy number variations. These aberrations were found to mirror those from solid tumor tissues.

Blood biopsies utilizing cfDNA analysis offer a solution to the drawbacks encountered with solid tumor sampling. Blood biopsies are minimally invasive allowing routine collection of samples for analysis during routine office visits. In addition, blood biopsies allow a sampling of a wide range of tumor DNA and overcome the lack of heterogeneity seen in solid tumor sampling. Blood biopsies also provide for a rapid return of diagnostic information to the healthcare provider. Finally, blood biopsies, due to their minimally invasive nature and rapid results, are ideal for longitudinal monitoring of tumor genomic evolution in real time in the most cost-effective manner.

Circulating cfDNA-based testing offers clinicians the ability to ensure treatment efficacy, monitor drug resistance, metastasis and recurrence, and tailor individualized therapeutic interventions for patients in real time. The use of tumor genome sequencing of circulating cfDNA to guide treatment decisions would greatly improve clinical outcomes. As such the clinical utility of cfDNA in the personalized management of cancer diagnosis and therapy has the ability to significantly alter current treatment models, increase overall cancer survival rates and become the standard-of-care for a new-generation of cancer management.

However, the analysis of cfDNA also suffers several drawbacks. Such limitations include, but are not limited to, the requirement of large sample volume, low yield of cfDNA, differential recovery of different size cfDNA fragments, and lack of reproducibility. The foregoing are major obstacles for the routine application of cfDNA-based testing in the clinic.

Currently, although a number of methods for extraction and isolation of cfDNA are employed, the efficiency and yield of cfDNA isolation is extremely low due to the incomplete extraction of cfDNA starting materials from the sample and large material loss during this process. Furthermore the quantification is variable because of lack of standardization.

The analysis of cfDNA and the use of cfDNA as a clinical tool is not optimal. The present disclosure offers a novel and inventive solution to the problems encountered in cfDNA analysis by providing a method for superior cfDNA enrichment from a sample. Such methods require a low input volume of sample and provide a high recovery of nucleic acid material for use in subsequent analysis. As such, the methods of the present disclosure allow for the enrichment of cfDNA directly from a sample. The disclosed methods enable multiple analyses with microliter volumes (blood-drop volumes) of sample on a broad range of genomic platforms, including, but not limited to, next-generation sequencing (NGS) and qPCR. The methods of the present disclosure enable clinicians to work with a sample volume as small as 10 microliters (via a finger-prick, for example). The methods of the present disclosure allow for a number of advantages, including, but not limited to, more complete characterization of the genetic alterations involved, expedited clinical decision-making, identification of targeted therapies and identification of experimental clinical trials for eligible patients in a manner that is both time-efficient and cost-efficient manner. Therefore, by utilizing the methods of the present disclosure the potential of cfDNA analysis may be fully realized.

Lanes 6-8 were frozen plasma samples from healthy subjects and lanes 9-10 were fresh plasma samples from healthy subject.

Figure 1A:
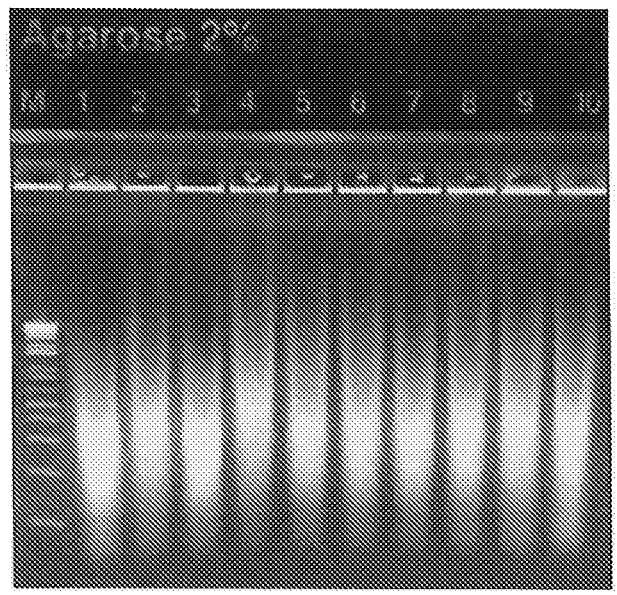
FIG. 1A shows agarose gel electrophoresis of cfDNA produced using the CGD method from 20 μL of plasma. cfDNA was visualized using ethidium bromide. Lanes 1-4 were frozen clinical plasma samples from subject diagnosed with or suspected of having cancer, lane 5 was fresh plasma from a healthy subject spiked with plasma from sample 4.
Figure 1B:
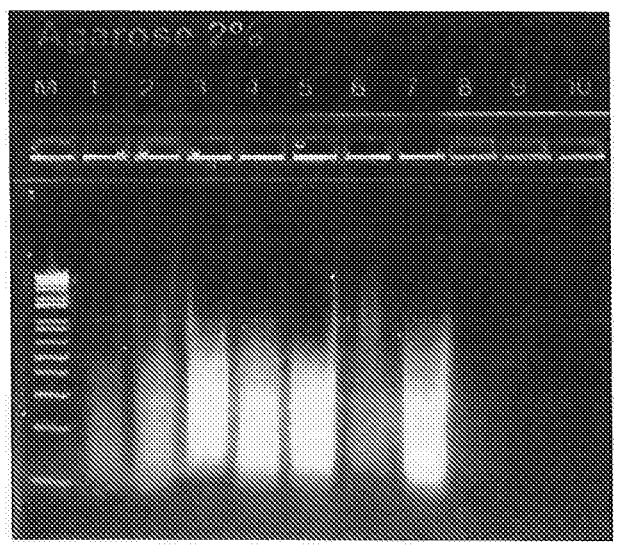

FIG. 1B shows agarose gel electrophoresis of cfDNA produced using the CGD method from 10 µL of urine. cfDNA was visualized using ethidium bromide. Lanes 1-6 were fresh urine samples from healthy subjects and lane 7 was a plasma sample for comparison.

Figure 2:
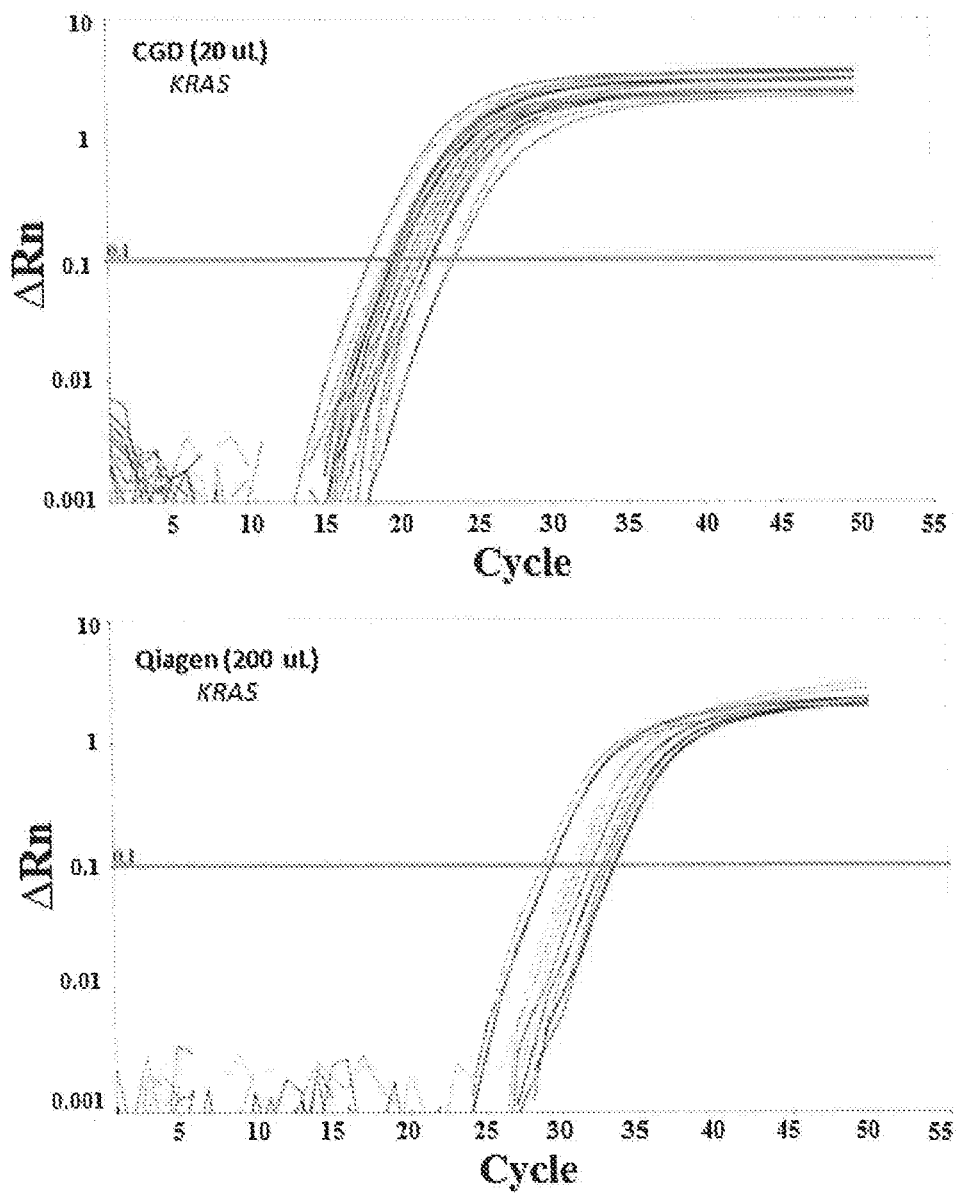

FIG. 2 shows amplification plots of KRAS generated using TaqMan quantitative real-time PCR on cfDNA prepared from 20 µL and 200 µL of plasma using the CGD method and QIAamp kit, respectively.

Figure 3A:
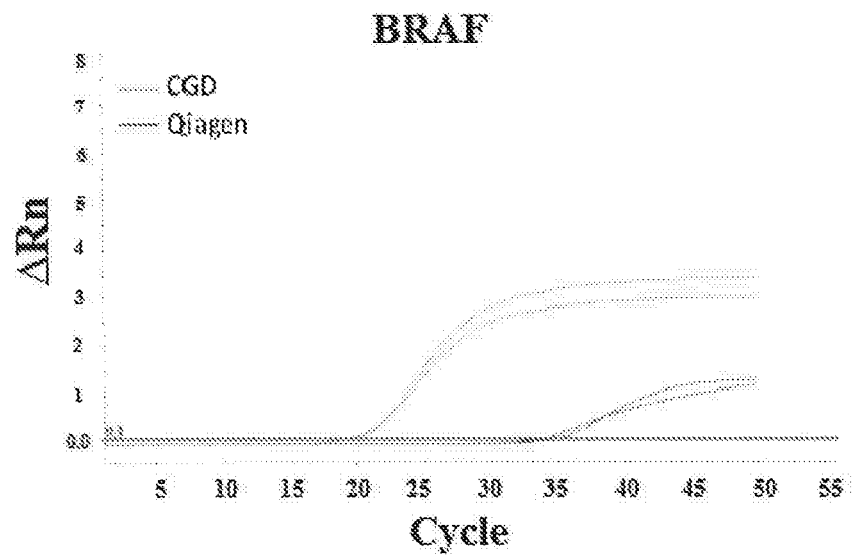

FIG. 3A shows amplification plots of BRAF generated using TaqMan quantitative real-time PCR on cfDNA prepared from 20 µL and 200 µL of plasma using the CGD method and QIAamp kit, respectively.

Figure 3B:
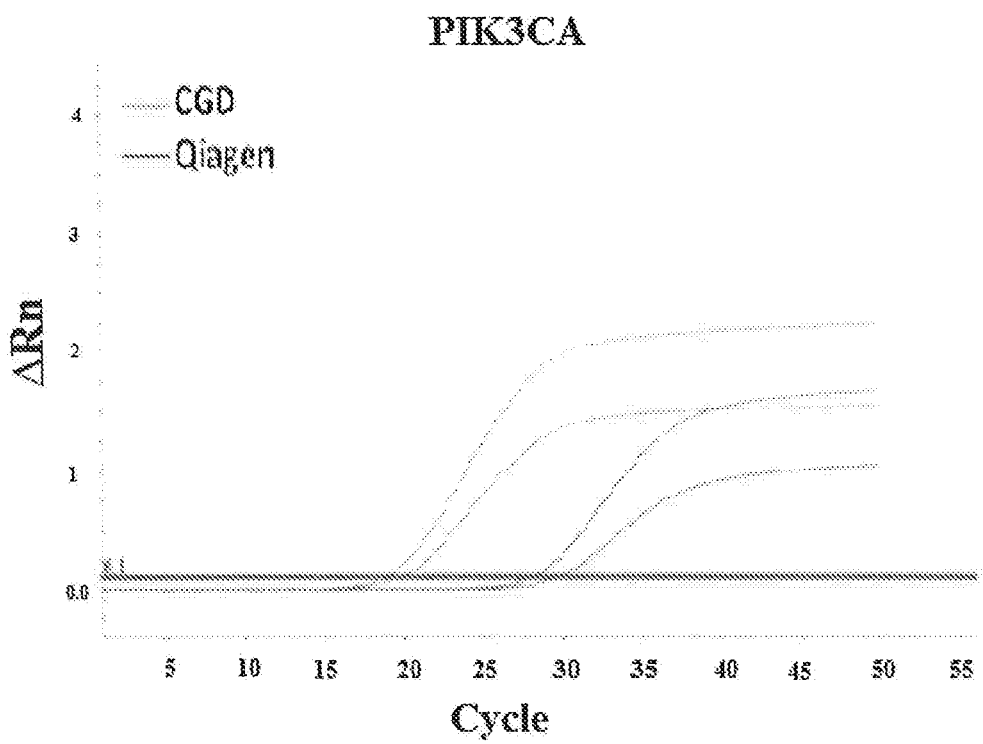

FIG. 3B shows amplification plots of PIK3CA generated using TaqMan quantitative real-time PCR on cfDNA prepared from 20 µL and 200 µL of plasma using the CGD method and QIAamp kit, respectively.

Figure 3C:
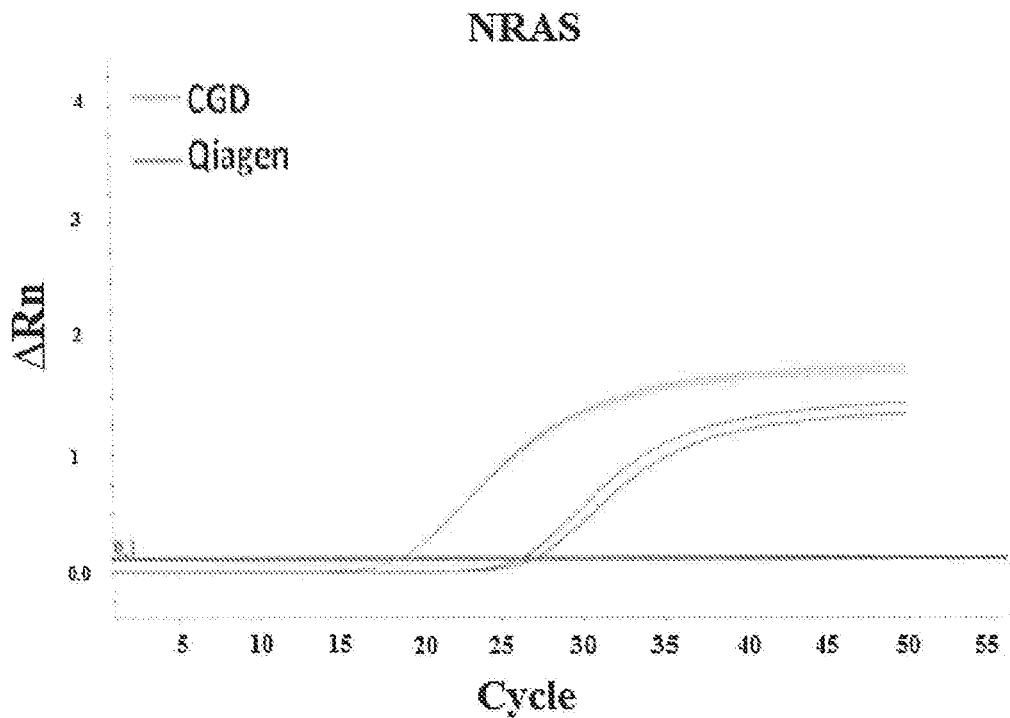

FIG. 3C shows amplification plots of NRAS generated using TaqMan quantitative real-time PCR on cfDNA prepared from 20 µL and 200 µL of plasma using the CGD method and QIAamp kit, respectively.

Figure 4:
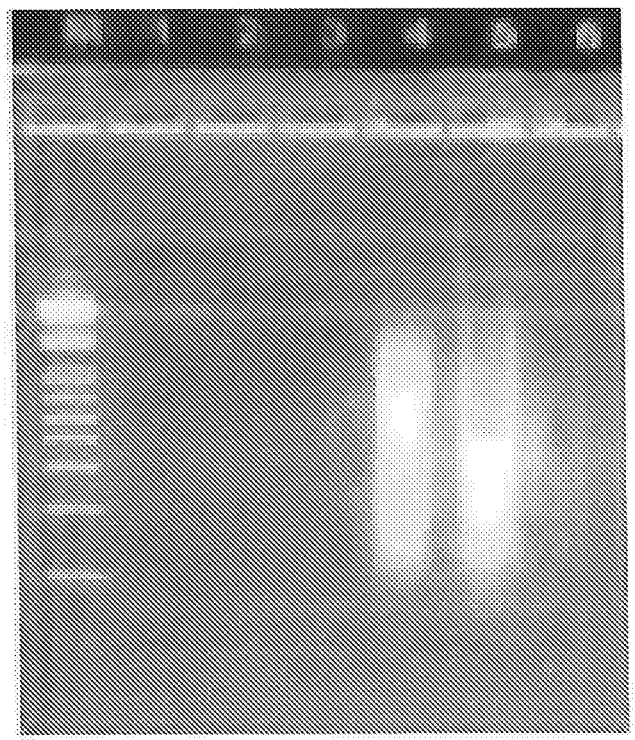

FIG. 4 shows agarose gel electrophoresis (2%) of cfDNA produced using the CGD method from 20 µL of saliva collected using a commercial saliva sampling kit with and without preservatives. cfDNA was visualized using ethidium bromide. Lanes 1 and 2 show the results from saliva samples obtained with a commercial sampling kit with preservatives with lane 3 being the a negative control (no saliva sample present), while lanes 4 and 5 show results from saliva samples obtained with a commercial sampling kit without preservatives with lane 6 being the a negative control (no saliva sample present).

Figure 5:
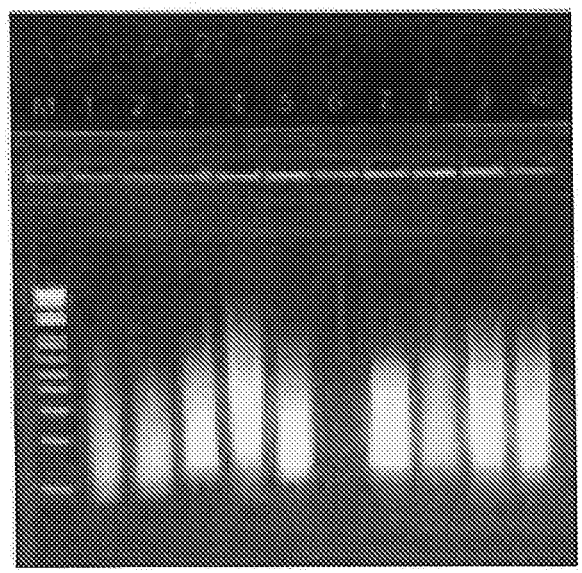

FIG. 5 shows agarose gel electrophoresis (2%) of cfDNA produced using the CGD method from 204 of plasma and cerebrospinal fluid and 10 µL of urine. cfDNA was visualized using ethidium bromide. Sample assignments are as follows (with cfDNA concentration in parens): lane 1 CSF (8.5), lane 2 urine (5.1), lane 3 plasma (22), lane 4 plasma (59), lanes 5 plasma (36.4), lane 6 negative control; lane 7 urine (52.2), lane 8 urine (11.2), lanes 9 urine (89.6) and lane 10 urine (30).

Figure 6:
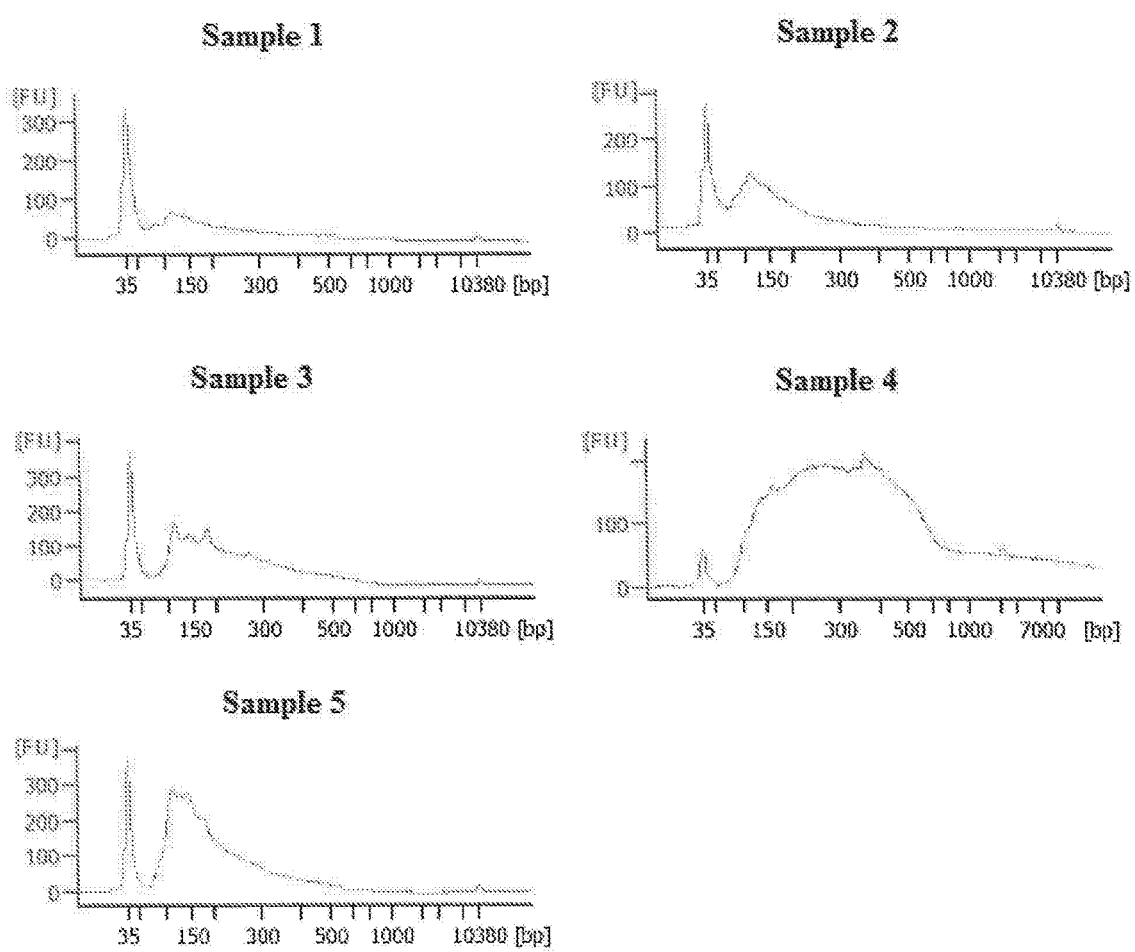

FIG. 6 shows analysis of samples 1 to 5 of FIG. 5 using the Agilent 2100 Bioanalyzer to determine the size distribution and quantitation of cfDNA prepare by the CGD method from plasma, CSF and urine samples.

Figure 7:
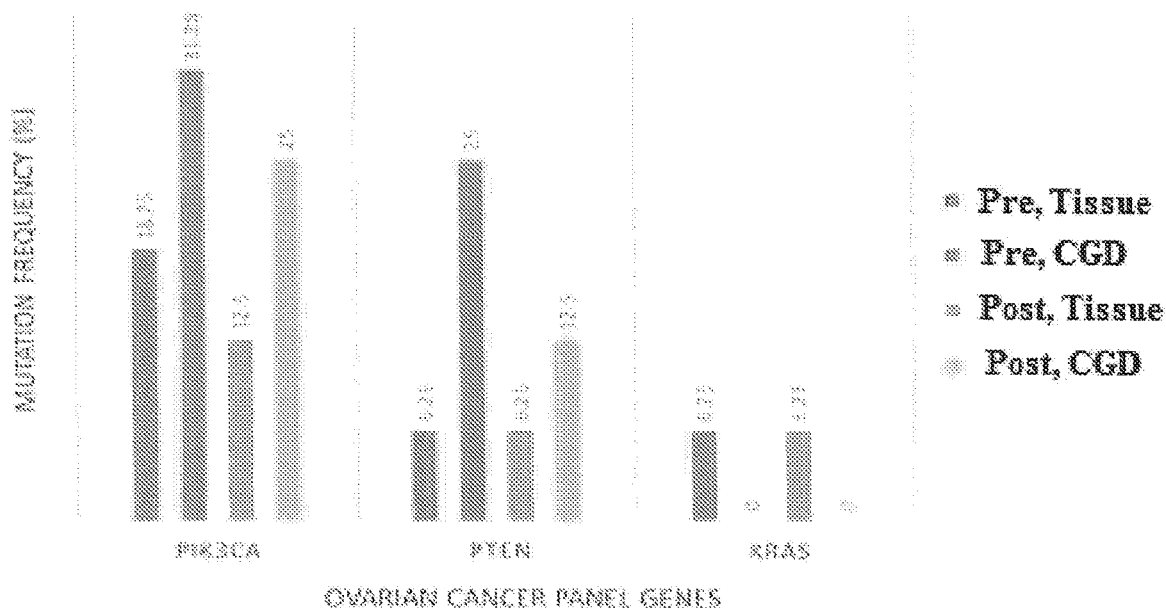

FIG. 7 shows a comparison between results obtained with the CGD method and tissue biopsy for ovarian cancer patients pre-treatment and post-treatment with respect to the PIK3 CA, PTEN and KRAS genes.

Figure 8A:
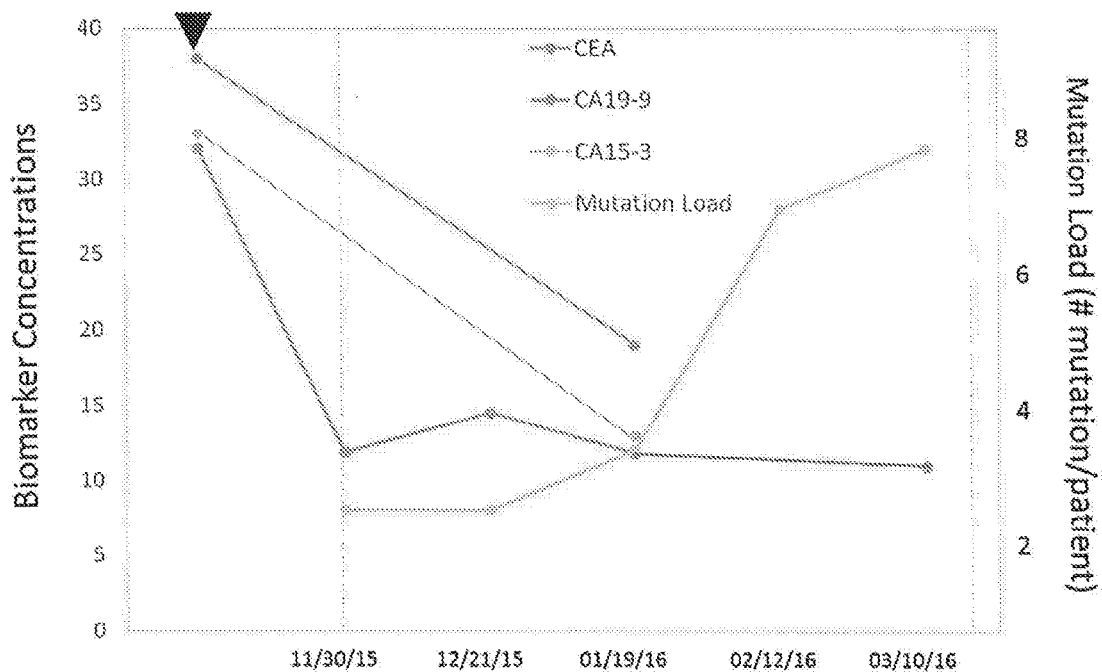

FIG. 8A shows determination of cfDNA mutations in a subject diagnosed with lung cancer. Lower mutation load in circulating cfDNA during therapy and elevated mutation load after stable disease for 50 days. Initiation of treatment is indicated by the black arrow black arrow. Mutation load is expressed as number of somatic mutation detected per patient (vertical scale on the right side of the graph). Dotted blue line indicates the time PET/CT was performed. Time points indicate the time cfDNA analysis was conducted.

Figure 8B:
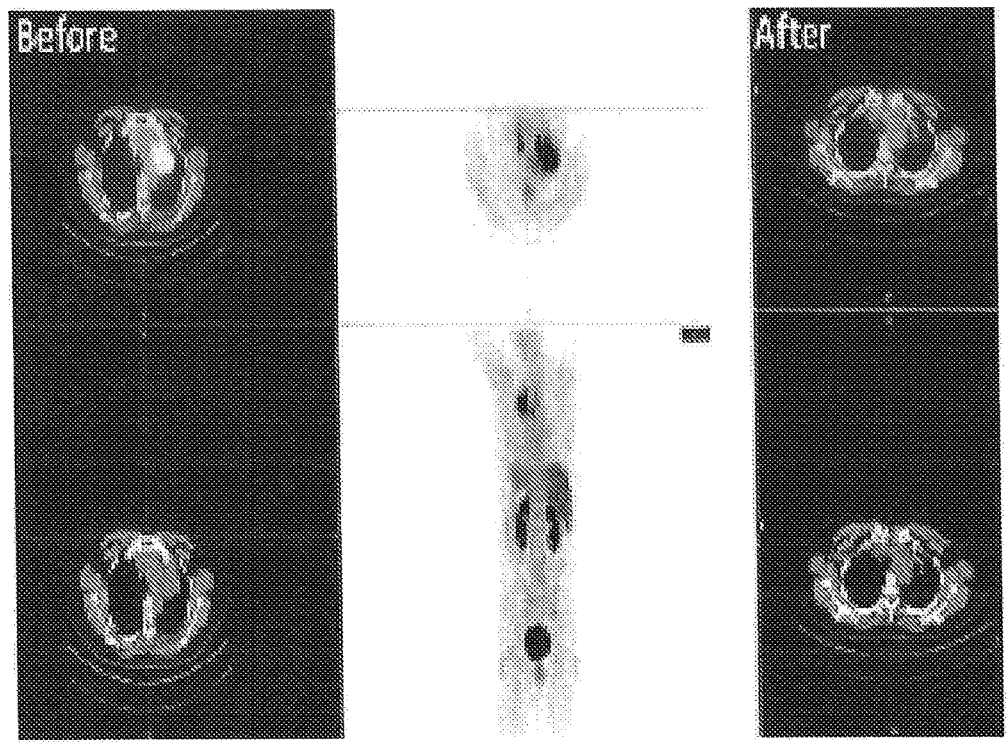

FIG. 8B shows PET/CT imaging of the subject, indicating stable disease on Nov. 30, 2015 and progressive disease in March 2016, confirming the results of cfDNA analysis in FIG. XA.

Figure 9A:
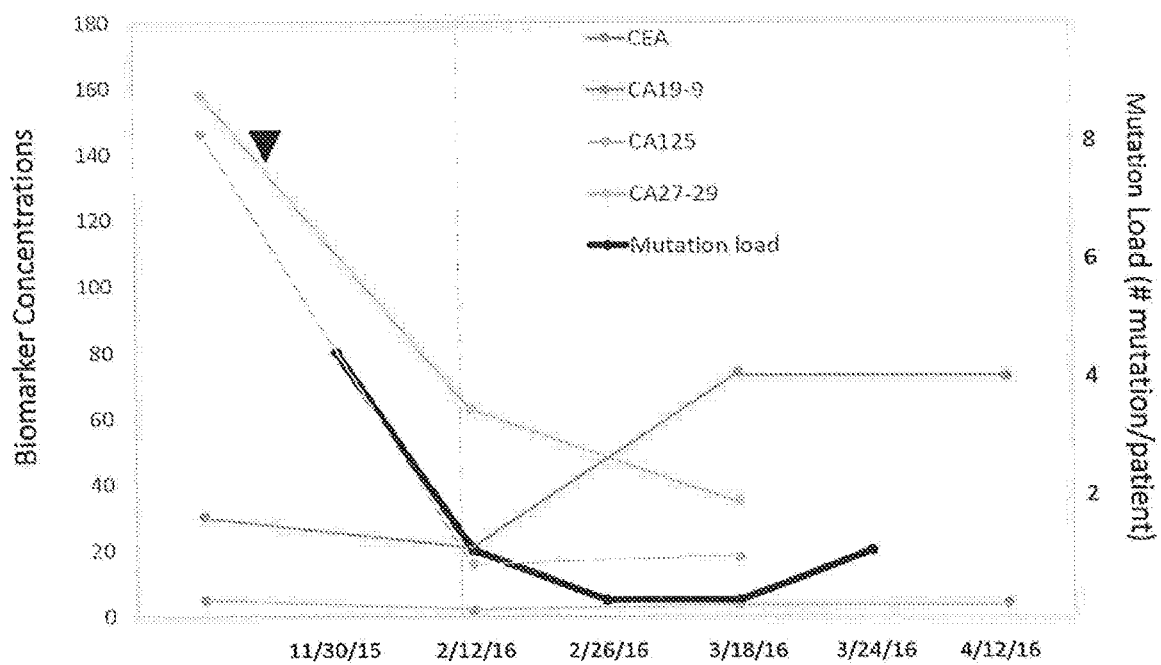

FIG. 9A shows determination of cfDNA mutations in a subject diagnosed with peri-pancreatic lymph node adenocarcinoma. Mutation load in circulating cfDNA was declined during therapy indicating stable disease. Stable disease was in agreement with protein biomarkers, PET/CT imaging (Right picture) and clinical outcomes. Mutation load is expressed as number of somatic mutation detected per patient (vertical scale on the right side of the graph). Dotted blue line indicates the time PET/CT was performed. Time points indicate the time cfDNA analysis was conducted.

Figure 9B:
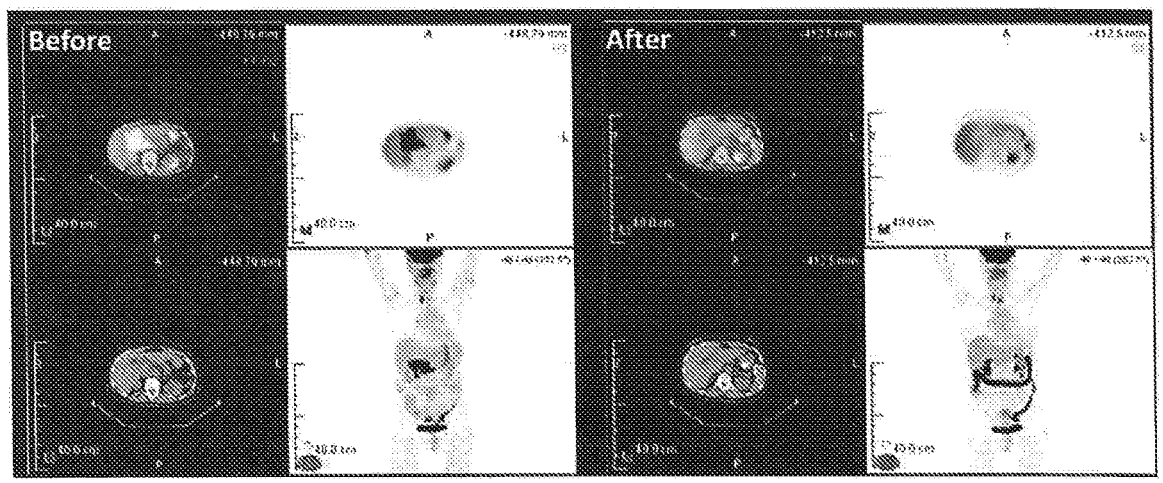

FIG. 9B shows PET/CT imaging of the subject, indicating stable disease after therapy confirming the results of cfDNA analysis in FIG. XA.

Figure 10:
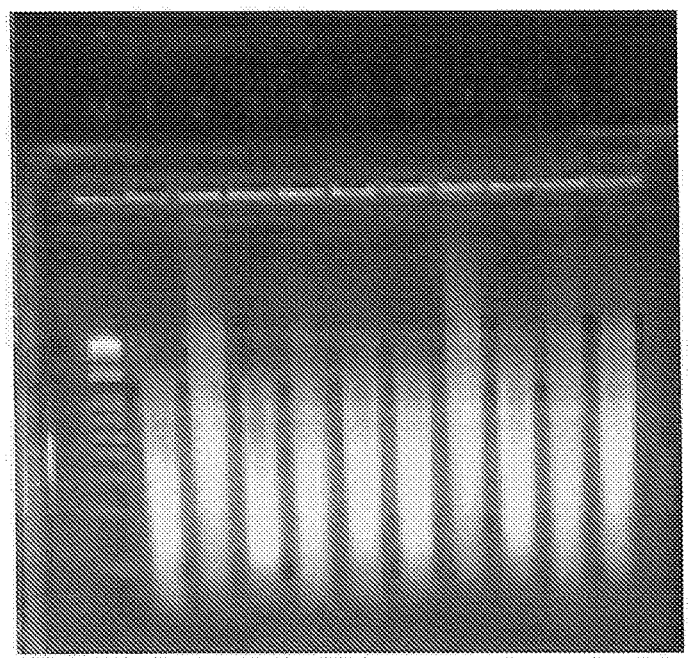

FIG. 10 shows analyzable cfDNA pools prepare by the CGD method using reagents stored at −20° C. (lanes 1-5) and 4° C. (lanes 6-10) subjected to agarose gel electrophoresis on a 2% gel and visualized using ethidium bromide (molecular weight ladder 1 kb).

Figure 11:
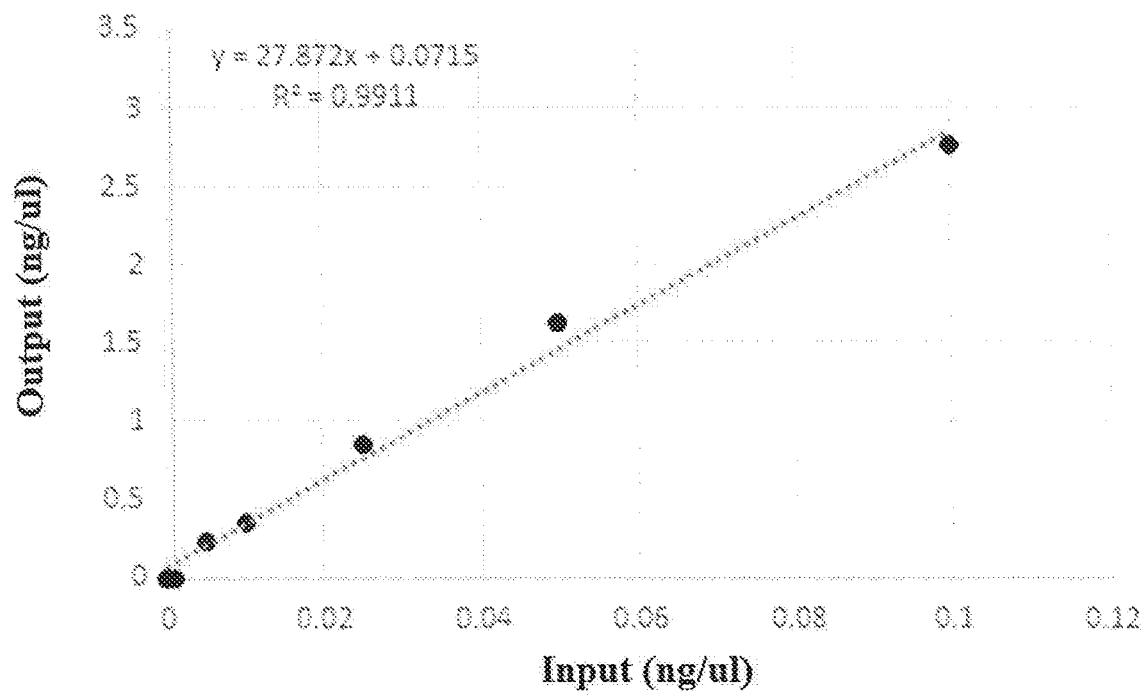

FIG. 11 shows a standard curve produced using the CGD method using purified DNA at concentrations of 0, 0.001, 0.005, 0.01, 0.025, 0.05, 0.1, 0.25, 0.5, and 1 ng/µL.

Figure 12:
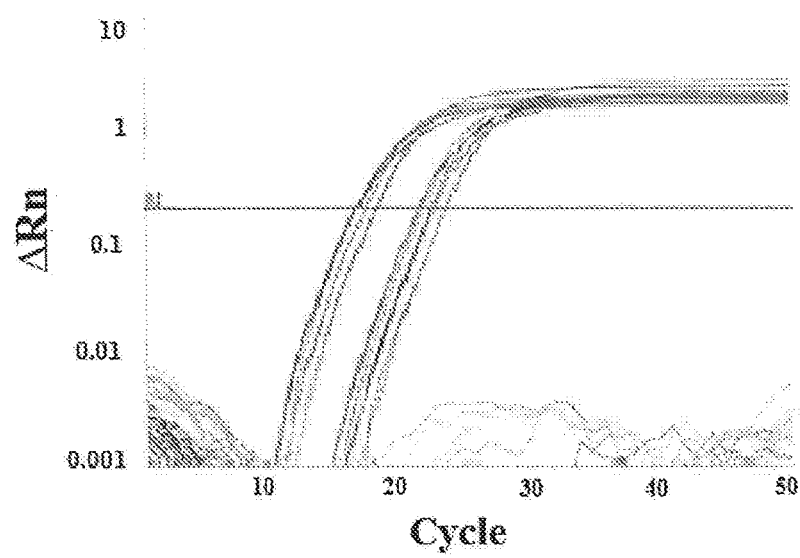

FIG. 12 shows an amplification plot of cDNA generated from cfRNA from 20 µL of plasma using the CGD method.

SUMMARY OF THE DISCLOSURE

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

In a first aspect, the present disclosure provides a method of in situ amplification (ISA) of a cell-free nucleic acid (cfNA) in a sample without subjecting the cfNA in the sample to a nucleic acid purification step, the method comprising the steps of: i) providing a liquid sample containing a plurality of cfNA molecules; ii) performing at least one processing step on the sample; iii) converting at least a portion of the cfNA molecules in the sample to modified cfNA to create an amplifiable cfNA pool; and iv) amplifying the amplifiable cfNA pool to produce an analyzable pool of cfNA molecules.

In a second aspect, the present disclosure provides a method of ISA of a cfNA in a sample without subjecting the cfNA in the sample to a nucleic acid purification step, the method comprising the steps of: i) providing a liquid sample containing a plurality of cfNA molecules; ii) performing at least one processing step on the sample; iii) converting at least a portion of the cfNA molecules in the sample to modified cfNA by adding an exogenous nucleic acid sequence to the 3' end of at least a portion of the cfNA molecules in the sample to create an amplifiable cfNA pool; and v) amplifying the amplifiable cfNA pool to produce an analyzable pool of cfNA molecules.

In a third aspect, the present disclosure provides a method of ISA of a cfNA in a sample without subjecting the cfNA in the sample to a nucleic acid purification step, the method comprising the steps of: i) providing a liquid sample containing a plurality of cfNA molecules; ii) performing at least one processing step on the sample; iii) converting at least a portion of the cfNA molecules in the sample to modified cfNA by adding an exogenous nucleic acid sequence to the 5' end of at least a portion of the cfNA molecules in the sample to create an amplifiable cfNA pool; and v) amplifying the amplifiable cfNA pool to produce an analyzable pool of cfNA molecules.

In a fourth aspect, the present disclosure provides a method of ISA of a cfNA in a sample without subjecting the cfNA in the sample to a nucleic acid purification step, the method comprising the steps of: i) providing a liquid sample containing a plurality of cfNA molecules; ii) performing at least one processing step on the sample; iii) converting at least a portion of the cfNA molecules in the sample to modified cfNA by adding an exogenous nucleic acid sequence to both the 3' and 5' end of at least a portion of the cfNA molecules in the sample to create an amplifiable cfNA pool; and v) amplifying the amplifiable cfNA pool to produce an analyzable pool of cfNA molecules.

In a fifth aspect, the present disclosure provides a method of ISA of a cfDNA in a sample without subjecting the sample to a nucleic acid purification step, the method comprising the steps of: i) providing a liquid sample containing a plurality of cfDNA molecules; ii) performing at least one processing step on the sample; iii) converting at least a portion of the cfDNA molecules in the sample to modified cfDNA to create an amplifiable cfDNA pool; and iv) amplifying the amplifiable cfDNA pool to produce an analyzable pool of cfDNA molecules.

In a sixth aspect, the present disclosure provides a method of ISA of a cfDNA in a sample without subjecting the sample to a nucleic acid purification step, the method comprising the steps of: i) providing a liquid sample containing a plurality of cfDNA molecules; ii) performing at least one processing step on the sample; iii) converting at least a portion of the cfDNA molecules in the sample to modified cfDNA by adding an exogenous nucleic acid sequence to the 3' end of at least a portion of the cfDNA molecules in the sample to create an amplifiable cfDNA pool; and v) amplifying the amplifiable cfDNA pool to produce an analyzable pool of cfDNA molecules.

In a seventh aspect, the present disclosure provides a method of ISA of a cfDNA in a sample without subjecting the sample to a nucleic acid purification step, the method comprising the steps of: i) providing a liquid sample containing a plurality of cfDNA molecules; ii) performing at least one processing step on the sample; iii) converting at least a portion of the cfDNA molecules in the sample to modified cfDNA by adding an exogenous nucleic acid sequence to the 5' end of at least a portion of the cfDNA molecules in the sample to create an amplifiable cfDNA pool; and v) amplifying the amplifiable cfDNA pool to produce an analyzable pool of cfDNA molecules.

In an eighth aspect, the present disclosure provides a method of ISA of a cfDNA in a sample without subjecting the sample to a nucleic acid purification step, the method comprising the steps of: i) providing a liquid sample containing a plurality of cfDNA molecules; ii) performing at least one processing step on the sample; iii) converting at least a portion of the cfDNA molecules in the sample to modified cfDNA by adding an exogenous nucleic acid sequence to both the 3' and 5' ends of at least a portion of the cfDNA molecules in the sample to create an amplifiable cfDNA pool; and v) amplifying the amplifiable cfDNA pool to produce an analyzable pool of cfDNA molecules.

In a ninth aspect, the present disclosure provides a method of ISA of a cfRNA in a sample without subjecting the sample to a nucleic acid purification step, the method comprising the steps of: i) providing a liquid sample containing a plurality of cfRNA molecules; ii) performing at least one processing step on the sample; iii) converting at least a portion of the cfRNA molecules in the sample to modified cfRNA to create an amplifiable cfRNA pool; and iv) amplifying the amplifiable cfRNA pool to produce an analyzable pool of cfRNA molecules.

In a tenth aspect, the present disclosure provides a method of ISA of a cfRNA in a sample without subjecting the sample to a nucleic acid purification step, the method comprising the steps of: i) providing a liquid sample containing a plurality of cfRNA molecules; ii) performing at least one processing step on the sample; iii) converting at least a portion of the cfRNA molecules in the sample to modified cfRNA by adding an exogenous nucleic acid sequence to the 3' end of at least a portion of the cfRNA molecules in the sample to create an amplifiable cfRNA pool; and v) amplifying the amplifiable cfRNA pool to produce an analyzable pool of cfRNA molecules.

In an eleventh aspect, the present disclosure provides a method of ISA of a cfRNA in a sample without subjecting the sample to a nucleic acid purification step, the method comprising the steps of: i) providing a liquid sample containing a plurality of cfRNA molecules; ii) performing at least one processing step on the sample; iii) converting at least a portion of the cfRNA molecules in the sample to modified cfRNA by adding an exogenous nucleic acid sequence to the 5' end of at least a portion of the cfRNA molecules in the sample to create an amplifiable cfRNA pool; and v) amplifying the amplifiable cfRNA pool to produce an analyzable pool of cfRNA molecules.

In a twelfth aspect, the present disclosure provides a method of ISA of a cfRNA in a sample without subjecting the sample to a nucleic acid purification step, the method comprising the steps of: i) providing a liquid sample containing a plurality of cfRNA molecules; ii) performing at least one processing step on the sample; iii) converting at least a portion of the cfRNA molecules in the sample to modified cfRNA by adding an exogenous nucleic acid sequence to both the 3' and 5' ends of at least a portion of the cfRNA molecules in the sample to create an amplifiable cfRNA pool; and v) amplifying the amplifiable cfRNA pool to produce an analyzable pool of cfRNA molecules.

In certain embodiments of each of the first through twelfth aspects described above, the liquid sample is any liquid sample obtained from the subject. In certain embodiments, the liquid sample is a blood sample, a serum sample, a plasma sample, a saliva sample, cerebrospinal fluid sample or a urine sample. In certain embodiments, the liquid sample is processed. For example, a blood sample may be processed to produce a plasma or serum sample.

In certain embodiments of each of the first through twelfth aspects described above, the sample volume may be less than about 1 ml, less than about 0.5 ml, less than about 0.1 ml, less than about 0.05 ml or less than about 0.025 ml (but in all cases greater than 0.010 ml). In certain embodiments, the sample volume is from about 10 to about 150 microliters. In certain embodiments, the sample volume is from about 10 to about 100 microliters. In certain embodiments, the sample volume is from about 10 to about 75 microliters. In certain embodiments, the sample volume is from about 10 to about 50 microliters. In certain embodiments, the sample volume is from about 10 to about 25 microliters.

In certain embodiments of each of the first through twelfth aspects described above, the sample volume in the ranges described herein may be directly obtained from a subject (i.e., a sample of 25 microliters of blood may be obtained from a subject through a finger stick). In each of the first through fourth aspects described above, the sample volume in the ranges described herein may be obtained from a larger volume of a sample obtained from a subject (i.e., a sample of 5 mls of blood may be obtained from a subject and a 50 microliter sample may be taken from the 5 ml sample and of used as the sample volume).

In certain embodiments of each of the first through twelfth aspects described above, the exogenous nucleic acid sequence added to the 3' end, 5' end or both the 3' end and 5' ends of the cfNA, cfDNA and/or cfRNA is a double-stranded nucleic acid sequence. In certain embodiments of each of the first through twelfth aspects described above, the exogenous nucleic acid sequence added to the 3' end, 5' end or both the 3' end and 5' ends of the cfNA, cfDNA and/or cfRNA is a single-stranded nucleic acid sequence containing a palindromic sequence. In certain embodiments of the foregoing, the cfNA, cfDNA and/or cfRNA is double-stranded.

In certain embodiments of each of the first through fourth aspects described above, the cfNA may be any nucleic acid. In certain embodiments, the cfNA is cfDNA. In certain embodiments, the cfNA is double-stranded cfDNA. In certain embodiments, the cfNA is single-stranded cfDNA. In certain embodiments, the cfNA is cell free-RNA (cfRNA). In certain embodiments, the cfNA is double-stranded cfRNA. In certain embodiments, the cfNA is single-stranded cfRNA.

In certain embodiments of the first through twelfth aspects, the sample may contain both cfDNA and cfRNA and each of the cfDNA and cfRNA are amplified to produce an analyzable pool of both cfDNA and cfRNA molecules. In certain embodiments of the first through twelfth aspects, the sample may contain both cfDNA and cfRNA and only the cfDNA is amplified to produce an analyzable pool of cfDNA molecules. In certain embodiments of the first through twelfth aspects, the sample may contain both cfDNA and cfRNA and only the cfRNA is amplified to produce an analyzable pool of cfRNA molecules. In the foregoing the cfDNA may be double-stranded and/or the cfRNA may be double-stranded.

In certain embodiments of each of the first through twelfth aspects described above, the processing step may be dilution, the addition of a buffer or buffer system, heating the sample, fragmenting at least a portion of the cfNA in the sample (including cfDNA and/or cfRNA), or a combination of the foregoing.

In certain embodiments of each of the first through twelfth aspects described above, the converting at least a portion of the cfNA molecules in the sample to modified cfNA to create an amplifiable cfNA pool step involves end repair of at least a portion of the cfNA (including cfDNA and/or cfRNA) in the sample, converting at least a portion of the cfNA (including cfDNA and/or cfRNA) in the sample to blunt end cfNA, A-tailing of at least a portion of the cfNA (including cfDNA and/or cfRNA) in the sample, ligation, or a combination of the foregoing.

In certain embodiments of each of the first through twelfth aspects described above, the converting at least a portion of the cfNA molecules in the sample to modified cfNA to create an amplifiable cfNA pool step involves the use of an enzyme mixture comprising:
i) a polymerase having a 5'-3' polymerase activity with or without a 3'-5' exonuclease activity and ii) a ligase;
i) a polymerase having a 5'-3' polymerase activity with or without a 3'-5' exonuclease activity, ii) a ligase and iii) a polynucleotide kinase;
i) a polymerase having a 5'-3' polymerase activity with or without a 3'-5' exonuclease activity, ii) a ligase, iii) a polynucleotide kinase and iv) a replication block activating activity;
i) a polymerase having a 5'-3' polymerase activity with or without a 3'-5' exonuclease activity, ii) a ligase, iii) a polynucleotide kinase, iv) a replication block activating activity and v) a nucleic acid nicking enzyme activity;
i) a polymerase having a 5'-3' polymerase activity with or without a 3'-5' exonuclease activity, ii) a ligase, iii) a polynucleotide kinase, iv) a replication block activating activity, v) a nucleic acid nicking enzyme activity and vi) a nucleic acid binding protein.

In certain embodiments of each of the fifth through eighth aspects described above, the cfDNA may be double-stranded cfDNA or single-stranded cfDNA. In certain embodiments of the fifth through eighth aspects, the cfDNA is double-stranded cfDNA. In certain embodiments of the fifth through eighth aspects described above, the sample may further contain cfRNA (either single-stranded or double-stranded). In certain embodiments of the fifth through eighth aspects, the sample may contain both cfDNA and cfRNA and only the cfDNA is amplified to produce an analyzable pool of cfDNA molecules. In certain embodiments of the fifth through eighth aspects, the sample may contain both cfDNA and cfRNA and each of the cfDNA and the cfRNA is amplified to produce an analyzable pool of cfDNA and cfRNA molecules.

In certain embodiments of each of the ninth through twelfth aspects described above, the cfRNA may be double-stranded cfRNA or single-stranded cfRNA. In certain embodiments of the ninth through twelfth aspects, the cfRNA is double-stranded cfRNA. In certain embodiments of the ninth through twelfth aspects described above, the sample may further contain cfDNA (either single-stranded or double-stranded). In certain embodiments of the ninth through twelfth aspects, the sample may contain both cfRNA and cfDNA and only the cfRNA is amplified to produce an analyzable pool of cfRNA molecules. In certain embodiments of the ninth through twelfth aspects, the sample may contain both cfRNA and cfDNA and each of the cfRNA and the cfDNA is amplified to produce an analyzable pool of cfRNA and cfDNA molecules.

In certain embodiments of each of the first through twelfth aspects described above, at least 50% or more, 60% or more, 70% or more, 80% or more, 90% or more or 95% or more of the cfNA present in the sample are converted to modified cfNA to create the amplifiable cfNA pool. When the cfNA is cfDNA (including double-stranded cfDNA) such as in the fifth through eighth aspects, at least 50% or more, 60% or more, 70% or more, 80% or more, 90% or more or 95% or more of the cfDNA present in the sample are converted to modified cfDNA to create the amplifiable cfDNA pool. When the cfNA is cfRNA (including double-stranded cfRNA) such as in the ninth to twelfth aspects, at least 50% or more, 60% or more, 70% or more, 80% or more, 90% or more or 95% or more of the cfRNA present in the sample are converted to modified cfRNA to create the amplifiable cfRNA pool.

In a thirteenth aspect, the present disclosure provides a method of preparing a cfNA in a sample for analysis without subjecting the cfNA in the sample to a nucleic acid purification step, the method comprising the steps of: i) providing a liquid sample containing a plurality of cfNA molecules; ii) performing at least one processing step on the sample; and iii) converting at least a portion of the cfNA molecules in the sample to modified cfNA to create an amplifiable cfNA pool.

In a fourteenth aspect, the present disclosure provides a method of preparing a cfNA in a sample for analysis without subjecting the cfNA in the sample to a nucleic acid purification step, the method comprising the steps of: i) providing a liquid sample containing a plurality of cfNA molecules; ii) performing at least one processing step on the sample; and iii) converting at least a portion of the cfNA molecules in the sample to modified cfNA by adding an exogenous nucleic acid sequence to the 3' end of at least a portion of the cfNA molecules in the sample to create an amplifiable cfNA pool.

In a fifteenth aspect, the present disclosure provides a method of preparing a cfNA in a sample for analysis without subjecting the cfNA in the sample to a nucleic acid purification step, the method comprising the steps of: i) providing a liquid sample containing a plurality of cfNA molecules; ii) performing at least one processing step on the sample; and iii) converting at least a portion of the cfNA molecules in the sample to modified cfNA by adding an exogenous nucleic acid sequence to the 5' end of at least a portion of the cfNA molecules in the sample to create an amplifiable cfNA pool.

In a sixteenth aspect, the present disclosure provides a method of preparing a cfNA in a sample for analysis without subjecting the cfNA in the sample to a nucleic acid purification step, the method comprising the steps of: i) providing a liquid sample containing a plurality of cfNA molecules; ii) performing at least one processing step on the sample; and iii) converting at least a portion of the cfNA molecules in the sample to modified cfNA by adding an exogenous nucleic acid sequence to both the 3' and 5' end of at least a portion of the cfNA molecules in the sample to create an amplifiable cfNA pool.

In a seventeenth aspect, the present disclosure provides a method of preparing a cfDNA in a sample for analysis without subjecting the cfDNA in the sample to a nucleic acid purification step, the method comprising the steps of: i) providing a liquid sample containing a plurality of cfDNA molecules; ii) performing at least one processing step on the sample; and iii) converting at least a portion of the cfDNA molecules in the sample to modified cfDNA to create an amplifiable cfDNA pool.

In an eighteenth aspect, the present disclosure provides a method of preparing a cfDNA in a sample for analysis without subjecting the cfDNA in the sample to a nucleic acid purification step, the method comprising the steps of: i) providing a liquid sample containing a plurality of cfDNA molecules; ii) performing at least one processing step on the sample; and iii) converting at least a portion of the cfDNA molecules in the sample to modified cfDNA by adding an exogenous nucleic acid sequence to the 3' end of at least a portion of the cfDNA molecules in the sample to create an amplifiable cfDNA pool.

In a nineteenth aspect, the present disclosure provides a method of preparing a cfDNA in a sample for analysis without subjecting the cfDNA in the sample to a nucleic acid purification step, the method comprising the steps of: i) providing a liquid sample containing a plurality of cfDNA molecules; ii) performing at least one processing step on the sample; and iii) converting at least a portion of the cfDNA molecules in the sample to modified cfDNA by adding an exogenous nucleic acid sequence to the 5' end of at least a portion of the cfDNA molecules in the sample to create an amplifiable cfDNA pool.

In twentieth aspect, the present disclosure provides a method of preparing a cfDNA in a sample for analysis without subjecting the cfDNA in the sample to a nucleic acid purification step, the method comprising the steps of: i) providing a liquid sample containing a plurality of cfDNA molecules; ii) performing at least one processing step on the sample; iii) converting at least a portion of the cfDNA molecules in the sample to modified cfDNA by adding an exogenous nucleic acid sequence to both the 3' and 5' ends of at least a portion of the cfDNA molecules in the sample to create an amplifiable cfDNA pool; and v) amplifying the amplifiable cfDNA pool to produce an analyzable pool of cfDNA molecules.

In a twenty-first aspect, the present disclosure provides a method of preparing a cfRNA in a sample for analysis without subjecting the cfRNA in the sample to a nucleic acid purification step, the method comprising the steps of: i) providing a liquid sample containing a plurality of cfRNA molecules; ii) performing at least one processing step on the sample; and iii) converting at least a portion of the cfRNA molecules in the sample to modified cfRNA to create an amplifiable cfRNA pool.

In twenty-second aspect, the present disclosure provides a method of preparing a cfRNA in a sample for analysis without subjecting the cfRNA in the sample to a nucleic acid purification step, the method comprising the steps of: i) providing a liquid sample containing a plurality of cfRNA molecules; ii) performing at least one processing step on the sample; and iii) converting at least a portion of the cfRNA molecules in the sample to modified cfRNA by adding an exogenous nucleic acid sequence to the 3' end of at least a portion of the cfRNA molecules in the sample to create an amplifiable cfRNA pool.

In a twenty-third aspect, the present disclosure provides a method of preparing a cfRNA in a sample for analysis without subjecting the cfRNA in the sample to a nucleic acid purification step, the method comprising the steps of: i) providing a liquid sample containing a plurality of cfRNA molecules; ii) performing at least one processing step on the sample; and iii) converting at least a portion of the cfRNA molecules in the sample to modified cfRNA by adding an exogenous nucleic acid sequence to the 5' end of at least a portion of the cfRNA molecules in the sample to create an amplifiable cfRNA pool.

In a twentieth-fourth aspect, the present disclosure provides a method of preparing a cfRNA in a sample for analysis without subjecting the cfRNA in the sample to a nucleic acid purification step, the method comprising the steps of: i) providing a liquid sample containing a plurality of cfRNA molecules; ii) performing at least one processing step on the sample; and iii) converting at least a portion of the cfRNA molecules in the sample to modified cfRNA by adding an exogenous nucleic acid sequence to both the 3' and 5' ends of at least a portion of the cfRNA molecules in the sample to create an amplifiable cfRNA pool.

In certain embodiments of each of the thirteenth through twenty-fourth aspects described above, the liquid sample is as described for the first through twelfth aspects.

In certain embodiments of each of the thirteenth through twenty-fourth aspects described above, the sample volume is as described for the first through twelfth aspects.

In certain embodiments of each of the thirteenth through twenty-fourth aspects described above, the processing step may be as described for the first through twelfth aspects.

In certain embodiments of each of the thirteenth through twenty-fourth aspects described above, the converting at least a portion of the cfNA molecules in the sample to modified cfNA to create an amplifiable cfNA pool step involves a process as described for the first through twelfth aspects.

In certain embodiments of each of the thirteenth through twenty-fourth aspects described above, the converting at least a portion of the cfNA molecules in the sample to modified cfNA to create an amplifiable cfNA pool step involves the use of an enzyme mixture as described for the first through twelfth aspects.

In certain embodiments of each of the thirteenth through twenty-fourth aspects described above, the exogenous nucleic acid sequence added to the 3' end, 5' end or both the 3' end and 5' ends of the cfNA, cfDNA and/or cfRNA is as described in the first through twelfth aspects.

In certain embodiments of each of the thirteenth through twenty-fourth aspects described above, the cfNA may be any nucleic acid. In certain embodiments, the cfNA is cfDNA. In certain embodiments, the cfNA is double-stranded cfDNA. In certain embodiments, the cfNA is single-stranded cfDNA. In certain embodiments, the cfNA is cell free-RNA (cfRNA). In certain embodiments, the cfNA is double-stranded cfRNA. In certain embodiments, the cfNA is single-stranded cfRNA.

In certain embodiments of the thirteenth through twenty-fourth aspects, the sample may contain both cfDNA and cfRNA and each of the cfDNA and cfRNA are modified to produce an amplifiable pool of both cfDNA and cfRNA molecules. In certain embodiments of the thirteenth through twenty-fourth aspects, the sample may contain both cfDNA and cfRNA and only the cfDNA is modified to produce an amplifiable pool of cfDNA molecules. In certain embodiments of the thirteenth through twenty-fourth aspects, the sample may contain both cfDNA and cfRNA and only the cfRNA is modified to produce an amplifiable pool of cfRNA molecules. In the foregoing the cfDNA may be double-stranded and/or the cfRNA may be double-stranded.

In certain embodiments of each of the seventeenth through twentieth aspects described above, the cfDNA may be double-stranded cfDNA or single-stranded cfDNA. In certain embodiments of the seventeenth through twentieth aspects, the cfDNA is double-stranded cfDNA. In certain embodiments of the seventeenth through twentieth aspects described above, the sample may further contain cfRNA (either single-stranded or double-stranded). In certain embodiments of the seventeenth through twentieth aspects, the sample may contain both cfDNA and cfRNA and only the cfDNA is modified to produce an amplifiable pool of cfDNA molecules. In certain embodiments of the seventeenth through twentieth aspects, the sample may contain both cfDNA and cfRNA and each of the cfDNA and the cfRNA is modified to produce an amplifiable pool of cfDNA and cfRNA molecules.

In certain embodiments of each of the twenty-first through twenty-fourth aspects described above, the cfRNA may be double-stranded cfRNA or single-stranded cfRNA. In certain embodiments of the twenty-first through twenty-fourth aspects, the cfRNA is double-stranded cfRNA. In certain embodiments of the twenty-first through twenty-fourth aspects described above, the sample may further contain cfDNA (either single-stranded or double-stranded). In certain embodiments of the twenty-first through twenty-fourth aspects, the sample may contain both cfRNA and cfDNA and only the cfRNA is modified to produce an amplifiable pool of cfRNA molecules. In certain embodiments of the twenty-first through twenty-fourth aspects, the sample may contain both cfRNA and cfDNA and each of the cfRNA and the cfDNA is modified to produce an amplifiable pool of cfRNA and cfDNA molecules.

In certain embodiments of each of the twenty-first through twenty-fourth aspects described above, at least 50% or more, 60% or more, 70% or more, 80% or more, 90% or more or 95% or more of the cfNA present in the sample is converted to modified cfNA to create the amplifiable cfNA pool. When the cfNA is cfDNA (including double-stranded cfDNA) such as in the seventeenth through twentieth aspects, at least 50% or more, 60% or more, 70% or more, 80% or more, 90% or more or 95% or more of the cfDNA present in the sample is converted to modified cfDNA to create the amplifiable cfDNA pool. When the cfNA is cfRNA (including double-stranded cfRNA) such as in the twenty-first to twenty-fourth aspects, at least 50% or more, 60% or more, 70% or more, 80% or more, 90% or more or 95% or more of the cfRNA present in the sample is converted to modified cfRNA to create the amplifiable cfRNA pool.

In a twenty-fifth aspect, the present disclosure provides a method of analyzing a cfNA, the method comprising the steps of: i) providing an analyzable pool of cfNA molecules by any of the methods described herein, such as the first to fourth aspects; and ii) analyzing the analyzable pool of cfNA molecules to determine a characteristic of a cfNA molecule in the analyzable pool of cfNA molecules.

In a twenty-sixth aspect, the present disclosure provides a method of analyzing a cfDNA, the method comprising the steps of: i) providing an analyzable pool of cfDNA molecules by any of the methods described herein, such as the fifth to eighth aspects; and ii) analyzing the analyzable pool of cfDNA molecules to determine a characteristic of a cfDNA molecule in the analyzable pool of cfDNA molecules.

In a twenty-seventh aspect, the present disclosure provides a method of analyzing a cfRNA, the method comprising the steps of: i) providing an analyzable pool of cfRNA molecules by any of the methods described herein, such as the ninth to twelfth aspects; and ii) analyzing the analyzable pool of cfRNA molecules to determine a characteristic of a cfRNA molecule in the analyzable pool of cfRNA molecules.

In certain embodiments of the twenty-fifth aspect, the analyzable pool is produced by the methods of the first, second, third of fourth aspects. In certain embodiments of the twenty-sixth aspect, the analyzable pool is produced by the methods of the fifth, sixth, seventh or eighth aspects. In certain embodiments of the twenty-seventh aspect, the analyzable pool is produced by the methods of the ninth, tenth, eleventh or twelfth aspects.

In each of the twenty-fifth to twenty-seventh aspects described above, the analyzing step may involve any technique suitable for use in analyzing nucleic acid molecules. Suitable techniques include, but are not limited to next generation sequencing (NGS) and PCR-based technologies, such as but not limited to, real-time quantitative PCR, blocker PCR, digital droplet PCR (ddPCR), clamping PCR, ICE-COLD PCR, castPCR, ARMS PCR, BEAMing and the like. The analyzable pool of cfNA molecules (including cfDNA and cfRNA) produced according to the methods of the present disclosure provides cfNA molecules of sufficient quantity and quality for use in these and other analytical techniques without requiring purification of the nucleic acid molecules during preparation of the analyzable cfNA pool.

In each of the twenty-fifth to twenty-seventh aspects described above, the characteristic to be determined may be any characteristic of the cfNA molecule (including cfDNA and cfRNA). More than 1 characteristic may be analyzed simultaneously. Representative characteristics include, but are not limited to, chromosomal abnormalities, single nucleotide polymorphisms, gene mutations (such as but not limited to, point mutations, deletions and insertions), methylation pattern and copy number variations. In one embodiment, the characteristic is associated with a disease.

In a twenty-eighth aspect, the present disclosure provides for a method of diagnosing a subject as suffering from or at risk for a disease, the method comprising the steps of: i) providing an analyzable pool of cfNA molecules by any of the methods described herein, such as the first to fourth aspects; ii) analyzing the analyzable pool of cfNA molecules to determine a characteristic of a cfNA molecule in the analyzable pool of cfNA molecules that is associated with the disease; and iii) determining that the subject is suffering from and/or at risk for the disease based on the presence of the characteristic or determining that the subject is not suffering from and/or at risk for the disease based on the absence of the characteristic.

In a twenty-ninth aspect, the present disclosure provides for a method of diagnosing a subject as suffering from or at risk for a disease, the method comprising the steps of: i) providing an analyzable pool of cfDNA molecules by any of the methods described herein, such as the fifth to eighth aspects; ii) analyzing the analyzable pool of cfDNA molecules to determine a characteristic of a cfDNA molecule in the analyzable pool of cfDNA molecules that is associated with the disease; and iii) determining that the subject is suffering from and/or at risk for the disease based on the presence of the characteristic or determining that the subject is not suffering from and/or at risk for the disease based on the absence of the characteristic.

In a thirtieth aspect, the present disclosure provides for a method of diagnosing a subject as suffering from or at risk for a disease, the method comprising the steps of: i) providing an analyzable pool of cfRNA molecules by any of the methods described herein, such as the ninth to twelfth aspects; ii) analyzing the analyzable pool of cfRNA molecules to determine a characteristic of a cfRNA molecule in the analyzable pool of cfRNA molecules that is associated with the disease; and iii) determining that the subject is suffering from and/or at risk for the disease based on the presence of the characteristic or determining that the subject is not suffering from and/or at risk for the disease based on the absence of the characteristic.

In certain embodiments of the twenty-eighth aspect, the analyzable pool is produced by the methods of the first, second, third of fourth aspects. In certain embodiments of the twenty-ninth aspect, the analyzable pool is produced by the methods of the fifth, sixth, seventh or eighth aspects. In certain embodiments of the thirtieth aspect, the analyzable pool is produced by the methods of the ninth, tenth, eleventh or twelfth aspects.

In each of the twenty-eighth to thirtieth aspects described above, the analyzing step may involve any technique suitable for use in analyzing nucleic acid molecules. Suitable techniques include, but are not limited to next generation sequencing (NGS) and PCR-based technologies, such as but not limited to, real-time quantitative PCR, blocker PCR, digital droplet PCR (ddPCR), clamping PCR, ICE-COLD PCR, castPCR, ARMS PCR, BEAMing and the like. The analyzable pool of cfNA molecules (including cfDNA and cfRNA) produced according to the methods of the present disclosure provides cfNA molecules of sufficient quantity and quality for use in these and other analytical techniques without requiring the purification of the nucleic acid molecules during preparation of the analyzable cfNA pool.

In each of the twenty-eighth to thirtieth aspects described above, the characteristic to be determined may be any characteristic of the cfNA molecule (including cfRNA and cfRNA). More than 1 characteristic may be analyzed simultaneously. Representative characteristics include, but are not limited to, chromosomal abnormalities, single nucleotide polymorphisms, gene mutations (such as but not limited to, point mutations, deletions and insertions), methylation pattern and copy number variations. In one embodiment, the characteristic is associated with a disease.

In a thirty-first aspect, the present disclosure provides for method of determining a therapeutic intervention for a subject suffering from a disease, the method comprising the steps of: i) providing an analyzable pool of cfNA molecules by any of the methods described herein, such as the first to fourth aspects; ii) analyzing the analyzable pool of cfNA molecules to determine a characteristic of a cfNA molecule in the analyzable pool of cfNA molecules that is associated with the disease; and iii) determining the therapeutic intervention based on the characteristic determined.

In a thirty-second aspect, the present disclosure provides for method of determining a therapeutic intervention for a subject suffering from a disease, the method comprising the steps of: i) providing an analyzable pool of cfDNA molecules by any of the methods described herein, such as the fifth to eighth aspects; ii) analyzing the analyzable pool of cfDNA molecules to determine a characteristic of a cfDNA molecule in the analyzable pool of cfDNA molecules that is associated with the disease; and iii) determining the therapeutic intervention based on the characteristic determined.

In a thirty-third aspect, the present disclosure provides for method of determining a therapeutic intervention for a subject suffering from a disease, the method comprising the steps of: i) providing an analyzable pool of cfRNA molecules by any of the methods described herein, such as the ninth to twelfth aspects; ii) analyzing the analyzable pool of cfRNA molecules to determine a characteristic of a cfRNA molecule in the analyzable pool of cfRNA molecules that is associated with the disease; and iii) determining the therapeutic intervention based on the characteristic determined.

In certain embodiments of the thirty-first aspect, the analyzable pool is produced by the methods of the first, second, third of fourth aspects. In certain embodiments of the thirty-second aspect, the analyzable pool is produced by the methods of the fifth, sixth, seventh or eighth aspects. In certain embodiments of the thirty-third aspect, the analyzable pool is produced by the methods of the ninth, tenth, eleventh or twelfth aspects.

In each of the thirty-first to thirty-third aspects described above, the analyzing step may involve any technique suitable for use in analyzing nucleic acid molecules. Suitable techniques include, but are not limited to next generation sequencing (NGS) and PCR-based technologies, such as but not limited to, real-time quantitative PCR, blocker PCR, digital droplet PCR (ddPCR), clamping PCR, ICE-COLD PCR, castPCR, ARMS PCR, BEAMing and the like. The analyzable pool of cfNA molecules (including cfDNA and cfRNA) produced according to the methods of the present disclosure provides cfNA molecules of sufficient quantity and quality for use in these and other analytical techniques without requiring the purification of the nucleic acid molecules during preparation of the analyzable cfNA pool.

In each of the thirty-first to thirty-third aspects described above, the characteristic to be determined may be any characteristic of the cfNA molecule (including cfDNA and cfRNA). More than 1 characteristic may be analyzed simultaneously. Representative characteristics include, but are not limited to, chromosomal abnormalities, single nucleotide polymorphisms, gene mutations (such as but not limited to, point mutations, deletions and insertions), methylation pattern and copy number variations. In one embodiment, the characteristic is associated with a disease.

In a thirty-fourth aspect, the present disclosure provides for a method of monitoring the treatment of a subject that has been diagnosed with a disease and is undergoing treatment with a therapeutic regimen for the treatment of the disease, the method comprising the steps of: i) providing an analyzable pool of cfNA molecules by any of the methods described herein, such as the first to fourth aspects; ii) analyzing the analyzable pool of cfNA molecules to determine a characteristic of a cfNA molecule in the analyzable pool of cfNA molecules that is associated with the disease; iii) determining if the determined characteristic is compatible with the current therapeutic treatment regimen; iv) altering the therapeutic regimen if the determined characteristic indicates the therapeutic regimen is contraindicated or not recommended or continuing the therapeutic regimen if the determined characteristics indicates the therapeutic regimen continues to be recommended; and vi) optionally repeating steps i) to iv) to monitor the therapeutic intervention at desired time intervals.

In a thirty-fifth aspect, the present disclosure provides for a method of monitoring the treatment of a subject that has been diagnosed with a disease and is undergoing treatment with a therapeutic regimen for the treatment of the disease, the method comprising the steps of: i) providing an analyzable pool of cfDNA molecules by any of the methods described herein, such as the fifth to eighth aspects; ii) analyzing the analyzable pool of cfDNA molecules to determine a characteristic of a cfDNA molecule in the analyzable pool of cfDNA molecules that is associated with the disease; iii) determining if the determined characteristic is compatible with the current therapeutic treatment regimen; iv) altering the therapeutic regimen if the determined characteristic indicates the therapeutic regimen is contraindicated or not recommended or continuing the therapeutic regimen if the determined characteristics indicates the therapeutic regimen continues to be recommended; and vi) optionally repeating steps i) to iv) to monitor the therapeutic intervention at desired time intervals.

In a thirty-sixth aspect, the present disclosure provides for a method of monitoring the treatment of a subject that has been diagnosed with a disease and is undergoing treatment with a therapeutic regimen for the treatment of the disease, the method comprising the steps of: i) providing an analyzable pool of cfRNA molecules by any of the methods described herein, such as the ninth to twelfth aspects; ii) analyzing the analyzable pool of cfRNA molecules to determine a characteristic of a cfRNA molecule in the analyzable pool of cfRNA molecules that is associated with the disease; iii) determining if the determined characteristic is compatible with the current therapeutic treatment regimen; iv) altering the therapeutic regimen if the determined characteristic indicates the therapeutic regimen is contraindicated or not recommended or continuing the therapeutic regimen if the determined characteristics indicates the therapeutic regimen continues to be recommended; and vi) optionally repeating steps i) to iv) to monitor the therapeutic intervention at desired time intervals.

In certain embodiments of the thirty-fourth aspect, the analyzable pool is produced by the methods of the first, second, third of fourth aspects. In certain embodiments of the thirty-fifth aspect, the analyzable pool is produced by the methods of the fifth, sixth, seventh or eighth aspects. In certain embodiments of the thirty-sixth aspect, the analyzable pool is produced by the methods of the ninth, tenth, eleventh or twelfth aspects.

In each of the thirty-fourth to thirty-sixth aspects described above, the analyzing step may involve any technique suitable for use in analyzing nucleic acid molecules. Suitable techniques include, but are not limited to next generation sequencing (NGS) and PCR-based technologies, such as but not limited to, real-time quantitative PCR, blocker PCR, digital droplet PCR (ddPCR), clamping PCR, ICE-COLD PCR, castPCR, ARMS PCR, BEAMing and the like. The analyzable pool of cfNA molecules (including cfDNA and cfRNA) produced according to the methods of the present disclosure provides cfNA molecules of sufficient quantity and quality for use in these and other analytical techniques without requiring purification of the nucleic acid molecules during preparation of the analyzable cfNA pool.

In each of the thirty-fourth to thirty-sixth aspects described above, the characteristic to be determined may be any characteristic of the cfNA molecule (including cfDNA and cfRNA). More than 1 characteristic may be analyzed simultaneously. Representative characteristics include, but are not limited to, chromosomal abnormalities, single nucleotide polymorphisms, gene mutations (such as but not limited to, point mutations, deletions and insertions), methylation pattern and copy number variations. In one embodiment, the characteristic is associated with a disease.

In a thirty-seventh aspect, the present disclosure provides for a method of monitoring a subject, the method comprising the steps of: i) providing an analyzable pool of cfNA molecules by any of the methods described herein, such as the first to fourth aspects; ii) analyzing the analyzable pool of cfNA molecules to determine a characteristic of a cfNA molecule in the analyzable pool of cfNA molecules that is associated with the disease; and iii) determining if the subject is in need of treatment based on the characteristic determined.

In a thirty-eighth aspect, the present disclosure provides for a method of monitoring a subject, the method comprising the steps of: i) providing an analyzable pool of cfDNA molecules by any of the methods described herein, such as the fifth to eighth aspects; ii) analyzing the analyzable pool of cfDNA molecules to determine a characteristic of a cfDNA molecule in the analyzable pool of cfDNA molecules that is associated with the disease; and iii) determining if the subject is in need of treatment based on the characteristic determined.

In a thirty-ninth aspect, the present disclosure provides for a method of monitoring a subject, the method comprising the steps of: i) providing an analyzable pool of cfRNA molecules by any of the methods described herein, such as the ninth to twelfth aspects; ii) analyzing the analyzable pool of cfRNA molecules to determine a characteristic of a cfRNA molecule in the analyzable pool of cfRNA molecules that is associated with the disease; and iii) determining if the subject is in need of treatment based on the characteristic determined.

In certain embodiments of the thirty-seventh aspect, the analyzable pool is produced by the methods of the first, second, third of fourth aspects. In certain embodiments of the thirty-eighth aspect, the analyzable pool is produced by the methods of the fifth, sixth, seventh or eighth aspects. In certain embodiments of the thirty-ninth aspect, the analyzable pool is produced by the methods of the ninth, tenth, eleventh or twelfth aspects.

In each of the thirty-seventh to thirty-ninth aspects described above, the analyzing step may involve any technique suitable for use in analyzing nucleic acid molecules. Suitable techniques include, but are not limited to next generation sequencing (NGS) and PCR-based technologies, such as but not limited to, real-time quantitative PCR, blocker PCR, digital droplet PCR (ddPCR), clamping PCR, ICE-COLD PCR, castPCR, ARMS PCR, BEAMing and the like. The analyzable pool of cfNA molecules (including cfDNA and cfRNA) produced according to the methods of the present disclosure provides cfNA molecules of sufficient quantity and quality for use in these and other analytical techniques without requiring the purification of the nucleic acid molecules during preparation of the analyzable cfNA pool.

In each of the thirty-seventh to thirty-ninth aspects described above, the characteristic to be determined may be any characteristic of the cfNA molecule (including cfDNA and cfRNA). More than 1 characteristic may be analyzed simultaneously. Representative characteristics include, but are not limited to, chromosomal abnormalities, single nucleotide polymorphisms, gene mutations (such as but not limited to, point mutations, deletions and insertions), methylation pattern and copy number variations. In one embodiment, the characteristic is associated with a disease.

DETAILED DESCRIPTION

In the following description, numerous specific details are set forth to provide a more thorough understanding of the present invention. However, it will be apparent to one of skill in the art that the embodiments disclosed may be practiced without one or more of these specific details. In other instances, well-known features and procedures well known to those skilled in the art have not been described in order to avoid obscuring the invention.

Definitions

As used in the present specification, the term "amplifiable nucleic acid pool" refers to a pool of nucleic acids that has been modified from its original state to allow for amplification of the nucleic acid molecule. In certain embodiments, an amplifiable nucleic acid pool is created by adding an exogenous nucleic acid sequence to the 3' end, the 5' end or both the 3' and 5' ends of at least a portion of the nucleic acid molecules present in the sample.

As used in the present specification, the term "amplifiable nucleic acid pool" and "amplifiable cfNA pool" refers to a plurality of nucleic acids present in a sample that have been modified to contain at least one exogenous nucleic acid sequence, wherein the exogenous nucleic acid sequence is used in a reaction to amplify the nucleic acid molecule to which the exogenous sequence is attached. In certain embodiments, a nucleic acid may contain 1 or 2 exogenous sequences.

As used in the present specification, the term "amplifiable cfDNA pool" refers to a plurality of cfDNA present in a sample that have been modified to contain at least one exogenous nucleic acid sequence, wherein the exogenous nucleic acid sequence is used in a reaction to amplify the cfDNA molecule to which the exogenous sequence is attached. In certain embodiments, a cfDNA may contain 1 or 2 exogenous sequences.

As used in the present specification, the term "amplifiable cfRNA pool" refers to a plurality of cfRNA present in a sample that have been modified to contain at least one exogenous nucleic acid sequence, wherein the exogenous nucleic acid sequence is used in a reaction to amplify the cfRNA molecule to which the exogenous sequence is attached. In certain embodiments, a cfRNA may contain 1 or 2 exogenous sequences.

As used in the present specification, the term "exogenous nucleic acid sequence" means a sequence that is not present in the nucleic acid molecules, including cfNA, cfDNA and/or cfRNA, present in a sample. In certain embodiments, the exogenous nucleic acid sequence is a sequence that does not occur in the human genome. In certain embodiments, the exogenous nucleic acid sequence contains a primer site capable of binding a primer. In certain embodiments, the primer site is a universal primer site. In certain embodiments, the exogenous nucleic acid sequence contains a replication block.

As used in the present specification, the terms "cell free nucleic acid" or "cfNA" means a segment of a nucleic acid found outside of a cell, such as in a bodily fluid, including, but not limited to, the bloodstream, cerebrospinal fluid, saliva or urine. The cfNA may originate from the subject of (for example, from a cell of a subject) or may originate from a source other than the subject (for example, from a viral infection).

As used in the present specification, the terms "cell free DNA" or "cfDNA" means a segment of a DNA found outside of a cell, such as in a bodily fluid, including, but not limited to, the bloodstream, cerebrospinal fluid, saliva or urine. The cfDNA may originate from the subject of (for example, from a cell of a subject) or may originate from a source other than the subject (for example, from a viral infection).

As used in the present specification, the terms "cell free RNA" or "cfRNA" means a segment of a RNA found outside of a cell, such as in a bodily fluid, including, but not limited to, the bloodstream, cerebrospinal fluid, saliva or urine. The terms "cell free RNA" or "cfRNA" also include DNA produced from the segment of segment of a RNA (such as for example, double-stranded cDNA). The cfRNA may originate from the subject of (for example, from a cell of a subject) or may originate from a source other than the subject (for example, from a viral infection).

As used in the present specification, the term "without subjecting the sample to a nucleic acid purification step", "have not been subject to a purification step", "unpurified" or "not subject to purification" (as well as similar terms) when used to described a sample or a nucleic acid in a sample (including cfNA, cfDNA and/or cfRNA) means that the sample/nucleic acid has not been subject to steps to specifically isolate or purify a nucleic acid (including cfNA, cfDNA and/or cfRNA) in the sample.

As used herein the term "specifically isolate" means a step or series of steps that allows nucleic acid (including cfNA, cfDNA and/or cfRNA) in a sample to be segregated from the sample based on a sequence specific characteristic of the nucleic acid (such as, for example, through the use of a probe). As used herein the term "purify" as it relates to a nucleic acid in a sample (including cfNA, cfDNA and/or cfRNA) means a step or series of steps that allows the nucleic acid (including cfNA, cfDNA and/or cfRNA) in a sample to be segregated from the sample based on a binding characteristic of the nucleic acid (for example, incubation with a nucleic acid binding reagent that binds the nucleic acid in a manner other than a sequence specific manner). Therefore, whatever the nature of the sample, the sample is not: i) subject to a step or steps to specifically isolate any nucleic acid (including cfNA, cfDNA and/or cfRNA) that may be present in the sample; or ii) subject to steps that involve the interaction of the nucleic acid (including cfNA, cfDNA and/or cfRNA) in the sample with a nucleic acid binding reagent to isolate the nucleic acid, in order to remove nucleic acid from the sample or remove all or essentially all of the components of the sample other than nucleic acid from the sample. In certain cases samples containing nucleic acid may be processed (for example, a blood sample may be processed by centrifugation or other means to produce a serum or plasma sample) and the processing may remove certain components (for example proteins, cells or other components) and/or increase the concentration of nucleic acid in the sample. Such processing is not considered to "specifically isolate" or "purify" a nucleic acid (including cfNA, cfDNA and/or cfRNA) in a sample as the nucleic acid molecule is still present with additional components of the sample and the processing is not directed specifically to a nucleic acid molecule in the sample. In one embodiment, the terms "specifically isolate" and "purify" do not include centrifugation of a sample. In another embodiment, a processing step that increases the concentration of a cfNA (including cfDNA and/or cfRNA) is not considered to "specifically isolate" or "purify" a cfNA (including cfDNA and/or cfRNA) in the sample when at least one other component of the sample is also increased in concentration.

As used herein the term "in situ" when used to described a reaction (such as amplification of nucleic acid) means the reaction takes place in the sample as provided without the need for further manipulation of the sample.

As used herein the term "about" means approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 1 percent to 20 percent up or down (higher or lower); in certain embodiments the term "about" is used herein to modify a numerical value above and below the stated value by a variance of 1 percent to 5 percent up or down (higher or lower).

As used herein the terms "animal," "subject" and "patient" as used herein include all members of the animal kingdom including, but not limited to, mammals, animals (e.g., cats, dogs, horses, swine, etc.) and humans. In a specific embodiment, the subject is a human.

As used herein the term "adding an exogenous nucleic acid sequence to the 5' and/or 3' ends of at least a portion of the cfNA molecules in the sample" or similar terms refers to the incorporation of an exogenous nucleic acid sequence into a sequence of a cfNA present in a sample or the incorporation of the exogenous nucleic acid sequence into a sequence which is the complement of at least a portion of the sequence of the cfNA. Such incorporation may be accomplished through an annealing of the exogenous nucleic acid sequence to a cfNA sequence and subsequent replication of the cfNA sequence (which may be primed by the exogenous nucleic acid sequence). Such incorporation may be accomplished by ligation of at least one strand of the exogenous nucleic acid sequence to at least one strand of the cfNA. In any event, a cfNA (or the complement of a cfNA), which may also be referred to herein as a modified cfNA, is produced in which at least the 5' and or 3' end of the cfNA contains an exogenous nucleic acid sequence.

It should be noted that as used herein and in the appended claims, the singular forms "a," "an," and "the" include plural referents unless the context clearly dictates otherwise. Thus, for example, reference to "a nucleic acid molecule" refers to one, more than one, or mixtures of such nucleic acid molecules, and reference to "an assay" includes reference to equivalent steps and methods known to those skilled in the art, and so forth.

Where a range of values is provided, it is to be understood that each intervening value between the upper and lower limit of that range, and any other stated or intervening value in that stated range, is encompassed within the invention. Where the stated range includes upper and lower limits, ranges excluding either of those included limits are also included in the invention.

Unless expressly stated, the terms used herein are intended to have the plain and ordinary meaning as understood by those of ordinary skill in the art. The definitions are intended to aid the reader in understanding the present invention, but are not intended to vary or otherwise limit the meaning of such terms unless specifically indicated. All publications mentioned herein are incorporated by reference for the purpose of describing and disclosing the formulations and methodologies that are described in the publication and which might be used in connection with the presently described invention.

Introduction

Most of the nucleic acids (DNA and RNA) in the body are located within cells, but a significant amount of extracellular nucleic acids can also be found circulating in the bloodstream. Since the first discovery of cfDNA in the blood in 1948 by Mandel and Métais, researchers have found that cfDNA discriminates patients with a disease or condition (for example cancer) and healthy individuals in two ways: first by the elevated concentration cfDNA in the blood in patients with a disease or condition; and second, by the presence of tumor-specific alterations in cfDNA in patients with a disease or condition. Tumor-specific cfDNA has been found in the blood corresponding to a wide range of cancers, such as, but not limited to, hematological, colorectal, pancreatic, skin, head-and-neck, lung, breast, gastric, prostate, and cervix. This suggests that cfDNA is a hallmark for all cancer and reflects a pathological process that can be used to diagnose cancer, to monitor disease progression, to identify therapeutic interventions and to monitor treatment responses. cfDNA are thought to enter the bloodstream through "active" release of newly synthesized nucleic acids as well as through "passive" mechanisms as end-products of necrotic and/or apoptotic cell death.

For healthy subjects, the average concentration of circulating cfDNA is 10-30 ng/mL of plasma with values of cancer patients exceeding 100 ng/mL of plasma. The estimation of cfDNA contributed by tumors using multiple methods is between 0.01 to 90% (Schwarzenbach H, et al., 2008, Ann N Y Acad Sci 1137: 190-196). Most cfDNA fragments measure between 150 to 200 base pairs in length, with a variable half-life in the circulation ranging from 15 minutes to several hours. The amount of cfDNA in the bloodstream is influenced by a variety of factors, such as, but not limited to, tumor progression, tumor location, turnover of tumor, tumor size, as well as clearance, degradation, and filtering of the cfDNA by the blood and lymphatic circulation. The most common published extraction methods for cfDNA are the commercially available spin column extraction kits. Other reported methods of extraction include magnetic beads, phenol/chloroform extraction, and alkaline salting. The efficiency of cfDNA extraction can directly impact the ability to detect mutation(s) which directly impacts assay sensitivity.

Circulating cfDNA-based non-invasive methods can be used to detect and monitor specific and predictive biomarkers for the proper treatment of cancer patients according to the molecular characterization of the specific cancer. For example by using qPCR, digital PCR or sequencing, KRAS and EFGR mutation status can be obtained from cfDNA in cancer patients before, during and after targeted therapy (Bidard F C, et al., 2013, Cancer Metastasis Rev. 32(1-2):

179-188). The whole exome sequencing of cfDNA by next generation sequencing (NGS) can provide a global, complete and real-time picture regarding molecular status of tumor progression (Diaz L A Jr, et al., 2013, Oncotarget 4(10):1856-1857). Most importantly, tumor load could be quantitatively estimated from ultra-deep cfDNA mutation profiling (Bettegowda C, et al., 2014, Sci. Transl. Med. 6(224): 224ra24). Methylation status of the tumor genome can also be detected in the cfDNA fragments (Mori T, et al., 2005, J. Clin. Oncol. 23(36): 9351-9358). Overall, the development of patient-centered molecular diagnostics with blood biopsy offers many benefits to patient care.

In the era of precision medicine, it is anticipated that patients will increasingly be treated based on the genetic architecture of their particular tumors rather than on the tumor's location or histologic features. However, cancer genomes are unstable and prone to changes under selection pressures such as the application of therapies. Therefore, genetically tailored cancer therapies require serial monitoring of the tumor genome for the improvement of clinical outcome. Such a practice is not clinically practical with current techniques. The finding that genetic and epigenetic alterations typical of primary tumors can be detected in circulating cfDNA from cancer patients, suggests that at least part of cfDNA in the blood is of tumor origin. Therefore, cfDNA analysis from the peripheral blood offers a unique opportunity for longitudinal tumor monitoring in a non-invasive fashion.

The drawbacks inherent in solid tumor sampling have been discussed above.

In contrast, blood biopsy, specifically cfDNA analysis, offers an easily obtainable, minimally invasive, and longitudinal solution for precision cancer management. Clinical tests employing cfDNA are inherently specific, sensitive, and are able to capture both intra- and inter-tumor heterogeneity in real time (Dawson S J, et al., 2013, N Engl J Med 368: 1199-1209). Detection of low-frequency mutations through periodic "blood biopsy" analysis could monitor tumor progression before the lesions are large enough to be detected by imaging (Diaz L A Jr, et al., 2012, Nature 486(7404): 537-540). Analysis beyond a single mutation could also be warranted to capture tumor heterogeneity for effective treatment decision-making (Sequist L V, et al., 2011, Sci. Transl. Med. 23(75): 75ra26). Blood biopsies are not as spatially limited as tissue biopsies, and can display a global spectrum of mutations that occur throughout cancer development in our body. Nevertheless, the sensitivity of conventional analytical methods such as Sanger sequencing is not sufficient to detect low frequency variants. In this respect, advanced NGS technology could provide a cost-effective alternative for high-throughput analysis of multiple mutations with high sensitivity. In addition, PCR-based platforms with the features of single-molecule amplification and/or selective enrichment of tumor-specific cfDNA from a dominantly normal population, have demonstrated unprecedented assay sensitivity.

Assessing cancer-related genetic alterations via cfDNA can also avoid positional bias inherent in direct sampling of tumors, where the spectrum of mutations observed can differ between different biopsy sections within the same malignant tissue. Although the precise mechanism of DNA release into the bloodstream remains uncertain, it is believed to result from a combination of apoptosis, necrosis and active release from tumor cells. Such informative cfDNA biomarkers have shown promise for improving early detection, diagnosis, prognosis, disease and therapy monitoring in almost all cancer types (Gormally E, et al., 2007, Mutat. Res. 635(2-3): 105-117; Tong Y K, et al., 2006 Clin. Chim. Acta 363(1-2): 187-196; Gautschi O, et al., 2004, J. Clin. Oncol. 22(20): 4157-4164; Xue X, et al., 2006 Ann. N. Y. Acad. Sci. 1075:154-164; Khan S, et al., 2004 Intl. J. Cancer 110(6): 891-895).

A comparison of the key characteristics of blood biopsy and solid tumor sampling is shown in Table A.

TABLE A

Comparison of blood biopsy and solid tumor sampling

| Key Characteristics | Blood Biopsy | Tissue Biopsy |
| --- | --- | --- |
| Invasiveness | No | Yes |
| Sample Availability Throughout the Disease Process | Yes | No |
| Sample Stability When Maintained Ex Vivo | Yes | Stable when processed |
| Utility for Longitudinally Disease Monitoring | Yes | No |
| Cost | Low | High |
| Processing Time | Short | Long (involvement of tissue sectioning, staining and pathologists) |
| Rejection/Failure Rate | Low | High (due to QNS or TNI) |
| Starting Material for Multiple Testing | High | Scarce |

Table Abbreviations:
QNS: Quantity Not Sufficient;
TNI: Tumor Not Identified

Although higher levels of plasma cfDNA are consistently detected in cancer patients compared to healthy individuals, there is considerable variation among studies and methodologies. These variations could be attributed to differences in study cohorts, pre-analytical sample preparation and the methods used to isolate and quantify cfDNA (Xue X, et al., 2006, Ann. N. Y. Acad. Sci. 1075:154-164; Boddy J L, et al., 2005, Clin. Cancer Res. 11(4): 1394-1399; Wu T L, et al. 2002, Clin. Chim. Acta 321(1-2): 77-87; Chiu R W, et al. 2001, Clin. Chem. 47(9): 1607-1613). Circulating cfDNA is a challenging analyte for extraction owing to its low concentration, heterogeneous size distribution and fragmented nature in plasma. As a result, isolation of cfDNA is challenging because of the requirement of large volume input, costs, and labor-intensity. There is no existing standard protocol for cfDNA extraction, purification or quantification. Many laboratories employ commercially available extraction kits, whereas others develop their own isolation methods. The most popular commercially available kit is the QIAamp circulating nucleic acid kit (Qiagen), in which a silica membrane preferably binds small fragments of cfDNA in a spin column format, providing a fast and easy way to purify cfDNA for further genomic analysis. However, due to the unavoidable loss in steps such as binding, washing and elution, the recovery efficiency of cfDNA by current methodologies is extremely low, leading to the requirement of large volume of starting materials (>10 mL of blood). Furthermore, such silica membrane binding techniques do not efficiently recover cfDNA fragments of various sizes, further biasing the downstream analysis.

Most current research in the liquid biopsy field is focused on novel technologies to selectively enrich or amplify tumor-specific cfDNA from a subject. However, as discussed above the starting material remains incomplete as the cfDNA isolated by current techniques represents only a fraction of the cfDNA originally present in the sample.

Therefore, no matter how sensitive the enrichment and detection technology is downstream, these techniques cannot compensate for the cfDNA already lost during sample preparation upstream. Furthermore, the prior art techniques are not consistent in recovering cfDNA fragments of various sizes.

Therefore, the art is lacking a fit-for-purpose sample preparation method that can efficiently recover both higher-molecular-weight (necrotic death) and lower-molecular-weight (apoptotic death) cfNA species (including cfDNA and/or cfRNA) for the accurate quantification as well as detection of tumor-specific mutation profiles from cell-free nucleic acid in the same sample. The present disclosure provides such a method and allows for the improvement of analytical sensitivity and specificity in cfDNA analysis.

Methods of Amplification

The present disclosure provides a solution to at least three major unsolved challenges in the clinical application of liquid biopsy, including application cfNA-based liquid biopsy to patient care: i) input sample volume; ii) output quantity of cfNA for analysis; and iii) quality of output cfNA for analysis. The present disclosure provides a method of preparing cfNA (including cfDNA and/or cfRNA) in a sample for analysis without subjecting the sample to a nucleic acid purification step. In such methods, the sample volume required is lower than the prior art methods (as low as 10 to 50 microliters of whole blood are required to produce a suitable plasma sample), the risk of contamination is decreased as no nucleic acid purification step is required and the recovery of the entire spectrum of cfNA in the sample is increased as no nucleic acid purification is required. The present disclosure also provides methods for use of the cfNA, for example a method of analyzing a cfNA (including cfDNA and/or cfRNA) in a sample, where the cfNA is prepared using the methods of the present disclosure (i.e., the sample has not been subject to a nucleic acid purification step).

The nucleic acid prepared by the methods of the present disclosure provides for superior utilization of cfNA in the sample as the need to purify or recover the cfNA prior to amplification and analysis is eliminated. The present disclosure provides for in situ amplification of the cfNA in the sample and can be performed in a single reaction (i.e., a single tube or single well of a multi-well plate). Furthermore, the cfNA prepared by the methods of the present disclosure is of higher quality than the cfNA prepared by the methods of the prior art allowing for superior downstream analysis. Still further, the methods of the present disclosure require only a small volume of starting sample. Volumes as low as 10-50 microliters may be used (droplet volumes). For example, the present disclosure shows the amplification and/or analysis of cfNA from 10 microliters of urine and 10-20 microliters of plasma (which can be obtained from approximately 50 microliters of whole blood). As such, the methods of the present disclosure are suitable for next-generation liquid biopsy, point-of-care, and nano- or miniaturized microfluidic "lab-on-a-chip" diagnostics devices. In addition, a broader range of cfNA molecules can be analyzed (for example, a broad distribution of both small and large cfNA fragments) using the methods of the present disclosure. For example, the methods of the present disclosure demonstrate no bias with regard to nucleic acid fragment size.

Methods of ISA of cfNA and Methods for Preparing a cfNA for Amplification

The methods of the present disclosure utilize in situ amplification of cfNA in a liquid sample without the need to subject the sample to nucleic acid purification steps. Therefore, cfNA can be amplified directly in situ from a liquid sample (for example, urine, CSF, saliva, plasma or serum) without the need for a nucleic acid purification step (for example, the cfNA is not specifically isolated or purified). This feature, at least in part, eliminates loss of cfNA in the sample during preparative steps, with the advantage of the full representation of cfNA in the sample is available for subsequent analysis. In the methods described herein, the sample volume is significantly reduced as compared to the prior art.

In addition, the methods of the present disclosure provide an analyzable pool of cfNA that is of high quality and can be used in a variety of downstream analytic techniques. Any known analytic technique may be used in conjunction with the methods of the present disclosure to analyze the analyzable pool of cfNA generated by the methods of the present disclosure. Suitable techniques include, but are not limited to next generation sequencing (NGS) and PCR-based technologies, such as but not limited to, real-time quantitative PCR, blocker PCR, digital droplet PCR (ddPCR), clamping PCR, ICE-COLD PCR, castPCR, ARMS PCR, BEAMing and the like. Previously, it was believed that highly purified cfNA was required for use with these techniques.

The present disclosure provides for a method of in situ amplification of a nucleic acid in a sample (including, for example, cfDNA) to produce an amplifiable nucleic acid pool. The amplifiable nucleic acid pool may be amplified to produce an analyzable nucleic acid pool and may be used for subsequent analysis as described herein. Furthermore, the present disclosure provides for a method of preparing a nucleic acid (including, for example, cfDNA) in a sample for amplification. The methods described are carried out without subjecting the sample to a nucleic acid purification step (for example, the cfNA is not specifically isolated or purified). Furthermore, in certain embodiments, the method is performed with sample volumes from 10 to 50 microliters. Certain embodiments of the method are provided below. Still further, in certain embodiments all the described reactions are carried out in a single reaction vessel.

The nucleic acid molecule may be any nucleic acid. In certain embodiments, the nucleic acid is cfDNA. In certain embodiments, the nucleic acid is double-stranded cfDNA. In certain embodiments, the nucleic acid is double-stranded cfRNA.

The description below refers to each of the embodiments and aspects of the method disclosed herein. While the following discussion may refer to cfDNA for simplicity as a representative cfNA the methods of the present disclosure are applicable to any type cfNA and should not be limited to cfDNA.

The methods of the present disclosure provide a method of ISA of cfNA in a sample, the method comprising: 1) providing a liquid sample containing cfNA (including cfDNA and/or RNA); 2) subjecting the sample to a processing step; 3) converting at least a portion of the cfNA molecules in the sample to modified cfNA by adding an exogenous nucleic acid sequence to the 5' and/or 3' ends of at least a portion of the cfNA molecules in the sample to create an amplifiable cfNA pool; and 4) amplifying the amplifiable cfNA pool to create and analyzable pool of cfNA.

As discussed herein, the cfNA may be cfDNA (such as double-stranded cfDNA). Therefore, the present disclosure provides a method of ISA of cfDNA in a sample, the method comprising: 1) providing a liquid sample containing cfDNA; 2) subjecting the sample to a processing step; 3) converting at least a portion of the cfDNA molecules in the sample to modified cfDNA by adding an exogenous nucleic acid sequence to the 5' and/or 3' ends of at least a portion of the cfDNA molecules in the sample to create an amplifiable cfDNA pool; and 4) amplifying the amplifiable cfDNA pool to create and analyzable pool of cfDNA.

As discussed herein, the cfNA may be cfRNA. Therefore, the present disclosure provides a method of ISA of cfRNA in a sample, the method comprising: 1) providing a liquid sample containing cfRNA; 2) subjecting the sample to a processing step; 3) converting at least a portion of the cfRNA molecules in the sample to modified cfRNA by adding an exogenous nucleic acid sequence to the 5' and/or 3' ends of at least a portion of the cfRNA molecules in the sample to create an amplifiable cfRNA pool; and 4) amplifying the amplifiable cfRNA pool to create and analyzable pool of cfRNA.

The present disclosure provides a method of preparing a cfNA in a sample for analysis without subjecting the cfNA in the sample to a nucleic acid purification step, the method comprising the steps of: i) providing a liquid sample containing a plurality of cfNA molecules; ii) performing at least one processing step on the sample; and iii) converting at least a portion of the cfNA molecules in the sample to modified cfNA to create an amplifiable cfNA pool.

As discussed herein, the cfNA may be cfDNA (such as double-stranded cfDNA). Therefore, the present disclosure provides a method of preparing a cfNA in a sample for analysis without subjecting the cfNA in the sample to a nucleic acid purification step, the method comprising the steps of: 1) providing a liquid sample containing cfDNA; 2) subjecting the sample to a processing step; and 3) converting at least a portion of the cfDNA molecules in the sample to modified cfDNA by adding an exogenous nucleic acid sequence to the 5' and/or 3' ends of at least a portion of the cfDNA molecules in the sample to create an amplifiable cfDNA pool.

As discussed herein, the cfNA may be cfRNA. Therefore, the present disclosure provides a method of preparing a cfNA in a sample for analysis without subjecting the cfNA in the sample to a nucleic acid purification step, the method comprising the steps of: 1) providing a liquid sample containing cfRNA; 2) subjecting the sample to a processing step; 3) converting at least a portion of the cfRNA molecules in the sample to modified cfRNA by adding an exogenous nucleic acid sequence to the 5' and/or 3' ends of at least a portion of the cfRNA molecules in the sample to create an amplifiable cfRNA pool; and 4) amplifying the amplifiable cfRNA pool to create and analyzable pool of cfRNA.

The methods of the present disclosure specifically include those methods of the first to twelfth and thirteen through twenty-fourth aspects set forth in the Summary of the Disclosure section above. The descriptions below apply to both the methods of ISA and methods for preparing a cfNA for analysis.

In certain embodiments, at least a portion of the cfNA (including cfDNA and/or cfRNA) in the sample contains 1 exogenous nucleic acid sequence at either the 5' end or the 3' end of the cfNA. In certain embodiments, at least a portion of the cfNA (including cfDNA and/or cfRNA) in the sample contains 2 exogenous nucleic acid sequences (1 at the 5' end and 1 at the 3' end). When multiple exogenous nucleic acid sequences are present, the exogenous nucleic acid sequences may be the same of may be different from one another. In certain embodiments, an exogenous nucleic acid sequence is added to both the 3' and 5' ends of at least a portion of the cfNA (including cfDNA and/or cfRNA) molecules present in the sample.

A liquid sample is provided that contains a plurality of cfNA molecules (for example, cfDNA and/or cfRNA). The liquid sample may be any liquid sample obtained from the subject. In certain embodiments, the liquid sample is a blood sample, a serum sample, a plasma sample, a saliva sample, a CSF sample, a saliva sample or a urine sample. The liquid sample may be processed if desired. For example, a blood sample may be processed to remove cell and provide a plasma/serum fraction. The liquid sample may be used directly without any processing. The nature of the liquid sample will determine, at least in part, if a processing step is required. The liquid sample in one embodiment does not contain whole cells or cell fragments. The processing step may be used to eliminate unwanted material from the sample, such as cells, cell fragments and the like. Whatever the nature of the sample, the cfNA in the sample is not specifically isolated or purified. In certain embodiments, the liquid sample is from a subject, such as a human subject. In certain embodiments, the liquid sample is from a subject, including a human subject, suspected of having a disease or condition, such as cancer, a bacterial infection or a viral infection. In certain embodiments, the liquid sample is from a subject, including a human subject, that is undergoing treatment for a disease or condition. In some embodiments, the liquid sample is taken serially over time from a subject, including a human subject, while the subject is undergoing treatment for a disease or condition (including before treatment is initiated, during treatment and/or after treatment has ceased).

In one embodiment, the volume of the liquid sample is less than 1 ml. In another embodiment, the volume of the liquid sample is less than 0.5 ml. In another embodiment, the volume of the liquid sample is less than 0.1 ml. In another embodiment, the volume of the liquid sample is less than 0.05 ml. In certain embodiments, the volume of the liquid sample is from 10 to 1000 microliters. In certain embodiments, the volume of the liquid sample is from 10 to 750 µL. In certain embodiments, the volume of the liquid sample is from 10 to 500 µL. In certain embodiments, the volume of the liquid sample is from 10 to 250 µL. In certain embodiments, the volume of the liquid sample is from 10 to 100 µL. In certain embodiments, the volume of the liquid sample is from 10 to 50 µL. The nature of the sample may determine, at least in part, the sample volume required.

In one embodiment, the processing step is diluting the sample. Therefore, the sample containing cfNA may be optionally diluted. In certain embodiments, the sample is diluted in a solution that is compatible with the further reactions described herein. In certain embodiments, the sample is diluted in an amplification acceptable solution. An "amplification acceptable solution" is a solution that is compatible with the nucleic acid amplification reactions that are used for the amplification of the modified cfDNA molecules in the sample and one that does not degrade cfNA in the sample. Representative solutions that may be used are known in the art and include, but are not limited to, phosphate buffered saline (PBS), PCR amplification buffers, nuclease free water and Tris-based buffers. In certain embodiments, the sample is not diluted. In certain embodiments when a plasma or serum sample is used, the sample is diluted 1-20 fold, 1-10 fold or 1-5 fold, such as with an amplification acceptable solution. In certain embodiments, the solution is PBS. In certain embodiments, the solution is 10 mM Tris, pH 8.0; 1 mM EDTA. In certain embodiments, the solution is nuclease free water. In certain embodiments, plasma and serum samples are diluted. In certain embodiments, urine samples are not diluted. The amplification acceptable solution may contain agents to prevent degradation of the cfNA in the sample. In certain embodiments, the amplification acceptable solution does not contain agents to prevent degradation of the cfNA in the sample.

In one embodiment, the processing step is heating the sample. Therefore, the sample containing cfNA may be optionally heated. The heating serves, at least in part, to denature proteins, disassociate cfNA complexes, inactivate nucleases in the sample (for example, DNase and/or RNase) and fragment the cfDNA in the sample. The heating step may be varied. In one embodiment, the sample is heated at a temperature from 70° C. to 120° C., from 80° C. to 110° C. or 90° C. to 100° C. The sample may be heated from 1 to 20 minutes, from 1 to 10 minutes or 1 to 5 minutes. In a specific embodiment, the sample is heated at 95° C. for 4 minutes.

In one embodiment, the processing step is fragmenting the cfNA in the sample. As discussed herein, cfNA from various sources may have different fragment size distributions. As used in the methods described herein, in certain embodiments it is preferred the cfNA has a fragment size distribution from 50 bp to 2,000 bp. In certain embodiments, the cfNA has a fragment size distribution from 100 bp to 1,000 bp. In certain embodiments, the cfNA has a fragment size distribution from 50 bp to 600 bp. In certain embodiments, the cfNA has a fragment size distribution from 50 bp to 500 bp. In certain embodiments, the cfNA has a fragment size distribution from 100 bp to 500 bp. In certain embodiments, the cfNA has a fragment size distribution from 100 bp to 400 bp. In certain embodiments, the cfNA has a fragment size distribution from 100 bp to 300 bp. In certain embodiments, the cfNA has a fragment size distribution from 100 bp to 200 bp. In certain embodiments, the cfNA has a fragment size distribution from 200 bp to 300 bp, from 300 bp to 400 bp, from 400 bp to 500 bp or from 500 bp to 600 bp. In certain embodiments, a major portion of the cfNA has a fragment size distribution from 100 bp to 2,000 bp, or any of the ranges discussed above. By "major portion" it is meant at least 50% of the cfNA in the sample, such as at least 60%, at least 70%, at least 80%, at least 90% or greater. Therefore, the sample containing cfNA may be optionally fragmented. In certain embodiments, after the fragmenting step, the cfNA has a fragment size distribution from 50 bp to 600 bp, 100 bp to 500 bp, 100 bp to 400 bp, 100 bp to 300 bp, 100 bp to 200 bp, 200 bp to 300 bp, 300 bp to 400 bp, 400 bp to 500 bp or 500 bp to 600 bp. The fragmentation step may be accomplished using any method known in the art. As discussed above, in one embodiment the fragmentation may be accomplished by heating the sample. When heating is used to fragment cfNA, a divalent cation (for example, magnesium) may be added to the sample. In one embodiment, the fragmentation is accomplished by physical means, such as but not limited to, acoustic shearing, sonication and hydrodynamic shear.

In one embodiment, the processing step is diluting and heating. In one embodiment, the processing step is diluting and fragmenting. In one embodiment, the processing step is heating and fragmenting. In one embodiment, the processing step is dilution, heating and fragmenting.

In certain embodiments, at least a portion of the cfNA molecules in the sample are converted to modified cfNA by adding an exogenous nucleic acid sequence to the 5' end of at least a portion of the cfNA molecules in the sample to create an amplifiable cfNA pool. In certain embodiments, at least a portion of the cfNA molecules in the sample to modified cfNA by adding an exogenous nucleic acid sequence to the 3' end of at least a portion of the cfNA molecules in the sample to create an amplifiable cfNA pool. In certain embodiments, at least a portion of the cfNA molecules in the sample to modified cfNA by adding an exogenous nucleic acid sequence to both the 5' end and 3' end of at least a portion of the cfNA molecules in the sample to create an amplifiable cfNA pool.

In order to add the exogenous nucleic acid sequence to at least a portion of the cfNA molecules in the sample, the cfNA may be treated to produce cfNAs that may be efficiently linked to the exogenous nucleic acid sequences (referred to as an "optimized cfNA"). The cfNA in the sample is not homogenous, particularly at the 5' and/or 3' ends. Therefore, in certain embodiments, at least a portion of the cfNA in the sample are transformed to optimized cfDNA prior to the addition of the exogenous nucleic acid sequence(s). The optimized cfNA may be prepared by a number of methods, which may depend in part, on the nature of the exogenous nucleic acid sequence(s) to be added. In certain embodiments, the cfNA in the sample is fragmented as discussed herein prior to adding the exogenous nucleic acid sequences to a least a portion of the cfNA molecules in the sample.

In on embodiment, the cfNA are end repaired to produce cfNA with blunt ends. By such end repair, any 5' and/or 3' overhangs are filled in using a suitable polymerase. It is preferred that the polymerase have in addition to the 5'-3' polymerase activity a 3'-5' exonuclease/proofreading activity, although the 3'-5' exonuclease activity is not required. For example, for cfDNA T4 DNA polymerase, the Klenow fragment of DNA polymerase I or Taq DNA polymerase may be used. The exogenous nucleic acid sequence may be added directly to one or both of the 3' and 5' ends of at least a portion of the cfNA in the sample by ligation.

In another embodiment, cfNA in the sample is end repaired (for example, using a polymerase) to generate a 3' overhang on one or both ends of the cfNA (which can be a single adenine or poly-adenosine sequence created by the polymerase). The exogenous nucleic acid sequences are designed to have complementary sequences to hybridize to the 3' overhangs and are subsequently ligated to one or both of the 3' and 5' ends of at least a portion of the cfDNA molecules in the sample.

In another embodiment, one or both of the 3' ends of the cfNA is modified using terminal deoxynucleotidyl transferase (TdT) to create a homopolymer tail (for example, a poly-adenine sequence), which permits the addition of the exogenous nucleic acid sequence with complementary nucleotide sequences (for example, poly-thymine). DNA ligase may be used to seal the single-strand nick.

In any of the foregoing, a 5' phosphate may be added with a nucleotide kinase activity (such as T4 polynucleotide kinase).

A variety of enzyme mixtures may be used to accomplish the foregoing reactions. In certain embodiments, the enzyme mixture may comprise following components:

1) a polymerase having a 5'-3' polymerase activity with or without a 3'-5' exonuclease activity and ii) a ligase;

2) a polymerase having a 5'-3' polymerase activity with or without a 3'-5' exonuclease activity, ii) a ligase and iii) a polynucleotide kinase;

3) a polymerase having a 5'-3' polymerase activity with or without a 3'-5' exonuclease activity, ii) a ligase, iii) a polynucleotide kinase and iv) a replication block activating activity;

4) a polymerase having a 5'-3' polymerase activity with or without a 3'-5' exonuclease activity, ii) a ligase, iii) a polynucleotide kinase, iv) a replication block activating activity and v) a nucleic acid nicking enzyme activity;

5) a polymerase having a 5'-3' polymerase activity with or without a 3'-5' exonuclease activity, ii) a ligase, iii) a polynucleotide kinase, iv) a replication block activating activity, v) a nucleic acid nicking enzyme activity and vi) a nucleic acid binding protein.

In certain embodiments, the enzyme mixture may comprise following components:

1) a DNA polymerase having a 5'-3' polymerase activity with or without a 3'-5' exonuclease activity and ii) a DNA ligase;

2) a DNA polymerase having a 5'-3' polymerase activity with or without a 3'-5' exonuclease activity, ii) a DNA ligase and iii) a DNA polynucleotide kinase;

3) a DNA polymerase having a 5'-3' polymerase activity with or without a 3'-5' exonuclease activity, ii) a DNA ligase, iii) a DNA polynucleotide kinase and iv) a uracil-DNA glycosylase activity;

4) a DNA polymerase having a 5'-3' polymerase activity with or without a 3'-5' exonuclease activity, ii) a DNA ligase, iii) a DNA polynucleotide kinase, iv) uracil-DNA glycosylase activity and v) a single-strand DNA nucleic acid nicking enzyme activity;

5) a DNA polymerase having a 5'-3' polymerase activity with or without a 3'-5' exonuclease activity, ii) a DNA ligase, iii) a DNA polynucleotide kinase, iv) a uracil-DNA glycosylase activity, v) a single-strand DNA nucleic acid nicking enzyme activity and vi) a single-stranded DNA binding protein.

In certain embodiments, the enzyme mixture may comprise following components:

1) T4 DNA polymerase and ii) T4 DNA ligase or the Klenow fragment of DNA polymerase I and ii) T4 DNA ligase;

2) T4 DNA polymerase, ii) T4 DNA ligase and iii) the Klenow fragment of DNA polymerase I 3) T4 DNA polymerase, ii) T4 DNA ligase, iii) the Klenow fragment of DNA polymerase I, and iv) T4 polynucleotide kinase;

4) T4 DNA polymerase, ii) T4 DNA ligase, iii) the Klenow fragment of DNA polymerase I, iv) T4 polynucleotide kinase, and v) uracil-DNA glycosylase; or 5) T4 DNA polymerase, ii) T4 DNA ligase, iii) the Klenow fragment of DNA polymerase I, iv) T4 polynucleotide kinase, v) uracil-DNA glycosylase and Nb.BbvC1.

Any of the foregoing may further comprise a single-stranded binding protein (such as for example, *E. coli* single-stranded binding protein).

In certain embodiments, the enzyme mixture comprises T4 DNA polymerase, T4 DNA ligase; the Klenow fragment of DNA polymerase I, T4 polynucleotide kinase, uracil-DNA glycosylase and Nb.BbvC1. In certain embodiments, the enzyme mixture comprises Klenow fragment of DNA polymerase I and T4 DNA ligase.

The concentration of the various enzymes that may be used in the methods disclosed herein may be varied. In one embodiment, the enzymes are used in the following concentration ranges: T4 DNA polymerase from 2-15 U, the Klenow fragment from 2-20 U, T4 DNA ligase from 100-1,000 U, T4 polynucleotide kinase from 5-20 U, Nb.BbvC1 from 5-20 U, and uracil-DNA glycosylase from 1-6 U; *E. coli* single-strand binding protein may be present from 50-500 ng.

A variety of buffer/reaction solutions may be used in the methods of the present disclosure as is known in the art. In one embodiment, the reaction solution comprises 20-75 mM potassium acetate, 10-100 mM Tris-acetate (pH 7.9 at 25° C.), 1-30 mM magnesium acetate, 0.1-20 mM DTT, 5-100 μM dNTP, 0.5-2 mM of ATP, and 100-400 ug/mL BSA. In another embodiment, the reaction solution comprises 20-75 mM NaCl, 10-100 mM Tris-Cl, pH 7.0-8.0, 1-30 mM $MgCl_2$, 0.1-20 mM DTT 5 to 100 μM dNTP and 0.5-2 mM of ATP.

In certain embodiments, the enzyme mixture is subject to a sequential heating program (such as by using a thermal cycler) to initiate and complete the reaction. In one embodiment, the sequential heating program consists of 2 heating steps of a defined duration, 3 heating steps of a defined duration, 4 heating steps of a defined duration or 5 or more heating steps of a defined duration. The duration of the individual heating steps may be independently varied and may last from 1 to 40 minutes, such as 5 to 30 minutes, 10 to 25 minutes, 1 to 5 minutes, 20 minutes or 5 minutes. The sequential heating program serves to allow certain enzymes in the enzyme mixture to be preferentially active at defined times by altering the temperature of the sample. By preferentially active, it is meant that 1 or more of the enzymes in the enzyme mixture will show greater activity than at least one other enzyme in the enzyme mixture. In this manner, the various reactions required for the production of the amplifiable cfNA pool can be sequenced, at least to a partial degree. The sequential heating program starts off at a temperature at which a polymerase activity is preferentially active (for example T4 DNA polymerase and/or the Klenow fragment) allowing for the formation of optimal cfNA, followed by a temperature at which a ligase is preferentially active allowing for the ligation of the exogenous nucleic acid sequence(s) to the cfNA. Other heating steps may also be included. For example, a temperature step may be included to allow for the cleavage of the exogenous nucleic acid sequence. As a further example, a temperature step may be included that inactivates all or some of the enzymes in the enzyme mixture.

Exemplary temperature ranges for the sequential heating program include 12° C. to 20° C., 20° C. to 30° C., 30° C. to 40° C. and 60° C. to 90° C. In a particular embodiment, the temperature ranges for the sequential heating program are: 14° C. to 18° C. and 22° C. to 26° C.; 14° C. to 18° C., 22° C. to 26° C. and 70° C. to 80° C.; or 14° C. to 18° C., 22° C. to 26° C., 35° C. to 39° C. and 70° C. to 80° C. Each temperature range may be maintained for a defined duration before progressing to the next temperature range.

A representative sequential heating program that may be used with the methods of the present disclosure is: i) 16° C. for 20 min; ii) 24° C. for 20 min; iii) 37° C. for 20 min; iv) 75° C. for 5 min (inactivation); and v) 4° C. (hold; this step is optional if immediate PCR amplification is desired). The result of the process is an amplifiable pool of cfDNA molecules having a primer site at one or both of the 5' and 3' ends of the modified cfDNA molecules. The result of this reaction is the amplifiable pool of cfDNA molecules.

In the foregoing, all enzymatic reactions occur in the original sample without the need for cfNA purification (the cfNA is not specifically isolated or purified) and occur in a single reaction vessel without the need to remove components, remove products or substrates or otherwise "clean-up" the reaction between steps.

The result of the foregoing is the creation of an amplifiable pool of cfNA molecules that may be used to create the analyzable pool of cfNA molecules.

The exogenous nucleic acid sequence contains a primer site capable of binding a primer, which is used in the amplification of the amplifiable pool of cfNA. The term "capable of binding a primer" is meant to include a primer site that has a sequence which is complementary to the sequence of a specific primer as well as a primer site that has a sequence identical to the sequence of a specific primer (in which case the sequence complementary to the primer is produced during an initial replication step as discussed herein). In certain embodiments, the exogenous nucleic acid sequence contains a primer site complementary to a specific primer or a sequence identical to a specific primer, which creates the primer site after an initial round of DNA synthesis. In certain embodiments, the primer site is a universal primer site. As such a universal primer site is added to the 3', 5' or both the 3' and 5' ends of at least a portion of the cfNA molecules in the sample. The primer site added to the 3' end is referred to as a 3' primer site and the primer site added at the 5' end is referred to as the 5' primer site. In one embodiment, each of the 3' primer sites are identical for each cfNA molecule modified and each of the 5' primer sites are identical for each cfNA molecule modified, with the 3' and 5' primer sites being distinct from one another (i.e., capable of binding distinct primers in a sequence specific manner). As such, a single pair of primers may be used to amplify the amplifiable cfNA pool, simplifying the conditions for amplification by eliminating the complexity of optimizing amplification conditions for multiple priming sites. In one embodiment, each of the 3' and 5' primer sites are identical for each cfNA molecule modified and each of the 3' and 5' primer sites are capable of binding the same primers in a sequence specific manner. A single primer may be used to amplify the amplifiable cfNA pool further simplifying the conditions for amplification by eliminating the complexity of optimizing amplification conditions for multiple priming sites. In certain embodiments, the 3' and/or 5' primer binding sites are sequences that are not found in the human genome. In certain embodiments, the 3' and/or 5' primer sites are designed such that the respective primers bind the 3' and/or 5' binding sites under substantially the same amplification conditions. In certain embodiments, the 3' and/or 5' primer sites are designed such that the respective primers bind the 3' and/or 5' binding sites with a melting temperature and/or annealing temperature that are within 1° C. to 2° C. of one another or within 2° C. to 4° C. of one another.

In one embodiment, the exogenous nucleic sequences have the sequence shown below, with $N_{6-10}$ and $N_{3-6}$ representing any nucleic acid sequence. The respective primers for each site are also provided.

```
Adaptor 1:
                                        (SEQ ID NO: 1)
5'-(N6-10)ATTAACCCTCACTAAAG(N3-6)-3'

Adaptor 2:
                                        (SEQ ID NO: 2)
5'-(N6-10)TAATACGACTCACTATAGGG(N3-6)-3'

5' Primer:
                                        (SEQ ID NO: 3)
5'-ATTAACCCTCACTAAAG-3'-

3' Primer:
                                        (SEQ ID NO: 4)
5'-TAATACGACTCACTATAGGG-3'-
```

In another embodiment, the exogenous nucleic sequences have the sequence shown below. The respective primers for each site are also provided.

```
Adaptor:
                                        (SEQ ID NO: 5)
5'-OH-
TGTGTTGGGTGTGGUUUUUATTTAATACGACTCACTATAGACCCTCAGCA
CCACCACACCCAACACA-3'

Primer:
                                        (SEQ ID NO: 6)
5'-ACTCACTATAGACCCTCAGCACCAC-3'
```

In another embodiment, the exogenous nucleic sequences have the sequence shown below. The respective primers for each site are also provided.

```
Adaptor:
                                        (SEQ ID NO: 7)
5'-
TGTGTTGGGTGTGGUUUUUATTTAATACGACTCACTATAGACCCTCAGCA
CCACCACACCCAACACA(N)n-3',
``` where N can be any nucleotide and n is an integer from 0 to 10. In certain embodiments, N is adenine and n is from 1 to 5 or n is 1 (such as SEQ ID NO: 9). In certain embodiments, n is 0 (such as SEQ ID NO: 10)

```
                                        (SEQ ID NO: 9)
5'-
TGTGTTGGGTGTGGUUUUUATTTAATACGACTCACTATAGACCCTCAGCA
CCACCACACCCAACACAA-3'

(SEQ ID NO: 10)
5'-
TGTGTTGGGTGTGGUUUUUATTTAATACGACTCACTATAGACCCTCAGCA
CCACCACACCCAACACA

Primer:
                                        (SEQ ID NO: 8)
5'-TGAGTGATATCTGGGAGTCGAGGTG
```

In certain embodiments, the exogenous nucleic acid contains a replication block. As used herein the term "replication block" refers to a nucleic acid sequence that interferes with or stops the action of a DNA polymerase such that the DNA polymerase does not create a complementary nucleic acid strand past the replication block. In certain embodiments, the nucleic acid sequence of the replication block is in an inactive form and is converted to an active form by a component of the reaction mixture (for example a component of the enzyme mixture). In certain embodiments of the exogenous nucleic acid sequence above, the replication block is represented by a poly-U sequence, which is inactive as a replication block unless acted on by uracil-DNA glycosylase.

The sequences provided above are exemplary in nature and other exogenous nucleic acid sequences may be provided. Exogenous nucleic acid sequences may be used at 0.1 to 5 μM and primers may be used at 50 to 1000 nM in the methods disclosed herein.

The exogenous nucleic acid sequences to be added to the 5' and/or 3' ends of at least a portion of the cfNA in the sample may be provided in a variety of forms. In one embodiment, the exogenous nucleic acid sequence is a sequence that forms a stem-loop structure and includes a single-stranded loop portion.

In certain embodiments, at least 50%, at least 60%, at least 70% at least 80%, at least 90%, at least 95% or at least 99% of the cfNA molecules in the sample are modified to contain an exogenous nucleic acid sequence at one or both of the 5' and/or 3' ends. In certain embodiments, at least 50%, at least 60%, at least 70% at least 80%, at least 90%, at least 95% or at least 99% of the cfNA molecules in the sample are modified to contain an exogenous nucleic acid sequence at both of the 5' and 3' ends.

The following describes several exemplary approaches to adding the exogenous nucleic acid sequence to the 5' end, 3' end and/or both the 5' end and 3' end of cfNA in a sample. In certain embodiments, the exogenous nucleic acid sequence is added to the 5' and/or 3' ends of the cfNA by an initial replication of the cfNA, which may be primed or initiated by the exogenous nucleic acid sequence. In certain embodiments, at least one strand of the exogenous nucleic acid sequence is ligated to at least one strand of the cfNA at the 5' and/or 3' ends of the cfNA. In certain embodiments, at least one strand of the exogenous nucleic acid sequence is ligated to at least one strand of the cfNA at the 5' and/or 3' ends of the cfNA and at least a portion of the exogenous nucleic acid sequence is replicated by an initial replication, which may be primed or initiated by the cfNA. In the embodiments described herein, one or more of the cfNA in the sample may be ligated together to form a larger cfNA fragment.

In one embodiment, the methods of the present disclosure utilize an initial replication of the cfNA (including, for example, cfDNA) present in a sample by annealing degenerate oligonucleotide primers carrying a universal 5' end primer site. Annealed primers are extended by DNA polymerase, which can then act as new templates for another cycle of primer annealing and extension. As a result, the cfNA (including, for example, cfDNA) in the sample is modified by the addition of an exogenous nucleic acid sequence containing the primer site (in this case by incorporation into the cfNA by the initial replication) and is suitable for exponential amplification prior to analysis, producing an amplifiable cfNA (including, for example, cfDNA) pool. As such the exogenous nucleic acid sequence is added to the 5' and/or 3' ends through the initial replication as the exogenous nucleic acid sequence primes the initial replication. In one embodiment, all enzymatic reactions occur in the original sample without the need for transfer of material (including nucleic acid) or purification of the cfNA (for example, the cfNA is not specifically isolated or purified). In certain embodiments, cfNA fragments in the sample may undergo ligation to produce longer cfNA fragments either before or after the degenerate primers bind to the cfNA sequence. A suitable enzyme mixture for such an embodiment includes, but is not limited to, an enzyme mixture comprising, consisting essentially of or consisting of DNA polymerase I and T4 DNA ligase.

In another embodiment, the methods of the present disclosure apply the concept of molecular cloning to enzymatically add sequence-specific exogenous nucleic acid sequences onto at least a portion of the cfNA (including, for example, cfDNA) in the sample at one or both of the 5'- and 3'-ends, generating a primer site(s) for PCR amplification. In one embodiment, all enzymatic reactions occur in original sample and in a single reaction vessel without the need for transfer of material (including nucleic acid) or purification of the cfNA (for example, the cfNA is not specifically isolated or purified).

In one embodiment of the molecular cloning approach, the exogenous nucleic acid sequence is a sequence that forms a stem-loop structure and includes a single-stranded loop portion and each strand of the exogenous nucleic acid sequence is ligated to each strand of the cfNA at the 5' end and/or the 3' end of at least a portion of the cfNA molecules in the sample such that the modified cfNAs do not have a gap, nick or break in nucleic acid strands between the exogenous nucleic acid sequence and the cfNA sequence. In one embodiment of this approach, the exogenous nucleic acid sequences are ligated directly to the cfNA. The cfNA may be prepared to have blunt ends as discussed herein and the exogenous nucleic acid sequence ligated directly to each strand of the cfNA at the 5' and/or 3' ends. In such an embodiment, the loop portion of the exogenous nucleic acid sequence may be cleaved (or opened up), such as through the use of an enzyme (for example, uracil-DNA glycosylase. A suitable enzyme mixture for such an embodiment includes, but is not limited to, an enzyme mixture comprising, consisting essentially of or consisting of T4 DNA polymerase, ii) T4 DNA ligase; iii) the Klenow fragment of DNA polymerase I; iv) T4 polynucleotide kinase; and v) uracil-DNA glycosylase (optionally containing Nb.BbvC1). Suitable exogenous nucleic acid sequences suitable for such an embodiment include, but are not limited to the sequences of SEQ ID NO: 10 with the primer of SEQ ID NO: 8.

The cfNA may also be prepared to have a tail sequence (for example a 3' overhang), such as a single nucleotide (for example a single adenine residue) or multiple nucleotides (for example a poly-adenine tail); in certain embodiments, the tail is located on one or both of the 5' and/or 3' ends of the cfNA. In certain embodiments, the tail is a single adenine or a poly-adenine tail (such as from 2 to 10 nucleotides in length). In such an embodiment, the loop portion of the exogenous nucleic acid sequence may be cleaved (or opened up), such as through the use of an enzyme (for example, uracil-DNA glycosylase. A suitable enzyme mixture for such an embodiment includes, but is not limited to, an enzyme mixture comprising, consisting essentially of or consisting of T4 DNA polymerase, ii) T4 DNA ligase; iii) the Klenow fragment of DNA polymerase I; iv) T4 polynucleotide kinase; and v) uracil-DNA glycosylase (optionally containing Nb.BbvC1). Suitable exogenous nucleic acid sequences suitable for such an embodiment include, but are not limited to the sequences of SEQ ID NO: 7, (for example, SEQ ID NO: 9), along with the primer of SEQ ID NO: 8.

In another embodiment of the molecular cloning approach, the exogenous nucleic acid sequence is a sequence that forms a stem-loop structure and includes a single-stranded loop portion comprising a complement of a primer site; one strand of the exogenous nucleic acid sequence is ligated to one strand of the cfNA at the 5' end and/or the 3' end of at least a portion of the cfNA molecules in the sample such that the modified cfNAs contains a gap, nick or break in nucleic acid strand at the 5' and/or 3' ends of the cfNA between the terminal 3' OH residue of the cfNA sequence and the 5' OH of the exogenous nucleic acid sequence. In this embodiment, the methods of the present disclosure utilize an initial replication of the exogenous nucleic acid sequences via a nick translation mechanism initiated at the free 3' OH of the cfNA which replicate the exogenous nucleic acid sequence, creating the primer binding site. The 5' phosphate groups may be added by T4 polynucleotide kinase, which replaces the 3' OH originally present on the exogenous nucleic acid sequence with phosphate. A suitable enzyme mixture for such an embodiment includes, but is not limited to, an enzyme mixture comprising, consisting essentially of or consisting of T4 DNA polymerase, T4 DNA ligase, the Klenow fragment of DNA polymerase I, T4 polynucleotide kinase and Nb.BbvC1 (optionally containing uracil-DNA glycosylase). Suitable exogenous nucleic acid sequences suitable for such an embodiment include, but are not limited to the sequences of SEQ ID NO: 5 along with the primer of SEQ ID NO: 6.

In another embodiment of the molecular cloning approach, the exogenous nucleic acid sequence is a sequence that forms a stem-loop structure and includes a single-stranded loop portion comprising a replication block and a complement of a primer site; one strand of the exogenous nucleic acid sequence is ligated to one strand of the cfNA at the 5' end and/or the 3' end of at least a portion of the cfNA molecules in the sample such that the modified cfNAs contain a gap, nick or break in nucleic acid strand at the 5' and/or 3' ends of the cfNA between the terminal 3' OH residue of the cfNA sequence and the 5' OH of the exogenous nucleic acid sequence. In this embodiment, the methods of the present disclosure utilize an initial replication of the exogenous nucleic acid sequences via a nick translation mechanism initiated at the free 3' OH of the cfNA which replicates the exogenous nucleic acid sequence up to the replication block. The 5' overhang created may be filled in using DNA polymerase to create the primer binding site. In certain embodiments, a portion of the palindromic sequence is of the original exogenous nucleic acid sequence is removed from the modified cfNA to prevent formation of the hairpin structure during the subsequent PCR amplification process. Such reaction may be carried out using the single-strand nicking enzymes (for example NbBbv1) and uracil-DNA glycosylase. The 5' phosphate groups may be added by T4 polynucleotide kinase, which replaces the 3' OH originally present on the exogenous nucleic acid sequence with phosphate. A suitable enzyme mixture for such an embodiment includes, but is not limited to, an enzyme mixture comprising, consisting essentially of or consisting of T4 DNA polymerase, T4 DNA ligase, the Klenow fragment of DNA polymerase I, T4 polynucleotide kinase, uracil-DNA glycosylase and Nb.BbvC1. Suitable exogenous nucleic acid sequences suitable for such an embodiment include, but are not limited to, the sequences of SEQ ID NO: 5 along with the primer of SEQ ID NO: 6.

In certain embodiments of the molecular cloning approach, a portion of the palindromic sequence is of the original exogenous nucleic acid sequence (which forms the double-stranded stem portion) is removed from the modified cfNA to prevent formation of the hairpin structure during the subsequent PCR amplification process. Such reaction may be carried out using the single-strand nicking enzyme (for example NbBbv1) and uracil-DNA glycosylase. In certain embodiments of the molecular cloning approach, a portion of the palindromic sequence is not removed.

The amplifiable cfNA pool may then be amplified by any known techniques to produce sufficient quantities of the cfNA for downstream analysis. The product of the amplification reaction is referred to as an analyzable pool of cfNA. In one embodiment, the amplifiable cfNA pool is subject to PCR using the sequence-specific primers for the 3' and/or 5' primer binding sites. In one embodiment, both the 3' and 5' binding sites and their respective primers are used in the amplification. In one embodiment, only one of the 3' or 5' primer binding sites and the respective primer are used for amplification. Any PCR amplification protocol or technique may be used to amplify the amplifiable cfDNA pool.

The PCR amplification may be carried out for a desired number of cycles of amplification to produce a desired yield of cfNA in the analyzable pool of cfNA. In certain embodiments, 10 to 30 cycles of amplification are carried out. In certain embodiments, 12 to 28 cycles of amplification are carried out. In certain embodiments, 15 to 25 cycles of amplification are carried out. In certain embodiments, 17 to 23 cycles of amplification are carried out. In certain embodiments, 18 cycles of amplification are carried out. In certain embodiments, 25 cycles of amplification are carried out.

Cycling conditions for the PCR amplification reaction may be as known in the art and generally comprise steps for template denaturation, primer annealing and primer extension. The initial step denatures the target DNA by heating it to 94° C. or higher for 15 seconds to 4 minutes. In the denaturation process, the strands of DNA separate from one another, producing the necessary single-stranded DNA template for replication by the thermostable polymerase. In the next step of a cycle, the temperature is reduced to approximately 40-65° C. At this temperature, the oligonucleotide primers can form stable associations (anneal) with the denatured target DNA and serve as primers for the polymerase resulting in new template synthesis. This step generally occurs in the range of 65-74° C. for 1-7 minutes. The next cycle begins with a return to 94° C. for denaturation. The particular conditions for PCR amplification may be varied as known in the art and still be useful with the methods of the present disclosure.

In one embodiment, the following PCR amplification conditions are used: i) initial denaturation at 95° C. for 3 min; ii) followed by 25 cycles of denaturation at 94° C. for 15 sec and annealing/extension at 65° C. for 5 min.

In another embodiment, the following PCR amplification conditions are used: i) initial denaturation at 95° C. for 3 min; ii) followed by 18 cycles of denaturation at 94° C. for 15 sec and annealing/extension at 65° C. for 5 min.

The result of the amplification reaction is an analyzable pool of cfDNA molecules.

Exemplary Procedures

Exemplary procedures for carrying out the methods described herein are provided in the Methods section herein and in the Examples.

Analysis of Analyzable Pool of cfDNA

The analyzable pool of cfDNA produced by the methods herein may be analyzed by any method known in the art. Further, any amount of cfNA may be used in the analysis.

In one embodiment, the method of analysis is next generation sequencing (NGS). When NGS is used, the amount of cfNA from the analyzable pool may be varied. In certain embodiments, 1 ng to 50 ng of cfNA in the analyzable pool is used for NGS analysis. In certain embodiments, 1 ng to 10 ng, such as 1 ng to 2 ng, 2 ng to 5 ng, 5 ng to 7 ng or 7 ng to 10 ng, of cfNA in the analyzable pool is used for NGS analysis. In certain embodiments, 10 ng to 25 ng, such as 13 ng to 27 ng, 16 ng to 24 ng or 19 ng to 21 ng, of cfNA in the analyzable pool is used for NGS analysis.

In another embodiment, the method of analysis is NGS and the cfNA sample (for example in the amounts specified above) is taken from a single analyzable pool of cfNA. The cfNA from the analyzable pool of cfNA may be taken in a single sampling or multiple samplings.

In another embodiment, the method of analysis is NGS and the cfNA sample, for example in the amounts specified above, is taken from multiple analyzable pools of cfNA prepared from the same sample. Any number of analyzable pools of cfNA may be sampled, for example from 2 to 10. The cfNA from the analyzable pool of cfNA may be taken in a single sampling or multiple samplings from any analyzable pool of cfNA. Further multiple analyzable pools of cfNA prepared from the same sample may be combined prior to sampling. Any number of analyzable pools of cfNA may be combined (or pooled), for example from 2 to 10. The cfNA from the combined analyzable pool of cfNA may be taken in a single sampling or multiple samplings from the combined analyzable pool of cfNA.

Methods of Using

The present disclosure also provides methods of using the amplifiable pools of cfNA and the analyzable pools of cfNA.

The present disclosure provides methods of analyzing cfNA (including, but not limited to, a cfDNA) in a sample. Certain embodiments of the method are provided below.

In one embodiment, the present disclosure provides a method of analyzing a cell-free nucleic acid, the method comprising the steps of: i) providing an analyzable pool of cfNA molecules by any of the methods described herein and ii) analyzing the analyzable pool of cfNA molecules to determine a characteristic of a cfNA molecule in the analyzable pool of cfNA molecules.

In the methods of analysis, the cfNA may be cfNA. In certain embodiments, the nucleic acid is cfDNA. In certain embodiments, the nucleic acid is double-stranded cfDNA. In certain embodiments, the cfNA is cfRNA, or DNA derived from and which is representative of such cfRNA.

Therefore, in another embodiment, the present disclosure provides a method of analyzing a cfDNA, the method comprising the steps of: i) providing an analyzable pool of cfDNA molecules by any of the methods described herein and ii) analyzing the analyzable pool of cfDNA molecules to determine a characteristic of a cfDNA molecule in the analyzable pool of cfDNA molecules.

In another embodiment, the present disclosure provides a method of analyzing a cfRNA, the method comprising the steps of: i) providing an analyzable pool of cfRNA molecules by any of the methods described herein and ii) analyzing the analyzable pool of cfRNA molecules to determine a characteristic of a cfDNA molecule in the analyzable pool of cfRNA molecules. In certain embodiments, the cfRNA is converted to a DNA representative of the cfRNA and the analyzable pool comprises DNA representative of the cfRNA.

The analyzable pool may be analyzed by any technique known in the art. Suitable techniques include, but are not limited to next generation sequencing (NGS) and PCR-based technologies, such as but not limited to, real-time quantitative PCR, blocker PCR, digital droplet PCR (ddPCR), clamping PCR, ICE-COLD PCR, castPCR, ARMS PCR, BEAMing and the like. The analyzable pool produced according to the methods of the present disclosure provides cfNA of sufficient quantity and quality for use in these and other analytical techniques.

In certain embodiments, the analyzable pool is analyzed to determine at least one characteristic of one or more cfNAs (including cfDNA) in the analyzable pool. The characteristic to be determined may be any characteristic of the cfNA. More than 1 characteristic may be analyzed simultaneously. Representative characteristics include, but are not limited to, chromosomal abnormalities, single nucleotide polymorphisms, gene mutations (such as but not limited to, point mutations, deletions and insertions), methylation pattern and copy number variations; in addition the characteristic may be the presence of an agent (such as but not limited to, a virus, bacteria or fungi). In one embodiment, the characteristic is associated with a disease. In one embodiment, the characteristic is used to determine if the provider of the sample is suffering from a disease. In another embodiment, the characteristic is used to determine if the provider of the sample is at risk for developing a disease. In another embodiment, the characteristic is used to determine the presence of an agent (such as but not limited to, a virus, bacteria or fungi) in the provider of the sample. In another embodiment, the characteristic is used to determine a course of treatment or therapy for a subject. In another embodiment, the characteristic is used to determine if a current course of treatment or therapy is effective.

The ability to analyze the cfNA (including, for example, cfDNA) for a particular characteristic is beneficial in both the diagnostic sense and for determining a therapeutic intervention to treat a disease. As discussed herein, the methods of the present disclosure allow the analysis of cfNA (including, for example, cfDNA) in small sample volumes without the need for purification of the cfNA. Therefore, the application of the methods of the present disclosure to patient care are greatly expanded.

The present disclosure provides for a method of diagnosing a subject as suffering from or at risk for a disease.

In one embodiment, the method comprises the steps of: i) providing an analyzable pool of cfNA molecules by any of the methods described herein; ii) analyzing the analyzable pool of cfNA molecules to determine a characteristic of a cfNA molecule in the analyzable pool of cfNA molecules that is associated with the disease; and iii) determining that the subject is suffering from and/or at risk for the disease based on the presence of the characteristic or determining that the subject is not suffering from and/or at risk for the disease based on the absence of the characteristic.

In another embodiment, the method comprises the steps of: i) providing an analyzable pool of cfDNA molecules by any of the methods described herein; ii) analyzing the analyzable pool of cfDNA molecules to determine a characteristic of a cfDNA molecule in the analyzable pool of cfDNA molecules that is associated with the disease; and iii) determining that the subject is suffering from and/or at risk for the disease based on the presence of the characteristic or determining that the subject is not suffering from and/or at risk for the disease based on the absence of the characteristic.

In another embodiment, the method comprises the steps of: i) providing an analyzable pool of cfRNA molecules by any of the methods described herein; ii) analyzing the analyzable pool of cfRNA molecules to determine a characteristic of a cfRNA molecule in the analyzable pool of cfRNA molecules that is associated with the disease; and iii) determining that the subject is suffering from and/or at risk for the disease based on the presence of the characteristic or determining that the subject is not suffering from and/or at risk for the disease based on the absence of the characteristic. In certain embodiments, the cfRNA is converted to DNA representative of the cfRNA and the analyzable pool comprises DNA representative of the cfRNA.

A number of characteristics of the cfNA may be determined using a variety of methods as discussed herein. As exemplary application of the above method, if a subject is suspected of suffering from advanced metastatic colon cancer, the analyzable pool may be analyzed for a characteristic associated with advanced metastatic colon cancer (for example mutations in one or more of the KRAS, BRAF, NRAS and PIK3CA genes). If the characteristic is present in the analyzable pool (a mutation in one or more of the KRAS, BRAF, NRAS and PIK3CA genes) the subject is determined to be suffering from or at risk for colon cancer.

The present disclosure provides for a method of determining a therapeutic intervention for a subject suffering from a disease.

In one embodiment, the method comprises the steps of: i) providing an analyzable pool of cfNA molecules by any of the methods described herein ii) analyzing the analyzable pool of cfNA molecules to determine a characteristic of a cfNA molecule in the analyzable pool of cfNA molecules that is associated with the disease; and iii) determining the therapeutic intervention based on the characteristic determined.

In another embodiment, the method comprises the steps of: i) providing an analyzable pool of cfDNA molecules by any of the methods described herein ii) analyzing the analyzable pool of cfDNA molecules to determine a characteristic of a cfDNA molecule in the analyzable pool of cfDNA molecules that is associated with the disease; and iii) determining the therapeutic intervention based on the characteristic determined.

In another embodiment, the method comprises the steps of: i) providing an analyzable pool of cfRNA molecules by any of the methods described herein ii) analyzing the analyzable pool of cfRNA molecules to determine a characteristic of a cfRNA molecule in the analyzable pool of cfRNA molecules that is associated with the disease; and iii) determining the therapeutic intervention based on the characteristic determined. In certain embodiments, the cfRNA is converted to DNA representative of the cfRNA and the analyzable pool comprises DNA representative of the cfRNA.

A number of characteristics of the cfNA may be determined using a variety of methods as discussed herein. As an exemplary application of the method of determining a therapeutic intervention, the colon cancer example is considered again. As discussed, mutations in one or more of the KRAS, BRAF, NRAS and PIK3CA genes are indicative of colon cancer. However, depending on the particular aberrations present, the therapeutic intervention needed for the most efficacious treatment is different. If the characteristic(s) determined have no mutations in the KRAS, BRAF, NRAS and PIK3CA genes, then therapy with anti-EGFR antibodies such as cetuximab and panitumumab (which is the first line treatment option according to NCCN and ASCO guidelines) may be determined as an appropriate therapy. However, if the characteristic determined is the presence of a mutation in the KRAS, BRAF, NRAS and PIK3CA genes, then therapy with anti-EGFR antibodies is not recommended as mutations in the KRAS, BRAF, NRAS and PIK3CA genes indicate non-responsiveness to anti-EGFR antibody therapy.

The present disclosure also provides for a method of monitoring the treatment of a subject that has been diagnosed with a disease and is undergoing treatment with a therapeutic regimen for the treatment of the disease.

In one embodiment, the method comprises the steps of: i) providing an analyzable pool of cfNA molecules by any of the methods described herein, such as the first to fourth aspects; ii) analyzing the analyzable pool of cfNA molecules to determine a characteristic of a cfNA molecule in the analyzable pool of cfNA molecules that is associated with the disease; iii) determining if the determined characteristic is compatible with the current therapeutic treatment regimen; iv) altering the therapeutic regimen if the determined characteristic indicates the therapeutic regimen is contraindicated or not recommended or continuing the therapeutic regimen if the determined characteristics indicates the therapeutic regimen continues to be recommended; and vi) optionally repeating steps i) to iv) to monitor the therapeutic intervention at desired time intervals.

In another embodiment, the method comprises the steps of: i) providing an analyzable pool of cfDNA molecules by any of the methods described herein, such as the first to fourth aspects; ii) analyzing the analyzable pool of cfDNA molecules to determine a characteristic of a cfDNA molecule in the analyzable pool of cfDNA molecules that is associated with the disease; iii) determining if the determined characteristic is compatible with the current therapeutic treatment regimen; iv) altering the therapeutic regimen if the determined characteristic indicates the therapeutic regimen is contraindicated or not recommended or continuing the therapeutic regimen if the determined characteristics indicates the therapeutic regimen continues to be recommended; and vi) optionally repeating steps i) to iv) to monitor the therapeutic intervention at desired time intervals.

In another embodiment, the method comprises the steps of: i) providing an analyzable pool of cfRNA molecules by any of the methods described herein, such as the first to fourth aspects; ii) analyzing the analyzable pool of cfRNA molecules to determine a characteristic of a cfRNA molecule in the analyzable pool of cfRNA molecules that is associated with the disease; iii) determining if the determined characteristic is compatible with the current therapeutic treatment regimen; iv) altering the therapeutic regimen if the determined characteristic indicates the therapeutic regimen is contraindicated or not recommended or continuing the therapeutic regimen if the determined characteristics indicates the therapeutic regimen continues to be recommended; and vi) optionally repeating steps i) to iv) to monitor the therapeutic intervention at desired time intervals. In certain embodiments, the cfRNA is converted to DNA representative of the cfRNA and the analyzable pool comprises DNA representative of the cfRNA.

A number of characteristics of the cfNA may be determined using a variety of methods as discussed herein. The methods of the present disclosure provide for monitoring a subject by determining a characteristic of a cfNA in a sample, determining if the determined characteristic is compatible with the current therapeutic treatment regimen and making a treatment decision (for example altering the therapeutic regimen if a characteristic determined indicates the therapeutic regimen is contraindicated or not recommended or continuing the therapeutic regimen if the characteristics determined indicate the therapeutic regimen continues to be recommended) based on the characteristic(s) determined. Consider a subject that has been diagnosed with colon cancer and determined to be eligible for anti-EFGR antibody treatment after an initial screen. As discussed above, mutations in one or more of the KRAS, BRAF, NRAS and PIK3CA genes indicate that anti-EGFR antibody therapy may not be appropriate. If a characteristic determined is a mutation in one or more of the KRAS, BRAF, NRAS and PIK3CA genes while anti-EGFR antibody treatment is continuing, then the decision may be made to stop treatment with anti-EGFR antibodies and initiate a new treatment regimen.

In another embodiment, the characteristic may be a characteristic indicating the development of drug resistance in a tumor cell that may impact the current treatment for the cancer. If a drug resistance phenotype is determined, then the treatment regimen can be revised and altered if needed. In still another embodiment, the characteristic may be indicative of the clonal evolution of the tumor (for example, the appearance of new characteristics or the disappearance of previously determined characteristics). Again, the treatment regimen can be revised and altered if needed. In still another embodiment, the characteristic may be one indicative of tumor metastasis. If such a characteristic is determined, then the treatment regimen may be modified accordingly if desired or a new treatment regimen initiated.

The present disclosure also provides for a method of monitoring a subject.

In one embodiment, the method comprises the steps of: i) providing an analyzable pool of cfNA molecules by any of the methods described herein, such as the first to fourth aspects; ii) analyzing the analyzable pool of cfNA molecules to determine a characteristic of a cfNA molecule in the analyzable pool of cfNA molecules that is associated with the disease; and iii) determining if the subject is in need of treatment based on the characteristic determined.

In another embodiment, the method comprises the steps of: i) providing an analyzable pool of cfDNA molecules by any of the methods described herein, such as the first to fourth aspects; ii) analyzing the analyzable pool of cfDNA molecules to determine a characteristic of a cfDNA molecule in the analyzable pool of cfDNA molecules that is associated with the disease; and iii) determining if the subject is in need of treatment based on the characteristic determined.

In another embodiment, the method comprises the steps of: i) providing an analyzable pool of cfRNA molecules by any of the methods described herein, such as the first to fourth aspects; ii) analyzing the analyzable pool of cfRNA molecules to determine a characteristic of a cfRNA molecule in the analyzable pool of cfRNA molecules that is associated with the disease; and iii) determining if the subject is in need of treatment based on the characteristic determined. In certain embodiments, the cfRNA is converted to DNA representative of the cfRNA and the analyzable pool comprises DNA representative of the cfRNA.

A number of characteristics of the cfNA may be determined using a variety of methods as discussed herein. For example, again consider the colon cancer example. If a subject is currently in remission, the subject can be monitored using the methods of the present disclosure. If a characteristic is determined that indicates a re-occurrence of colon cancer, a therapeutic intervention can be re-initiated. The therapeutic intervention may be guided, at least in part, by the characteristic determined.

Method of Quantification of cfNA in a Sample

The methods of the present disclosure also allow for the determination of the original concentration or amount of cfNA in a sample. Current methods for quantification of the amount of cfDNA in samples is subject to extreme variability due to difficulties in purifying cfDNA from a sample (which results in loss of cfDNA from the sample) and the low concentration of cfDNA in the sample. A robust and efficient method of quantifying the concentration of cfDNA in a sample is desirable and would have important clinical applications. For example, high levels of cfDNA have been suggested to be predictive of transplantation rejection, post-traumatic complications after injury (including organ failure), risk stratification in ischemic stroke, the severity of sepsis and other conditions. The CGD method described is a linear amplification process. Therefore, it is possible to quantify the concentration of cfDNA in an original sample by reference to a standard curve prepared using known quantities of DNA as the input (in place of the sample containing cfDNA). For example, a standard curve may be established using DNA, preferably purified DNA, (for example, using serial concentrations of 0, 0.001, 0.005, 0.01, 0.025, 0.05, 0.1, 0.25, 0.5, and 1 ng/μL) as inputs in the CGD method and determining the yield of amplified DNA at each concentration to prepare the standard curve. The yield of amplified cfDNA resulting from the cfDNA in a sample is then determined and the original concentration of cfDNA in the sample determined by reference to the standard curve.

In one embodiment, the method comprises the steps of: i) providing an amplifiable cfNA pool by any of the methods described herein; ii) amplifying the amplifiable cfNA pool to produce an amplified pool of cfNA molecules; iii) determining the concentration of cfNA in the amplified pool of cfNA; and iv) comparing the concentration of cfNA determined to a standard curve to determine the concentration of cfNA in the sample.

In certain embodiments, the standard curve is prepared using the same methods as used to prepare the amplified pool of cfNA. In certain embodiments, the standard curve is prepared using purified DNA. In certain embodiments, the standard curve is prepared contemporaneously with the amplified pool of cfNA.

Kits

The present disclosure also provides for kits comprising one or more of the reagents and/or reaction solutions required for the methods described. In one embodiment, the present disclosure provides a kit comprising at least a portion of the components and reagents required to carry out the methods of the present disclosure.

In one embodiment, the kit, which may be housed in a suitable container or reaction vessel in which a reaction is carried out, comprises, consists of or consists essentially of: at least one exogenous nucleic acid sequence (i.e., an adaptor); a reaction solution suitable for ligating an exogenous nucleic acid sequence to a cfNA; and optionally an enzyme mixture suitable for use with the reaction solution to produce an amplifiable pool of cfNA.

In another embodiment, the kit, which may be housed in a suitable container or reaction vessel in which a reaction is carried out, comprises, consists of or consists essentially of: a reaction solution suitable for ligating an exogenous nucleic acid sequence to a cfNA; an enzyme mixture suitable for use with the reaction solution to produce an amplifiable pool of cfNA; and optionally at least one exogenous nucleic acid sequence (i.e., an adaptor).

In another embodiment, the kit, which may be housed in a suitable container or reaction vessel in which a reaction is carried out, comprises, consists of or consists essentially of: a reaction solution suitable for ligating an exogenous nucleic acid sequence to a cfNA; an enzyme mixture suitable for use with the reaction solution to produce an amplifiable pool of cfNA; and at least one exogenous nucleic acid sequence (i.e., an adaptor).

Any of the kits above may further comprise one or more of the following: a second reaction solution suitable for amplification of the amplifiable cfNA pool; at least one primer for use with the exogenous nucleic acid sequence; a second enzyme mixture for use with the second reaction solution for amplification of the amplifiable cfNA pool to produce the analyzable pool of cfNA and instructions for carrying out the method. In certain embodiments, any of the kits above contain all of the recited additional components.

In one embodiment, the kit may be stored at −20° C. In another embodiment, the kit may be stored at 4° C. The length of storage may be from days to months to years, particularly when stored at −20° C.

In one embodiment, the kit is provided in a multi-well plate format, such as a 96-well plate.

In certain embodiments, the enzyme mixture suitable for use with the reaction solution to produce an amplifiable pool of cfNA may contain the following activities:
1) a polymerase having a 5'-3' polymerase activity and a 3'-5' exonuclease activity and ii) a ligase; 2) a polymerase having a 5'-3' polymerase activity and a 3'-5' exonuclease activity, ii) a ligase and iii) a polynucleotide kinase;

3) a polymerase having a 5'-3' polymerase activity and a 3'-5' exonuclease activity, ii) a ligase, iii) a polynucleotide kinase and iv) a uracil-DNA glycosylase activity;
4) a polymerase having a 5'-3' polymerase activity and a 3'-5' exonuclease activity, ii) a ligase, iii) a polynucleotide kinase, iv) a uracil-DNA glycosylase activity and v) a nucleic acid nicking enzyme activity;
5) a polymerase having a 5'-3' polymerase activity and a 3'-5' exonuclease activity, ii) a ligase, iii) a polynucleotide kinase, iv) a uracil-DNA glycosylase activity, v) a nucleic acid nicking enzyme activity and vi) a nucleic acid binding protein.

In certain embodiments, the enzyme mixture suitable for use with the reaction solution to produce an amplifiable pool of cfNA may comprise following components:
1) a DNA polymerase having a 5'-3' polymerase activity and a 3'-5' exonuclease activity and ii) a DNA ligase;
2) a DNA polymerase having a 5'-3' polymerase activity and a 3'-5' exonuclease activity, ii) a ligase and iii) a DNA polynucleotide kinase;
3) a DNA polymerase having a 5'-3' polymerase activity and a 3'-5' exonuclease activity, ii) a DNA ligase, iii) a DNA polynucleotide kinase and iv) a uracil-DNA glycosylase activity;
4) a DNA polymerase having a 5'-3' polymerase activity and a 3'-5' exonuclease activity, ii) a DNA ligase, iii) a DNA polynucleotide kinase, iv) a uracil-DNA glycosylase activity and v) a single-strand DNA nucleic acid nicking enzyme activity;
5) a DNA polymerase having a 5'-3' polymerase activity and a 3'-5' exonuclease activity, ii) a DNA ligase, iii) a DNA polynucleotide kinase, iv) a uracil-DNA glycosylase activity, v) a single-strand DNA nucleic acid nicking enzyme activity and vi) a single-stranded DNA binding protein.

In certain embodiments, the enzyme mixture suitable for use with the reaction solution to produce an amplifiable pool of cfNA may comprise following components:
1) T4 DNA polymerase and ii) T4 DNA ligase or the Klenow fragment of DNA polymerase I and ii) T4 DNA ligase;
2) T4 DNA polymerase, ii) T4 DNA ligase; and iii) the Klenow fragment of DNA polymerase I
3) T4 DNA polymerase, ii) T4 DNA ligase; iii) the Klenow fragment of DNA polymerase I; and iv) T4 polynucleotide kinase;
4) T4 DNA polymerase, ii) T4 DNA ligase; iii) the Klenow fragment of DNA polymerase I; iv) T4 polynucleotide kinase; and v) uracil-DNA glycosylase; or
5) T4 DNA polymerase, ii) T4 DNA ligase; iii) the Klenow fragment of DNA polymerase I; iv) T4 polynucleotide kinase; v) uracil-DNA glycosylase and Nb.BbvC1.

Any of the foregoing may further comprise a single-stranded binding protein (such as for example, E. coli single-stranded binding protein).

In certain embodiments, the enzyme mixture suitable for use with the reaction solution to produce an amplifiable pool of cfNA comprises T4 DNA polymerase, T4 DNA ligase; the Klenow fragment of DNA polymerase I, T4 polynucleotide kinase, uracil-DNA glycosylase and Nb.BbvC1. In certain embodiments, the enzyme mixture suitable for use with the reaction solution to produce an amplifiable pool of cfNA comprises the Klenow fragment of DNA polymerase I and T4 DNA ligase.

The concentration of the various enzymes that may be used in the methods disclosed herein may be varied. In one embodiment, the enzymes are used in the following concentration ranges: T4 DNA polymerase from 2-15 U, the Klenow fragment from 2-20 U, T4 DNA ligase from 100-1,000 U, T4 polynucleotide kinase from 5-20 U, Nb.BbvC1 from 5-20 U, and uracil-DNA glycosylase from 1-6 U; E. coli single-strand binding protein may be present from 50-500 ng.

In certain embodiments, the enzyme mixture suitable for use with the reaction solution to produce an amplifiable pool of cfNA comprises the enzyme mixtures described in Example 12 herein.

A variety of buffer/reaction solutions may be used in the methods of the present disclosure as is known in the art. In certain embodiments, the reaction solution comprises 20-75 mM potassium acetate, 10-100 mM Tris-acetate (pH 7.9 at 25° C.), 1-30 mM magnesium acetate, 0.1-20 mM DTT, 5 to 100 µM dNTP, 0.5-2 mM of ATP, and 100-400 ug/mL BSA. In certain embodiments, the reaction solution comprises 20-75 mM NaCl, 10-100 mM Tris-Cl, pH 7.0-8.0, 1-30 mM MgCl$_2$, 0.1-20 mM DTT 5 to 100 µM dNTP and 0.5-2 mM of ATP.

In certain embodiments, the reaction solution for use with the enzyme mixture is one described in Example 13 herein.

Methods

Preparation of Plasma cfDNA

Blood was collected in EDTA-containing tubes (Becton Dickinson, Franklin Lakes, N.J.) and was centrifuged at 2500 rpm for 20 minutes. Further centrifugation (10,000 rpm for 10 minutes) may be employed if required to remove residual debris (for example in samples that have been stored). Plasma was transferred to cryovials, being careful to avoid the buffy coat, and was stored at −80° C. until further analysis. cfDNA was prepared from 20 µL and 200 µL of plasma sample using the cfDNA enrichment and recovery technology described herein (referred to as the CGD method) and QIAamp Circulating Nucleic Acid kit (Qiagen, Valencia, Calif.; used according to manufacturer's instructions), respectively.

Preparation of cfDNA from Urine

Unless otherwise stated, circulating cfDNA was prepared from directly from 10-20 µL of unprocessed, undiluted urine sample using the CGD method.

ISA of cfDNA

In the examples described herein, the CGD method is performed for ISA of cfDNA using several variations. Certain Examples provide comparisons of various protocols for optimization purposes and the methods by which the CGD method is performed is provided in each such example.

The following description are not intended to limit the general application of the CGD method as described and are provided as exemplary protocols for carrying out the methods described herein. The methods described are performed in a suitable container or reaction vessel, such as for example, a PCR tube or multiwall strip/plate.

Protocol A

1. To sample (for example, 20 µL plasma, serum, urine, saliva or CSF) the sample is diluted with 1×PBS (80 µL for a 20 µL sample volume) was added and the sample optionally mixed.
2. To 10 µL of sample from step 1, 1 µL of 10×TE Buffer was added and the sample was heated at 95° C. for 4 minutes.
4. The sample was immediately cooled on ice and the sample centrifuged briefly to consolidate the contents.
5. 2 µL of master mix (final concentration in reaction 40 µM of dNTPs, 2 µM each of adaptor molecules; i.e., the exogenous nucleic acid sequence) and 2 µL of universal buffer (final concentration in reaction 50 mM NaCl, 25 mM Tris-Cl, pH 7.0-8.0, 10 mM Mg$_2$Cl, 2.5 mM DTT and 1 mM ATP) was added to each sample.

```
                                              (SEQ ID NO: 1)
5'-(N₆₋₁₀)ATTAACCCTCACTAAAG(N₃₋₆)-3'

(SEQ ID NO: 2)
5'-(N₆₋₁₀)TAATACGACTCACTATAGGG(N₃₋₆)-3'
```

6. Samples were vortexed thoroughly, centrifuged briefly and heated at 95° C. for 2 minutes. 7. The samples were cooled on ice, consolidated by centrifugation, and returned to ice.

8. 1 µL of enzyme mixture comprising E. coli DNA polymerase (Klenow fragment) and T4 DNA ligase was added to each sample (final concentration 5 U of polymerase and 100 U ligase) and the samples were vortexed thoroughly and centrifuged briefly.

9. The samples were placed in a thermal cycler and incubated as follows:
   16° C. for 20 minutes
   24° C. for 20 minutes
   37° C. for 20 minutes
   75° C. for 5 minutes
   4° C. hold 10. After removal from the thermal cycler, the samples were centrifuged briefly. The samples were either stored at −20° C. (for up to three days) and further processed as described below or immediately further processed as described below.

11. For amplification of the modified cfNA containing the adaptor nucleic acid, the following reagents were added to each sample from step 10:
   7.5 µL of 10× master mix (final concentration in reaction 40 µM of dNTPs and 500 nM of primer having the sequence of SEQ ID NOS: 3 and 4);
   47.5 µL of water (molecular biology grade); and
   5 µL of high-fidelity DNA Polymerase

```
      5' Primer
                                              (SEQ ID NO: 3)
      5'-ATTAACCCTCACTAAAG-3'

3' Primer:
                                              (SEQ ID NO: 4)
      5'-TAATACGACTCACTATAGGG-3'
```

13. Each sample was vortexed thoroughly, briefly centrifuged, placed in a thermal cycler and incubated as follows:
   Initial Denaturation 95° C. for 3 minutes
   Perform 25 cycles as follows:
   Denature 94° C. for 15 seconds
   Anneal/Extend 65° C. for 5 minutes After cycling was complete, the samples were maintained at 4° C. and the amplified cfNA subject to analysis as described herein or stored at −20° C. until subject to analysis as described herein.

Protocol B

1. To 20 µL of sample (for example, plasma, serum, urine or CSF) 80 µL of 1×PBS was added and the sample optionally mixed.

2. To 10 µL of sample from step 1, 1 µL of 10×TE Buffer (100 mMTris0HCL, pH 8.0, and 10 mM EDTA) was added and the sample was heated at 95° C. for 4 minutes.

4. The sample was immediately cooled on ice and the sample centrifuged briefly to consolidate the contents.

5. 2 µL of CG1 buffer (final concentration: 2 µM adaptor molecule of SEQ ID NO: 5 (in nuclease free water); i.e., the exogenous nucleic acid sequence) and 1 µL of CG2 buffer (final concentration: 50 mM potassium acetate, 20 mM tris-acetate, pH 7.9, 10 mM magnesium acetate, 1 mM DTT, 1 mM ATP, 40 µM dNTP and 200 µg/ml BSA) was added to each sample.

```
                                              (SEQ ID NO: 5)
5'-
OHTGTGTTGGGTGTGGUUUUUATTTAATACGACTCACTATAGACCCTCAG
CACCACCACACCCAACACA-3'
```

6. Samples were vortexed thoroughly, centrifuged briefly and heated at 95° C. for 2 minutes.

7. The samples were cooled on ice, consolidated by centrifugation, and returned to ice.

8. 1 µL of enzyme mixture comprising of Klenow fragment of T4 DNA polymerase, T4 DNA ligase, E. coli DNA polymerase I, T4 polynucleotide kinase, uracil-DNA glycosylase (UDG), Nb.BbvC1 and E. coli single-strand binding protein was added to each sample (final concentration 5 U T4 DNA polymerase, 800 U T4 DNA ligase, 12.5 U Klenow fragment, 12.5 U T4 polynucleotide kinase, 3.75 U uracil-DNA glycosylase and 120 ng single-strand binding protein) and the samples were vortexed thoroughly and centrifuged briefly.

9. The samples were placed in a thermal cycler and incubated as follows:
   16° C. for 20 minutes
   24° C. for 20 minutes
   37° C. for 20 minutes
   75° C. for 5 minutes
   4° C. hold 10. After removal from the thermal cycler, the samples were centrifuged briefly. The samples were either stored at −20° C. (for up to three days) and further processed as described below or immediately further processed as described below.

11. For amplification of the modified cfNA containing the adaptor nucleic acid, the following reagents were added to each sample from step 10:
   7.5 µL of 10× master mix (40 µM of dNTPs and 500 nM of primer having the sequence of SEQ ID NO: 6);
   47.5 µL of water (molecular biology grade); and
   5 µL of high-fidelity DNA Polymerase

```
                                              (SEQ ID NO: 6)
      5'-ACTCACTATAGACCCTCAGCACCAC-3'
```

13. Each sample was vortexed thoroughly, briefly centrifuged, placed in a thermal cycler and incubated as follows:
   Initial Denaturation 95° C. for 3 minutes
   Perform 25 cycles as follows:
   Denature 94° C. for 15 seconds
   Anneal/Extend 65° C. for 5 minutes After cycling was complete, the samples were maintained at 4° C. and the amplified cfNA subject to analysis as described herein or stored at −20° C. until subject to analysis as described herein.

ISA of cfRNA

The following description is an exemplary method of performing ISA on cfRNA. This description is not intended to limit the general application of the CGD method as described and are provided as an exemplary protocols for carrying out the methods described herein. The methods described are performed in a suitable container or reaction vessel, such as for example, a PCR tube or multiwall strip/plate.

1. Take 10 µL diluted plasma (1:5) heated at 95° C. for 2 min to inactivate endogenous nucleases, dissociate DNA complexes, and fragment/denature cfDNA;

2. Add 1 µL of DNase I reaction buffer (final concentration 10 mM Tris-HCl, 2.5 mM $MgCl_2$, 0.5 mM $CaCl_2$) pH 7.6) and 2 units of DNase I, mix thoroughly and incubate at 37° C. for 30 minutes;
3. Add 1 µL of 0.5 M EDTA (to a final concentration of 5 mM);
4. Heat inactivate at 85° C. for 15 minutes;
5. Perform reverse transcription and cDNA synthesis (for example using Protoscript II kit from New England BioLabs, Ipswich, Mass.). To 11 µL of the above DNase I-treated sample, add 3 µL 5× first strand synthesis reaction buffer and 1 µL random primers; Incubate the sample at 94° C. for 15 min, transfer the tube to ice; Add 0.5 µL murine RNase inhibitor (20 U) and 1 µL Reverse Transcriptase, and water to make up final volume to 20 µL; and incubate the sample in a preheated thermal cycler as follows: 10 minutes at 25° C.; 15 minutes at 42° C.; 15 minutes at 70° C.; and hold at 4° C.;
6. Perform second strand synthesis (for example using NEBNext Second Strand Synthesis Module from New England BioLabs, Ipswich, Mass.). Add the following reagents to the to the reaction (20 µl): Nuclease-free water 48 µl; synthesis reaction buffer 8 µl; synthesis enzyme mix 4 µl (total volume 80 µl); mix thoroughly and incubate in a thermal cycler for 1 hour at 16° C., with heated lid set at ≤40° C.
7. Purify the double-stranded cDNA using Agencourt AMPure XP beads (Beckman Coulter, Brea, Calif.).
8. Proceed to step 5 of the ISA protocol for cfDNA (for example, protocol A or protocol B).

Real-Time PCR

Amplifiability of cfDNA was carried out in duplicate for each sample using TaqMan real-time quantitative PCR, with primers designed specific for KRAS, BRAF, PIK3CA, and NRAS genes (Life Technologies, Carlsbad, Calif.). The amplification plots and Ct values were generated by built-in software (QuantStudio 12K instrument, Life Technologies, Carlsbad, Calif.). Appropriate blanks and positive controls were included in each run to control the accuracy of PCR reaction.

Quantification of Plasma cfNA

Quantification of cfNA was performed using the Qubit 2.0 Fluorometer together with dsDNA BR and HS assay kits (Life Technologies, Carlsbad, Calif.). Analysis were preformed according to manufacturer's instruction.

Deep Targeted Sequencing and Data Analysis by Ion Torrent NGS

Briefly, the targeted sequencing libraries were generated using the Ion AmpliSeq Library kit 2.0 and Cancer Hotspot Panel v2 according to the manufacturer's instructions (Life Technologies, Carlsbad, Calif.). This test panel is designed to target 2,855 mutations in the following 50 key cancer genes: ABL1, AKT1, ALK, APC, ATM, BRAF, CDH1, CDKN2A, CSF1R, CTNNB1, EGFR, ERBB2, ERBB4, EZH2, FBXW7, FGFR1, FGFR2, FGFR3, FLT3, GNAQ, GNAS, GNA11, HNF1A, HRAS, IDH1, IDH2, JAK2, JAK3, KDR, KIT, KRAS, MET, MLH1, MPL, NOTCH1, NPM1, NRAS, PDGFRA, PIK3CA, PTEN, PTPN11, RB1, RET, SMAD4, SMARCB1, SMO, SRC, STK11, TP53, and VHL. The full list of mutations can be found at (http://path.upmc.edu/divisions/map/). Mutation details can be obtained from the Catalogue of Somatic Mutations in Cancer (COSMIC) database with the corresponding COSMIC ID http://cancer.sanger.ac.uk/cancergenome/projects/cosmic/. DNA sequences used as references for this panel of genes can be found at http://www.ncbi.nlm.nih.gov/refseq/rsg/. The mutation nomenclature is based on the convention recommended by the Human Genome Variation Society (http://www.hgvs.org/mutnomen/).

The starting material consisted of 1-20 ng cfDNA prepared using the CGD method or by other methods (for example, the QIAamp kit). Each sample was analyzed for the entire 50-gene panel interrogating a total of approximately 2,800 mutations. The primers used for library amplification were than partially digested by Pfu enzyme, and followed by ligation with corresponding barcoded adapters and purified using Ampure Beads. The quality of the libraries was assessed using QuantStudio 6 real-time PCR instrument. Twenty picomoles of each library were analyzed on the Ion Chef system for emulsion PCR to clonally amplify sequencing templates. Based on the number of samples analyzed, chip 314, 316 or 318 was used. Deep sequencing was performed on Ion Torrent PGM with coverage ranges of 1000-4000×. Sequencing data were analyzed by the Variant Caller 4.0 software using the somatic high stringency parameters and the targeted and hotspot pipelines. All the variants identified were further confirmed by analyzing the data through GenePool (Station X, San Francisco, Calif.).

EXAMPLES

Example 1—cfDNA Recovery

To demonstrate the superior properties of the CGD method, cfDNA was prepared using the CGD method and with a commercially available cfDNA purification kit (QIAamp Circulating Nucleic Acid kit; Qiagen, Valencia, Calif.). cfDNA from plasma (20 µL) and urine (10 µL) samples were prepare as described using protocol A. The amplifiable cfDNA pool was subject to PCR amplification as described in protocol A. cfDNA was prepared from plasma (200 µL) samples using the QIAamp kit (used according to manufacturer's instructions). cfDNA was prepared from plasma samples of 17 cancer patients; urine samples were from healthy subjects. cfDNA was quantified by the fluorescent Qubit dsDNA BR or HS assay, and Taqman real-time PCR analysis on the KRAS, BRAF, PIK3CA, and NRAS genes (only on plasma samples). Further, NGS analysis was applied to detect mutations in the plasma sample sets (only on plasma samples).

As shown in Table 1, the CGD method provided significantly more cfDNA than the QIAamp kit as determined by Qubit measurement. The average concentration of cfDNA observed using the CGD method was 92.5 ng/µL compared to 0.42 ng/µL using the QIAamp kit (n=17, P<0.0001). This enhanced recovery is more pronounced when the input sample volumes are considered. For the CGD method, 20 µL of plasma sample was used as compared to 200 µL of plasma sample with the QIAamp kit. The CGD method still provided far superior results, even at reduced sample volumes.

cfDNA was also recovered from urine samples using the CGD method and quantitated by Qubit measurement. The average concentration of cfDNA obtained using the CGD method was 40.9 ng/µL (N=6) (4.52 ng/ml to 80.4 ng/ml.). As for plasma samples, the CGD method showed effective preparation of cfDNA from urine samples. The results are shown in Table 1

TABLE 1

|  | CGD method | QIAamp kit |
|---|---|---|
| Plasma (n = 17) | 92.5 | 0.42 |
| Urine (n = 6) | 40.9 |  |

The higher output of cfDNA obtained with the CGD method was also revealed by agarose gel electrophoresis. Selected cfDNA samples prepared from plasma and urine samples by the CGD method were subject to agarose gel electrophoresis (2%) and visualized using ethidium bromide. cfDNA obtained from plasma (FIG. 1B) and urine (FIG. 1C) prepared by the CGD method showed strong DNA intensities.

In FIG. 1B, samples analyzed included cfDNA extracted from 7 frozen plasma samples and three fresh plasma samples. Lanes 1-4 were clinical plasma samples from subject diagnosed with or suspected of having cancer, lane 5 was fresh plasma from a healthy subject spiked with plasma from sample 4. Lanes 6-8 were frozen plasma samples from healthy subjects and lanes 9-10 were fresh plasma samples from healthy subject. Fractionation of plasma cfDNA prepared using the CGD method revealed consistent size distribution between 100- and 500-bp and showed intense staining.

In FIG. 1C, cfDNA recovered from 10 µL of urine was subject to agarose gel electrophoresis (2%) and visualized using ethidium bromide. The samples analyzed were from urine samples from 6 healthy individuals (lanes 1-6) with a plasma sample as a positive control (lane 7). As seen for plasma samples, fractionation of cfDNA obtained from urine samples using the CGD method revealed consistent size distribution between 100- and 500-bp by the CGD method and shoed intense staining.

The above results demonstrate that the CGD method provides excellent cfDNA preparations in high quantities from a variety of sample types. Furthermore, the CGD method was superior to the prior art methods tested.

Example 2—Amplifiability of cfDNA

The amplifiability of cfDNA prepared from plasma samples as described in Example 1 by the CGD method and using the QIAamp kit was then examined by TaqMan quantitative real-time PCR (qPCR) on four proto-oncogenes (KRAS, BRAF, PIK3CA and NRAS) to evaluate the quality of the analyzable pool of cfDNA produced. Plasma samples prepared as described in Example 1 and subject to qPCR analysis.

The qPCR technique involves continuous monitoring of the progress of amplification and permits target quantification. As expected, amplification plots of KRAS from cfDNA prepared using the CGD method and the QIAamp kit showed ranges of threshold cycle (Ct) values between 17-24 and 28-33 for cfDNA prepared using the CGD method and the QIAamp kit, respectively (FIG. 2). In all samples, KRAS was amplified indicating the presence of sufficient cfDNA in the plasma samples. However, comparison of the Ct values indicates the CGD method provided at least 100-fold more analyzable cfDNA than the QIAamp kit (ΔCt>7).

It was next determined whether similar differences existed with measurements made on the 3 other genes—BRAF, PIK3 CA, and NRAS. Plasma samples were prepared as described in Example 1. The results are shown in FIGS. 3A-3C for BRAF, PIK3CA and NRAS, respectively. Amplification plots from cfDNA prepared using the CGD method showed lower Ct values as compared to cfDNA prepared using the QIAamp kit. The difference was observed across all three genes. The magnitude of ΔCt is in line with that of KRAS.

A summary of the key characteristic for these experiments are shown in Table 2.

TABLE 2

Comparison of cfDNA sample preparation methods

| Key Characteristics | CGD Method | QIAamp Method |
|---|---|---|
| Yield, Range (ng/µL), n = 12 | 97.30-132.25 | 0.43-26.27 |
| Yield, Mean ± SD (ng/µL), n = 1 | 108.46 ± 11.17 | 4.58 ± 24.80 |
| Yield, % CV, n = 12 | 10.30 | 541.48 |
| Average Ct, KRAS, n = 12 | 22.7 | 33.2 |
| Average Ct, BRAF, n = 12 | 20.6 | 30.8 |
| Average Ct, PIK3CA, n = 12 | 19.6 | 31.2 |
| Average Ct, NRAS, n = 12 | 18.2 | 27.8 |

Table Abbreviations:
Ct: Cycle threshold

The above results demonstrate that the CGD method provides an analyzable pool of cfDNA of high quality suitable for further analysis. Furthermore, the CGD method was superior to the prior art method tested.

Example 3—Next Generation Sequencing

A further evaluation of the cfDNA prepared from the CGD method and the QIAamp kit was performed using next-generation sequencing (NGS) analysis. cfDNA was prepared as described in Example 1. NGS analysis was performed as described above.

1 to 10 ng of cfDNA prepared using the CGD method and using the QIAamp kit were analyzed for the entire 50-gene panel interrogating a total of approximately 2,800 mutations (Cancer Hotspot Panel v2, Life Technologies, Carlsbad, Calif.). The results are shown in Table 3.

TABLE 3

Summary of mutations detected by NGS (Next-Generation Sequencing) on cfDNA prepared by the CGD method or prior art method

| Sample | Mutation Detected by CGD Method (Mutant %, Read Depth) | Mutation Detected by QIAamp Method (Mutant %, Read Depth) |
|---|---|---|
| 1 | EGFR, G719D (6.5%, 1358) | QNS |
| 2 | PIK3CA, K111R (2.1%, 1189) ABL1, Y253H (2.4%, 1189) SMAD4, C499Y (2.1%, 1189) | QNS |
| 3 | None | QNS |
| 4 | None | None |
| 5 | HNF1A, R272H (3.0%, 1191) TP53, E221K (4.8%, 1191) | None |
| 6 | GNAS, R844C (3.2%, 1338) GNAS, R201C (3.2%, 1338) | QNS |
| 7 | PIK3CA, K111R (5.1%, 1023) EGFR, E734K (7.6%, 1023) EGFR, R776H (2.0%, 1023) HNF1A, T260M (13.1%, 1023) | None |
| 8 | PIK3CA, K111R (2.9%, 1783) EGFR, I821T (2.4%, 1783) TP53, R273C (3.7%, 1783) | QNS |
| 9 | VHL, C162R (1.9%, 1006) CTNNB1, T40I (1.8%, 1006) | None |
| 10 | None | None |
| 11 | PTEN, Q171E (3.1%, 1507) | QNS |
| 12 | TP53, P725 (3.3%, 1108) | None |
| 13 | None | None |

TABLE 3-continued

Summary of mutations detected by NGS (Next-Generation
Sequencing) on cfDNA prepared by the CGD
method or prior art method

| Sample | Mutation Detected by CGD Method (Mutant %, Read Depth) | Mutation Detected by QIAamp Method (Mutant %, Read Depth) |
|---|---|---|
| 14 | None | TP53, S215G (2.2%, 463) |
| 15 | None | None |
| 16 | BRAF, V600M (3.8%, 2412) BRAF, I592V (3.3%, 2412) TP53, Y205H (2.2%, 2412) SMAD4, D355G (11.8%, 2412) | QNS |
| 17 | TP53, R249G (8.1%, 3542) | QNS |

Of the 17 samples tested, eight samples (8/17, 47.1%) using cfDNA prepared by the QIAamp kit were QNS (quantity not sufficient) to yield a result, consistent with previous Qubit and real-time PCR results in Example 1. All samples using cfDNA prepared by the CGD method were analyzable (17/17, 100%). NGS analysis showed four concordant cases which were determined to be wild-type (no mutation) using cfDNA prepared by the CGD method and from the QIAamp kit (samples 4, 10, 13 and 15). NGS analysis also revealed 5 discordant cases using cfDNA prepared by the CGD method and from the QIAamp kit. In four cases, cfDNA prepared using the QIAamp kit revealed no mutation, while at least one mutation was detected in the same samples using cfDNA prepared by the CGD method (samples 5, 7, 9 and 12). In one case, cfDNA prepared using the QIAamp kit revealed a single mutation (low coverage, 463×) while cfDNA prepared by the CGD method from the same sample yielded a wild-type result (sample 14).

After filtering out silent mutations and unconfirmed somatic mutations, 11 of 17 subjects (64.7%) had at least one mutation detected by NGS analysis when using cfDNA prepared by the CGD method. The read depth for those samples ranged from 1006×-3542×. In contrast, NGS analysis using cfDNA prepared using the QIAamp kit revealed a mutation in only 1/17 subjects (5.9%). NGS analysis using cfDNA prepared by the CGD method allowed the determination of 23 mutations in 11 samples that were not detected by NGS analysis using cfDNA prepared using the QIAamp kit. All mutations identified were substitutions. Together, the NGS results demonstrated that cfDNA extracted by the CGD method provided superior starting material for analysis as compared to prior art methods. Furthermore, in comparison the QIAamp kit showed a high QNS and false negative rate due to loss in the cfDNA preparation step.

In an additional experiment, to address the issues regarding sample variability and potential failure to detect biomarkers, spike-and-recovery experiments were performed. Two NGS reference standards from Horizon Diagnostics were tested: standard 4 covers 10 mutations at 5% and standard 6 carries 20 mutations at 2.5%, both in genomic DNA format. Two spiking concentrations were used (5 and 20 ng/mL) in reference to 10-30 ng/mL of cfDNA usually found in healthy individuals. As shown in Table 4, sixty percent of mutations (6/10 and 12/20), either at 2.5% or 5%, can be detected by NGS analysis in samples prepared by the CGD method, while no mutations were detectable by NGS analysis in the same spiked samples prepared using the QIAamp kit. The results of spiking studies were consistent with the previous NGS analysis data and further confirmed that the CGD method yielded higher quantities of cfDNA from less plasma as compared to prior art methods and resulted in the identification of more mutations.

TABLE 4

Summary of mutations detected by NGS (Next-Generation Sequencing) on spiked plasma samples prepared by the CGD method or prior art method

| Sample | CGD Method | QIAamp Method |
|---|---|---|
| Spiked 5 ng/mL Std 4 Reference DNA (10 mutations, 5% mutant fractions, Horizon Dx) | 6/10 | 0/10 |
| Spiked 20 ng/mL Std 6 Reference DNA (20 mutations, 2.5% mutant fractions, Horizon Dx) | 12/20 | 0/20 |

The CGD method allows advanced genomic analyses (e.g., next-generation sequencing) on cfDNA prepared directly from droplet volumes of plasma (as low as 20 μL). The CGD methods can be applied to a broad range of clinical genetic tests with the advantages of minimal sample volume, maximal yield, streamlined workflow with reduced costs and turnaround time.

Example 4—ISA of Saliva Samples Using the CGD Method

The present example illustrates the use saliva samples in the CGD method. In this example, the CGD method was performed according to protocol. Saliva samples were obtained from two individual subjects. The saliva sample was obtained with a commercial sampling kit (Pure-SAL Oral Specimen Collection System; Oasis Diagnostics) with or without preservatives. 20 μL of saliva sample was used as input and an analyzable pool of cfDNA molecules was produced.

Samples for this example were saliva samples taken from two different subject, both with and without preservatives present in commercial saliva sampling kits, with 20 μL of the sample being used for each experiment. Saliva samples were processed to produce the analyzable pool of cfDNA pool as described in protocol A. Total yield of amplified cfDNA was quantified using the Qubit 2.0 Fluorometer as described above.

The cfDNA resulting from the CGD methods was subjected to agarose gel electrophoresis on a 2% gel and visualized using ethidium bromide (FIG. 4). In FIG. 4, lanes 1 and 2 show the results from saliva samples obtained with a commercial sampling kit with preservatives with lane 3 being the a negative control (no saliva sample present), while lanes 4 and 5 show results from saliva samples obtained with a commercial sampling kit without preservatives with lane 6 being the a negative control (no saliva sample present). cfDNA from saliva samples taken directly showed strong staining intensity indicating the presence of abundant cfDNA produced by the CGD method. In contrast, saliva samples taken using a commercial kit containing preservatives and other agents showed little or no staining (lanes 1 and 2).

This example shows the CGD method may be used efficiently to produce an analyzable pool of cfDNA molecules from cfDNA present in a saliva sample. Furthermore, this example demonstrates that agents present in commercial sampling kits may interfere with the amplification of cfDNA by the CGD method.

Example 5—ISA of Plasma, Urine and Cerebrospinal Fluid Samples Using the CGD Method The present example illustrates the use plasma, urine and cerebrospinal fluid (CSF) samples in the CGD method. In this example, the CGD method was performed according to protocol A. Samples were processed to produce the analyzable pool of cfDNA pool as described in protocol A. The analyzable pool of cfDNA was subject to NGS analysis as described. Total yield of amplified cfDNA was quantified using the Qubit 2.0 Fluorometer as described above.

Frozen samples were obtained from a variety of sources. For plasma and CSF samples, 20 µL of the sample was used as input in the CGD method while 10 µL of the sample was used as input in the CGD method for urine samples.

The cfDNA resulting from the CGD methods was subjected to agarose gel electrophoresis on a 2% gel and visualized using ethidium bromide with a 1 kb ladder (FIG. 5). In FIG. 5, cfDNA prepared from various samples was as follows, with cfDNA concentration in ng/µL provided in parens: lane 1 CSF (8.5), lane 2 urine (5.1), lane 3 plasma (22), lane 4 plasma (59), lanes 5 plasma (36.4), lane 6 negative control, lane 7 urine (52.2), lane 8 urine (11.2), lanes 9 urine (89.6) and lane 10 urine (30). cfDNA from all samples showed strong staining intensity indicating the presence of abundant cfDNA produced by the CGD method. cfDNA prepared from the samples shown in lanes 1 to 6 of FIG. 5 were also analyzed by the Agilent 2100 Bioanalyzer to determine the size distribution and quantitation of cfDNA prepare by the CGD method (FIG. 6).

This example shows the CGD method may be used efficiently to produce an analyzable pool of cfDNA molecules from cfDNA present in a variety of sample types. Furthermore, the size distribution of cfDNA using the CGD method is generally in the 100 to 600 kb range, which is beneficial for downstream analysis.

Example 6—Determination of Mutant Fraction Using cfDNA

The present example illustrates the determination of absolute copy number of wild-type and mutant cfDNA and the calculation of mutant fraction. cfDNA was prepared from plasma and CSF samples (200 µL) using the QIAamp kit (used according to manufacturer's instructions). Sample was used directly for the CGD method. The CGD method was performed according to protocol A. Samples for this example were plasma samples taken from the subjects. Plasma samples were processed to produce the analyzable cfDNA pool as described in protocol A. Sample input volumes for the CGD method were 200 µL and 200 µL for the CGD method and QiaAmp Kit, respectively. cfDNA was prepared from 6 plasma samples and 1 CSF sample along with positive and negative controls. cfDNA was analyzed by an independent laboratory using the QX200 Droplet Digital PCR System (Bio-Rad, Hercules, Calif.).

ddPCR allows for high-precision, absolute quantification of nucleic acid target sequences. Following PCR amplification reaction within each droplet using a thermal cycler, absolute copy number was measured by counting nucleic acid molecules encapsulated in discrete, volumetrically defined water-in-oil droplet partitions. Droplets are streamed in single file on a droplet reader, which counts two different fluorescent signals, one for wild-type DNA, another for mutant DNA. Mutant fraction was calculated using the formula: % Mutant Fraction=(Mutant Copy Number/Total Copy Number)×100. The results are shown in Table 5.

As can be seen in Table 5, cfDNA prepared using the CGD method was superior in enriching for mutant fractions as compared to the methods of the prior art. Of the 7 samples tested, the CGD method provided for superior enrichment of mutant fractions in 5/7 samples (71.4%).

TABLE 5

|  | Mutant Fraction | |
| --- | --- | --- |
| Sample ID | QiaAmp | CGD |
| 1 | 17.84 | 5.11 |
| 2 | 2.65 | 2.01 |
| 3 | 0.93 | 43.57 |
| 4 | 1.31 | 14.62 |
| 5 | 0.95 | 34.31 |
| 6 | 0.02 | 0.97 |
| 7 | 0.31 | 2.25 |
| Neg Control | 0.22 | 0.37 |
| Pos Control | 49.68 | 46.11 |

Example 6—Reproducibility of the CGD Method

The present example shows the reproducibility of the CGD method. Six quality control samples (2 positive controls, 2 negative controls and 2 spike process controls) were analyzed over a period of 10 months. For positive controls, the commercially available cell lines SW480 and NCI-H1975 were used. For negative controls, the commercially available cell lines NA12878 and NA19240 were used. All cell lines were purchased from American Type Culture Collection (Manassas, Va.). For process controls, two previously tested positive patient DNA samples were used to spike into normal plasmas (final concentration 200 ng/ml) to generate the two process controls. DNA was isolated from the cells and 10 ng DNA was used as input in the CGD method.

The CGD method was performed according to protocol A. The analyzable pool of cfDNA was subject to NGS analysis as described above. The results are shown in Table 6A. Table 6A shows the variant calls of genes and mutations indicated by COSMIC ID numbers, silent mutations and unconfirmed somatic mutations were not filtered out. Different COSMIC IDs may represent the same mutation. COSMIC IDs were taken from the Catalogue of Somatic Mutations in Cancer: http://cancer.sanger.ac.uk/cancergenome/projects/cosmic/.

As shown in Table 6A, the CGD method was completely reproducible over time with 100% agreement over all testing periods using the quality control samples.

TABLE 6A

| Controls | Dec. 10, 2014 | Dec. 18, 2014 | Jan. 22, 2015 | Aug. 26, 2015 | Sep. 1, 2015 | Sep. 12, 2015 |
| --- | --- | --- | --- | --- | --- | --- |
| Process Control 1 | PDGFRA (COSM22413), | PDGFRA (COSM22413), | PDGFRA (COSM22413), | PDGFRA (COSM22413), | PDGFRA (COSM22413), | PDGFRA (COSM22413), |

TABLE 6A-continued

| Controls | Dec. 10, 2014 | Dec. 18, 2014 | Jan. 22, 2015 | Aug. 26, 2015 | Sep. 1, 2015 | Sep. 12, 2015 |
|---|---|---|---|---|---|---|
| (Spiked Sample) | APC (COSM19049, COSM27993), KIT (COSM1324), JAK3 (COSM34215) | APC (COSM19049, COSM27993), KIT (COSM1324), JAK3 (COSM34215) | APC (COSM19049, COSM27993), KIT (COSM1324), JAK3 (COSM34215) | APC (COSM19049, COSM27993), KIT (COSM1324), JAK3 (COSM34215) | APC (COSM19049, COSM27993), KIT (COSM1324), JAK3 (COSM34215) | APC (COSM19049, COSM27993), KIT (COSM1324), JAK3 (COSM34215) |
| Process Control 2 (Spiked Sample) | APC (COSM19049), EGFR (COSM28601), BRAF (COSM1120), TP53 (COSM43737, COSM44091, COSM44358, COSM45777, COSM44852) | APC (COSM19049), EGFR (COSM28601), BRAF (COSM1120), TP53 (COSM43737, COSM44091, COSM44358, COSM45777, COSM44852) | APC (COSM19049), EGFR (COSM28601), BRAF (COSM1120), TP53 (COSM43737, COSM44091, COSM44358, COSM45777, COSM44852) | APC (COSM19049), EGFR (COSM28601), BRAF (COSM1120), TP53 (COSM43737, COSM44091, COSM44358, COSM45777, COSM44852) | APC (COSM19049), EGFR (COSM28601), BRAF (COSM1120), TP53 (COSM43737, COSM44091, COSM44358, COSM45777, COSM44852) | APC (COSM19049), EGFR (COSM28601), BRAF (COSM1120), TP53 (COSM43737, COSM44091, COSM44358, COSM45777, COSM44852) |
| SW480 | PDGFRA (COSM22413), KIT (COSM28026), HRAS (COSM249860), KRAS (COSM520), TP53 (COSM10660, COSM99729), SMAD4 (COSM14167) | PDGFRA (COSM22413), KIT (COSM28026), HRAS (COSM249860), KRAS (COSM520), TP53 (COSM10660, COSM99729), SMAD4 (COSM14167) | PDGFRA (COSM22413), KIT (COSM28026), HRAS (COSM249860), KRAS (COSM520), TP53 (COSM10660, COSM99729), SMAD4 (COSM14167) | PDGFRA (COSM22413), KIT (COSM28026), HRAS (COSM249860), KRAS (COSM520), TP53 (COSM10660, COSM99729), SMAD4 (COSM14167) | PDGFRA (COSM22413), KIT (COSM28026), HRAS (COSM249860), KRAS (COSM520), TP53 (COSM10660, COSM99729), SMAD4 (COSM14167) | PDGFRA (COSM22413), KIT (COSM28026), HRAS (COSM249860), KRAS (COSM520), TP53 (COSM10660, COSM99729), SMAD4 (COSM14167) |
| NCI-H1975 | PDGFRA (COSM22413), EGFR (COSM6240, COSM6224), CDKN2A (COSM13281) HRAS (COSM249860), TP53 (COSM10660, COSM99729), SMARCB1 (COSM1090) | PDGFRA (COSM22413), EGFR (COSM6240, COSM6224), CDKN2A (COSM13281) HRAS (COSM249860), TP53 (COSM10660, COSM99729), SMARCB1 (COSM1090) | PDGFRA (COSM22413), EGFR (COSM6240, COSM6224), CDKN2A (COSM13281) HRAS (COSM249860), TP53 (COSM10660, COSM99729), SMARCB1 (COSM1090) | PDGFRA (COSM22413), EGFR (COSM6240, COSM6224), CDKN2A (COSM13281) HRAS (COSM249860), TP53 (COSM10660, COSM99729), SMARCB1 (COSM1090) | PDGFRA (COSM22413), EGFR (COSM6240, COSM6224), CDKN2A (COSM13281) HRAS (COSM249860), TP53 (COSM10660, COSM99729), SMARCB1 (COSM1090) | PDGFRA (COSM22413), EGFR (COSM6240, COSM6224), CDKN2A (COSM13281) HRAS (COSM249860), TP53 (COSM10660, COSM99729), SMARCB1 (COSM1090) |
| NA19240 | IDH1 (NOCOSM105), PDGFRA (COSM22413), STK11 (COSM29005) | IDH1 (NOCOSM105), PDGFRA (COSM22413), STK11 (COSM29005) | IDH1 (NOCOSM105), PDGFRA (COSM22413), STK11 (COSM29005) | IDH1 (NOCOSM105), PDGFRA (COSM22413), STK11 (COSM29005) | IDH1 (NOCOSM105), PDGFRA (COSM22413), STK11 (COSM29005) | IDH1 (NOCOSM105), PDGFRA (COSM22413), STK11 (COSM29005) |
| NA12878 | PDGFRA (COSM22413) | PDGFRA (COSM22413) | PDGFRA (COSM22413) | PDGFRA (COSM22413) | PDGFRA (COSM22413) | PDGFRA (COSM22413) |

Intra-assay variation using the CGD method was also examined. Fifteen plasma samples (2 from healthy subjects; 4 from cancer subjects, 2 spiked plasma samples, 4 cell line samples and 3 serum samples) were collected. Spikes plasma samples were prepared as above. DNA was purified from the cell lines and 10 ng DNA used as input into the CGD method. The CGD method was performed according to protocol A. The analyzable pool of cfDNA was subject to NGS analysis as described above. The 15 libraries with mutations at different frequencies were indexed with different barcodes, multiplexed, and tested 5 times within the same run using Ion Proton NGS assay. The average read depth was >200×.

The results are shown in Table 6B. Table 6B shows the variant calls of genes and mutations indicated by COSMIC ID numbers, silent mutations and unconfirmed somatic mutations were not filtered out. Different COSMIC IDs may represent the same mutation. COSMIC IDs were taken from the Catalogue of Somatic Mutations in Cancer: http://cancer.sanger.ac.uk/cancergenome/projects/cosmic/. The concordance between replicate analyses is also shown. The results show 100% concordance for the mutation calls within each of the replicate analyses. The variant frequencies of mutations were highly reproducible (% CV<10%).

TABLE 6B

|   | Rep 1 | Rep 2 | Rep 3 | Rep 4 | Rep 5 | Con % |
|---|---|---|---|---|---|---|
| 1 | BRAF (COSM21542) ATM (COSM21826) | BRAF (COSM21542) ATM (COSM21826) | BRAF (COSM21542), ATM (COSM21826) | BRAF (COSM21542) ATM (COSM21826) | BRAF (COSM21542) ATM (COSM21826) | 100 |
| 2 | KIT (COSM28026), APC (COSM13121) | KIT (COSM28026), APC (COSM13121) | KIT (COSM28026) APC (COSM13121) | KIT (COSM28026) APC (COSM13121) | KIT (COSM28026) APC (COSM13121) | 100 |
| 3 | CTNNB1 (COSM 5738) PDGFRA (COSM22413) KIT (COSM28026 COSM1243) TP53 (COSM43968 COSM43980 COSM44413) | CTNNB1 (COSM 5738), PDGFRA (COSM22413) KIT (COSM28026, COSM1243) TP53 (COSM43968 COSM43980 COSM44413) | CTNNB1 (COSM 5738) PDGFRA (COSM22413) KIT (COSM28026 COSM1243) TP53 (COSM43968 COSM43980 COSM44413) | CTNNB1 (COSM 5738) PDGFRA (COSM22413) KIT (COSM28026 COSM1243) TP53 (COSM43968 COSM43980 COSM44413) | CTNNB1 (COSM 5738) PDGFRA (COSM22413) KIT (COSM28026, COSM1243) TP53 (COSM43968 COSM43980 COSM44413) | 100 |
| 4 | PTEN (COSM5121), TP53 (COSM43747, COSM10684) | PTEN (COSM5121), TP53 (COSM43747, COSM10684) | PTEN (COSM5121), TP53 (COSM43747, COSM10684) | PTEN (COSM5121) TP53 (COSM43747, COSM10684) | PTEN (COSM5121), TP53 (COSM43747, COSM10684) | 100 |
| 5 | KIT (COSM12711), TP53 (COSM11449) | KIT (COSM12711), TP53 (COSM11449) | KIT (COSM12711), TP53 (COSM11449) | KIT (COSM12711) TP53 (COSM11449) | KIT (COSM12711), TP53 (COSM11449) | 100 |
| 6 | PDGFRA (COSM22413), EGFR (COSM18425) | PDGFRA (COSM22413), EGFR (COSM18425) | PDGFRA (COSM22413), EGFR (COSM18425) | PDGFRA (COSM22413), EGFR (COSM18425) | PDGFRA (COSM22413), EGFR (COSM18425) | 100 |
| 7 | KIT (COSM1155), RB1 (COSM895) | KIT (COSM1155), RB1 (COSM895) | KIT (COSM1155), RB1 (COSM895) | KIT (COSM1155), RB1 (COSM895) | KIT (COSM1155), RB1 (COSM895) | 100 |
| 8 | TP53 (COSM45326) | TP53 (COSM45326) | TP53 (COSM45326) | TP53 (COSM45326) | TP53 (COSM45326) | 100 |
| 9 | BRAF (COSM476), PTPN11 (COSM13014) | BRAF (COSM476), PTPN11 (COSM13014) | BRAF (COSM476), PTPN11 (COSM13014) | BRAF (COSM476), PTPN11 (COSM13014) | BRAF (COSM476), PTPN11 (COSM13014) | 100 |
| 10 | PDGFRA (COSM22413), APC (COSM19049, COSM27993), JAK3 (COSM34215) | PDGFRA (COSM22413), APC (COSM19049, COSM27993), JAK3 (COSM34215) | PDGFRA (COSM22413), APC (COSM19049, COSM27993), JAK3 (COSM34215) | PDGFRA (COSM22413), APC (COSM19049 COSM27993) JAK3 (COSM34215) | PDGFRA (COSM22413), APC (COSM19049, COSM27993), JAK3 (COSM34215) | 100 |
| 11 | APC (COSM19049), EGFR (COSM28601), BRAF (COSM1120), TP53 (COSM43737) | APC (COSM19049), EGFR (COSM28601), BRAF (COSM1120), TP53 (COSM43737) | APC (COSM19049), EGFR (COSM28601), BRAF (COSM1120), TP53 (COSM43737) | APC (COSM19049), EGFR (COSM28601), BRAF (COSM1120), TP53 (COSM43737) | APC (COSM19049), EGFR (COSM28601), BRAF (COSM1120), TP53 (COSM43737) | 100 |
| 12 | PDGFRA (COSM22413) KIT (COSM28026) HRAS (COSM249860 KRAS (COSM520) TP53 (COSM10660 COSM99729) SMAD4 (COSM14167) | PDGFRA (COSM22413), KIT (COSM28026), HRAS (COSM249860), KRAS (COSM520) TP53 (COSM10660 COSM99729) SMAD4 (COSM14167) | PDGFRA (COSM22413) KIT (COSM28026) HRAS COSM249860 KRAS (COSM520) TP53 (COSM10660 COSM99729) SMAD4 (COSM14167) | PDGFRA (COSM22413) KIT (COSM28026) HRAS (COSM249860 KRAS (COSM520) TP53 (COSM10660 COSM99729) SMAD4 (COSM14167) | PDGFRA (COSM22413) KIT (COSM28026) HRAS (COSM249860 KRAS (COSM520), TP53 (COSM10660, COSM99729) SMAD4 (COSM14167) | 100 |
| 13 | PDGFRA (COSM22413) EGFR (COSM6240, COSM6224) CDKN2A (COSM13281) HRAS | PDGFRA (COSM22413) EGFR (COSM6240 COSM6224) CDKN2A (COSM13281) HRAS | PDGFRA (COSM22413) EGFR (COSM6240 COSM6224) CDKN2A (COSM13281) HRAS | PDGFRA (COSM22413) EGFR (COSM6240 COSM6224) CDKN2A (COSM13281) HRAS | PDGFRA (COSM22413) EGFR (COSM6240 COSM6224) CDKN2A (COSM13281) HRAS | 100 |

TABLE 6B-continued

| | Rep 1 | Rep 2 | Rep 3 | Rep 4 | Rep 5 | Con % |
|---|---|---|---|---|---|---|
| | (COSM249860 TP53 (COSM10660, COSM99729) SMARCB1 (COSM1090) | (COSM249860), TP53 (COSM10660, COSM99729) SMARCB1 (COSM1090) | (COSM249860 TP53 (COSM10660, COSM99729) SMARCB1 (COSM1090) | (COSM249860 TP53 (COSM10660 COSM99729) SMARCB1 (COSM1090) | (COSM249860 TP53 (COSM10660 COSM99729) SMARCB1 (COSM1090) | |
| 14 | IDH1 (NOCOSM105 PDGFRA (COSM22413) STK11 (COSM29005) | IDH1 (NOCOSM105) PDGFRA (COSM22413) STK11 (COSM29005) | IDH1 (NOCOSM105 PDGFRA (COSM22413) STK11 (COSM29005) | IDH1 (NOCOSM105 PDGFRA (COSM22413) STK11 (COSM29005) | IDH1 (NOCOSM105 PDGFRA (COSM22413) STK11 (COSM29005) | 100 |
| 15 | PDGFRA (COSM22413) | PDGFRA (COSM22413) | PDGFRA (COSM22413) | PDGFRA (COSM22413) | PDGFRA (COSM22413) | 100 |

An inter-assay reproducibility study was performed over 5 different runs by 2 operators using the 15 samples described in the intra-assay study. The CGD method was performed according to protocol A. The analyzable pool of cfDNA was subject to NGS analysis as described above. The 15 libraries with mutations at different frequencies were indexed with different barcodes, multiplexed, and tested in 5 separate runs using Ion Proton NGS assay. The average read depth is >200×.

The results are shown in Table 6C. Table 6C shows the variant calls of genes and mutations indicated by COSMIC ID numbers, silent mutations and unconfirmed somatic mutations were not filtered out. Different COSMIC IDs may represent the same mutation. COSMIC IDs were taken from the Catalogue of Somatic Mutations in Cancer: http://cancer.sanger.ac.uk/cancergenome/projects/cosmic/. The concordance between replicate analyses is also shown. As with the inter-assay study, the results show 100% concordance for the mutation calls in all 5 analyses. The variant frequencies of mutations were highly reproducible (% CV<10%).

TABLE 6C

| | Run 1 | Run 2 | Run 3 | Run 4 | Run 5 | Con % |
|---|---|---|---|---|---|---|
| 1 | BRAF (COSM21542), ATM (COSM21826) | BRAF (COSM21542), ATM (COSM21826) | BRAF (COSM21542), ATM (COSM21826) | BRAF (COSM21542), ATM (COSM21826) | BRAF (COSM21542), ATM (COSM21826) | 100 |
| 2 | KIT (COSM28026), APC (COSM13121) | KIT (COSM28026), APC (COSM13121) | KIT (COSM28026), APC (COSM13121) | KIT (COSM28026), APC (COSM13121) | KIT (COSM28026), APC (COSM13121) | 100 |
| 3 | CTNNB1 (COSM 5738), PDGFRA (COSM22413), KIT (COSM28026, COSM1243), TP53 (COSM43968, COSM43980, COSM44413) | CTNNB1 (COSM 5738), PDGFRA (COSM22413), KIT (COSM28026, COSM1243), TP53 (COSM43968, COSM43980, COSM44413) | CTNNB1 (COSM 5738), PDGFRA (COSM22413), KIT (COSM28026, COSM1243), TP53 (COSM43968, COSM43980, COSM44413) | CTNNB1 (COSM 5738), PDGFRA (COSM22413), KIT (COSM28026, COSM1243), TP53 (COSM43968, COSM43980, COSM44413) | CTNNB1 (COSM 5738), PDGFRA (COSM22413), KIT (COSM28026, COSM1243), TP53 (COSM43968, COSM43980, COSM44413) | 100 |
| 4 | PTEN (COSM5121), TP53 (COSM43747, COSM10684) | PTEN (COSM5121), TP53 (COSM43747, COSM10684) | PTEN (COSM5121), TP53 (COSM43747, COSM10684) | PTEN (COSM5121), TP53 (COSM43747, COSM10684) | PTEN (COSM5121), TP53 (COSM43747, COSM10684) | 100 |
| 5 | KIT (COSM12711), TP53 (COSM11449) | KIT (COSM12711), TP53 (COSM11449) | KIT (COSM12711), TP53 (COSM11449) | KIT (COSM12711), TP53 (COSM11449) | KIT (COSM12711), TP53 (COSM11449) | 100 |
| 6 | PDGFRA (COSM22413), EGFR (COSM18425) | PDGFRA (COSM22413), EGFR (COSM18425) | PDGFRA (COSM22413), EGFR (COSM18425) | PDGFRA (COSM22413), EGFR (COSM18425) | PDGFRA (COSM22413), EGFR (COSM18425) | 100 |
| 7 | KIT (COSM1155), RB1 (COSM895) | KIT (COSM1155), RB1 (COSM895) | KIT (COSM1155), RB1 (COSM895) | KIT (COSM1155), RB1 (COSM895) | KIT (COSM1155), RB1 (COSM895) | 100 |
| 8 | TP53 (COSM45326) | TP53 (COSM45326) | TP53 (COSM45326) | TP53 (COSM45326) | TP53 (COSM45326) | 100 |
| 9 | BRAF (COSM476), PTPN11 (COSM13014) | BRAF (COSM476), PTPN11 (COSM13014) | BRAF (COSM476), PTPN11 (COSM13014) | BRAF (COSM476), PTPN11 (COSM13014) | BRAF (COSM476), PTPN11 (COSM13014) | 100 |

TABLE 6C-continued

| | Run 1 | Run 2 | Run 3 | Run 4 | Run 5 | Con % |
|---|---|---|---|---|---|---|
| 10 | PDGFRA (COSM22413), APC (COSM19049, COSM27993), JAK3 (COSM34215) | PDGFRA (COSM22413), APC (COSM19049, COSM27993), JAK3 (COSM34215) | PDGFRA (COSM22413), APC (COSM19049, COSM27993), JAK3 (COSM34215) | PDGFRA (COSM22413), APC (COSM19049, COSM27993), JAK3 (COSM34215) | PDGFRA (COSM22413), APC (COSM19049, COSM27993), JAK3 (COSM34215) | 100 |
| 11 | APC (COSM19049), EGFR (COSM28601), BRAF (COSM1120), TP53 (COSM43737) | APC (COSM19049), EGFR (COSM28601), BRAF (COSM1120), TP53 (COSM43737) | APC (COSM19049), EGFR (COSM28601), BRAF (COSM1120), TP53 (COSM43737) | APC (COSM19049), EGFR (COSM28601), BRAF (COSM1120), TP53 (COSM43737) | APC (COSM19049), EGFR (COSM28601), BRAF (COSM1120), TP53 (COSM43737) | 100 |
| 12 | PDGFRA (COSM22413), KIT (COSM28026), HRAS (COSM249860 KRAS (COSM520), TP53 (COSM10660, COSM99729), SMAD4 (COSM14167) | PDGFRA (COSM22413), KIT (COSM28026), HRAS (COSM249860 KRAS (COSM520), TP53 (COSM10660, COSM99729), SMAD4 (COSM14167) | PDGFRA (COSM22413), KIT (COSM28026), HRAS (COSM249860 KRAS (COSM520), TP53 (COSM10660, COSM99729), SMAD4 (COSM14167) | PDGFRA (COSM22413), KIT (COSM28026), HRAS (COSM249860 KRAS (COSM520), TP53 (COSM10660, COSM99729), SMAD4 (COSM14167) | PDGFRA (COSM22413), KIT (COSM28026), HRAS (COSM249860), KRAS (COSM520), TP53 (COSM10660, COSM99729), SMAD4 (COSM14167) | 100 |
| 13 | PDGFRA (COSM22413), EGFR (COSM6240, COSM6224), CDKN2A (COSM13281) HRAS (COSM249860 TP53 (COSM10660, COSM99729), SMARCB1 (COSM1090) | PDGFRA (COSM22413), EGFR (COSM6240, COSM6224), CDKN2A (COSM13281) HRAS (COSM249860 TP53 (COSM10660, COSM99729), SMARCB1 (COSM1090) | PDGFRA (COSM22413), EGFR (COSM6240, COSM6224), CDKN2A (COSM13281) HRAS (COSM249860 TP53 (COSM10660, COSM99729), SMARCB1 (COSM1090) | PDGFRA (COSM22413), EGFR (COSM6240, COSM6224), CDKN2A (COSM13281) HRAS (COSM249860 TP53 (COSM10660, COSM99729), SMARCB1 (COSM1090) | PDGFRA (COSM22413), EGFR (COSM6240, COSM6224), CDKN2A (COSM13281) HRAS (COSM249860), TP53 (COSM10660, COSM99729), SMARCB1 (COSM1090) | 100 |
| 14 | IDH1 (NOCOSM105 PDGFRA (COSM22413), STK11 (COSM29005) | IDH1 (NOCOSM105 PDGFRA (COSM22413), STK11 (COSM29005) | IDH1 (NOCOSM105 PDGFRA (COSM22413), STK11 (COSM29005) | IDH1 (NOCOSM105 PDGFRA (COSM22413), STK11 (COSM29005) | IDH1 (NOCOSM105), PDGFRA (COSM22413), STK11 (COSM29005) | 100 |
| 15 | PDGFRA (COSM22413) | PDGFRA (COSM22413) | PDGFRA (COSM22413) | PDGFRA (COSM22413) | PDGFRA (COSM22413) | 100 |

Example 7—Sensitivity of the CGD Method

This example illustrates the sensitivity and limit of detection (LOD) of the CGD method. In this example, the Horizon Dx NGS reference standards Tru-Q 4 and Tru-Q 7 were used. These standards contain known mutations at defined frequencies. The two standards were serially diluted into normal human genomic DNA (Promega) at 4:1, 3:2, 2:3 and 1:4 ratios to obtain different levels of mutations and analyzed by the CGD method.

The CGD method was performed according to protocol A. The analyzable pool of cfDNA was subject to NGS analysis as described above. The results are shown in Table 7A for Tru-Q 4 and Table 7B for Tru-Q 7. The tables provide each mutation present in the standard along with the mutation frequency and show the sensitivity (LOD) of the CGD method for each mutation for undiluted samples and for each serial dilution. Mean read depth of each sample was >4000×. The results show that the LOD for most actionable somatic mutations range from 1% to 3%.

TABLE 7A

| Variants in Tru-Q 4 | | Undiluted | 4:1 | 3:2 | 2:3 | 1:4 | LOD |
|---|---|---|---|---|---|---|---|
| ABL1 T315I | 5.0% | ✓ | ✓ | ✓ | ✓ | | 2.0% |
| BRAF V600E | 8.0% | ✓ | ✓ | ✓ | ✓ | | 3.2% |
| BRAF V600R | 4.0% | | | | | ✓ | |
| EGFR G719S | 16.7% | ✓ | ✓ | ✓ | ✓ | ✓ | 3.3% |
| EGFR L861Q | 4.2% | ✓ | ✓ | ✓ | ✓ | | 1.7% |
| IDH2 R172K | 5.0% | ✓ | ✓ | ✓ | ✓ | ✓ | 1.0% |
| KIT D816V | 5.0% | ✓ | ✓ | ✓ | | | 3.0% |
| KRAS G12C | 5.0% | ✓ | ✓ | ✓ | | | 3.0% |
| KRAS G12D | 5.0% | ✓ | ✓ | ✓ | ✓ | | 2.0% |
| KRAS G13D | 25.0% | ✓ | ✓ | ✓ | ✓ | | 10.0% |
| KRAS Q61H | 5.0% | ✓ | ✓ | ✓ | | | 3.0% |
| NRAS Q61R | 5.0% | ✓ | ✓ | ✓ | ✓ | | 2.0% |
| PDGFRA D842V | 5.0% | ✓ | ✓ | ✓ | | | 3.0% |
| PIK3CA H1047R | 30.0% | ✓ | ✓ | ✓ | ✓ | ✓ | 6.0% |

TABLE 7B

| Variants in Tru-Q 7 | Undiluted | 4:1 | 3:2 | 2:3 | 1:4 | LOD |
|---|---|---|---|---|---|---|
| ABL1 T315I | 1.3% | ✓ | | | | 1.3% |
| BRAF V600E | 8.0% | ✓ | ✓ | ✓ | ✓ | 1.6% |
| BRAF V600M | 1.0% | | | ✓ | | |
| EGFR G719S | 16.7% | ✓ | ✓ | ✓ | ✓ | 3.3% |
| EGFR T790M | 1.0% | | | | ✓ | |
| FLT3 D835Y | 1.3% | | ✓ | | | |
| FLT3 ΔI836 | 1.3% | | | | ✓ | |
| GNA11 Q209L | 1.3% | ✓ | | | | 1.3% |
| GNAQ Q209L | 1.3% | | ✓ | | | |
| IDH2 R140Q | 1.3% | ✓ | | | | 1.3% |
| IDH2 R172K | 1.3% | ✓ | | | | 1.3% |
| JAK2 V617F | 1.3% | ✓ | | | | 1.3% |
| KIT D816V | 1.3% | ✓ | ✓ | | | 1.0% |
| KRAS A146T | 1.3% | ✓ | | | | 1.3% |
| KRAS G12C | 1.3% | | ✓ | | | |
| KRAS G12R | 1.3% | | | | ✓ | |
| KRAS G12S | 1.3% | ✓ | | | | 1.3% |
| KRAS G13D | 25.0% | ✓ | ✓ | ✓ | ✓ | 5.0% |
| KRAS Q61L | 1.3% | ✓ | ✓ | | | 1.3% |
| NOTCH L1601P | 1.3% | ✓ | | | | 1.3% |
| NRAS Q61K | 1.3% | ✓ | ✓ | | | 1.0% |
| PIK3CA H1047R | 30.0% | ✓ | ✓ | ✓ | ✓ | 6.0% |

Example 8—Specificity of the CGD Method

The present example illustrates the specificity of the CGD method. Plasma samples were obtained from 17 healthy subjects. Plasma samples were analyzed at the Applicant's laboratories by the CGD method. The CGD method was performed according to protocol A. The analyzable pool of cfDNA was subject to NGS analysis as described above. The same plasma samples were analyzed at a second CLIA certified laboratory by using a commercially available cfDNA extraction kit to purify cfDNA. The cfDNA was analyzed with the Ion Torrent PCG sequencer according to manufacturer's instructions.

The results are shown in Table 8. Table 8 shows the variant calls of genes and mutations indicated by COSMIC ID numbers, silent mutations and unconfirmed somatic mutations were not filtered out. Different COSMIC IDs may represent the same mutation. COSMIC IDs were taken from the Catalogue of Somatic Mutations in Cancer: http://cancer.sanger.ac.uk/cancergenome/projects/cosmic/. The concordance between the CGD method and the comparison method is also shown. The results show the test specificity is 99.9% at the gene level (849/850) and in strong concordance ($^{16}/_{17}$; 94%) with the test performed by the second CLIA certified laboratory.

TABLE 8

| Sample ID | Circulogene | CLIA Lab 2 | Concordance |
|---|---|---|---|
| 1 | PDGFRA (COSM22413), TP53 (COSM43606, COSM39293, COSM179807, COSM179806, COSM179805, COSM44683) | PDGFRA (COSM22413), TP53 (COSM43606, COSM39293, COSM179807, COSM179806, COSM179805, COSM44683) | 100% |
| 2 | PIK3CA (COSM758), APC (COSM19099) | PIK3CA (COSM758), APC (COSM19099) | 100% |
| 3 | PDGFRA (COSM22413), MET (NOCOSM988), BRAF (COSM1116), RET (COSM29804), PTEN (COSM5101), ATM (COSM21825), TP53 (COSM12296), SMARCB1 (COSM1090) | PDGFRA (COSM22413), MET (NOCOSM988), BRAF (COSM1116), RET (COSM29804), PTEN (COSM5101), ATM (COSM21825), TP53 (COSM12296), SMARCB1 (COSM1090) | |
| 4 | PDGFRA (COSM22413), NRAS (COSM587), VI-IL (COSM14355), PIK3CA (COSM94986, COSM775), BRAF (COSM1116), PTEN (COSM5111) | PDGFRA (COSM22413), NRAS (COSM587), VIAL (COSM14355), PIK3CA (COSM94986, COSM775), BRAF (COSM1116), PTEN (COSM5111) | 100% |
| 5 | PIK3CA (COSM14052), KIT (COSM21983), APC (COSM19099), BRAF (COSM1116), GNAQ (COSM28760), TP53 (COSM45329, COSM43960, COSM46214) | PIK3CA (COSM14052), KIT (COSM21983), APC (COSM19099), BRAF (COSM1116), GNAQ (COSM28760), TP53 (COSM45329, COSM43960, COSM46214) | 100% |
| 6 | TP53 (COSM11517) | TP53 (COSM11517) | 100% |
| 7 | PDGFRA (COSM22413), KIT (COSM1290), APC (COSM19049), TP53 (COSM44512, COSM45511) | PDGFRA (COSM22413), KIT (COSM1290), APC (COSM19049), TP53 (COSM44512, COSM45511) | 100% |
| 8 | STK11 (COSM25851) | STK11 (COSM25851) | 100% |
| 9 | KIT (COSM28026) | KIT (COSM28026) | 100% |
| 10 | APC (COSM13125), TP53 (COSM44973), ERBB2 (COSM35496) | APC (COSM13125), TP53 (COSM44973), ERBB2 (COSM35496) | 100% |
| 11 | BRAF (COSM21542), ATM (COSM21826), TP53 (COSM45169) | BRAF (COSM21542), ATM (COSM21826) | One variant not called by CLIA Lab 2 |
| 12 | EGFR (COSM41603, COSM41663), MET (COSM710), BRAF (COSM461) | EGFR (COSM41603, COSM41663), MET (COSM710), BRAF (COSM461) | 100% |
| 13 | MET (COSM691), TP53 (COSM10995) | MET (COSM691), TP53 (COSM10995) | 100% |
| 14 | ATM (COSM21626), TP53 (COSM43879), SMAD4 (COSM13115) | ATM (COSM21626), TP53 (COSM43879), SMAD4 (COSM13115) | 100% |
| 15 | PDGFRA (COSM22413), MET (NOCOSM988), BRAF (COSM1116), TP53 (COSM11738, COSM44848) | PDGFRA (COSM22413), MET (NOCOSM988), BRAF (COSM1116), TP53 (COSM11738, COSM44848) | 100% |
| 16 | No mutation detected | No mutation detected | 100% |
| 17 | VHL (COSM30295), ERBB2 (COSM35496) | VHL (COSM30295), ERBB2 (COSM35496) | 100% |

In another comparison, 50 clinical plasma samples were obtained (from 15 pancreatic cancer patients; 15 colorectal cancer patients, 1 gastrointestinal stromal tumor patient, 4 lung cancer patients and 15 CEA-positive serum samples—marked with S). Plasma samples were analyzed at the Applicant's laboratories by the CGD method. The CGD method was performed according to protocol. The analyzable pool of cfDNA was subject to NGS analysis as described above. The same plasma samples were analyzed at the same second CLIA certified laboratory as described above.

The results are shown in Table 9. Table 9 shows the variant calls of genes and mutations indicated by COSMIC ID numbers, silent mutations and unconfirmed somatic mutations were not filtered out. Different COSMIC IDs may represent the same mutation. COSMIC IDs were taken from the Catalogue of Somatic Mutations in Cancer: http://cancer.sanger.ac.uk/cancergenome/projects/cosmic/. The concordance between the CGD method and the comparison method is also shown. The results show a concordance of 96% (48/50) with samples 2 and 8 being discordant.

TABLE 9

| Sample ID | Circulogene | CLIA Lab 2 | Concordance |
|---|---|---|---|
| 1 | PIK3CA (COSM27273), EZH2 (COSM37032), TP53 (COSM44397) | PIK3CA (COSM27273), EZH2 (COSM37032), TP53 (COSM44397) | 100% |
| 2 | FGFR3 (COSM718), IDH2 (COSM86960), TP53 (COSM45516) | KIT (COSM1255), AKT1 (COSM48226) | Discordant |
| 3 | KIT (COSM28026), APC (COSM13121), TP53 (COSM44578) | KIT (COSM28026), APC (COSM13121), TP53 (COSM44578) | 100% |
| 4 | KIT (COSM1290) | KIT (COSM1290) | 100% |
| 5 | PDGFRA (COSM22413), EGFR (COSM18425, COSM41663) | PDGFRA (COSM22413), EGFR (COSM18425, COSM41663) | 100% |
| 6 | PDGFRA (COSM22413) | PDGFRA (COSM22413) | 100% |
| 7 | PDGFRA (COSM22413), MET (COSM701), BRAF (COSM33729), SMO (COSM13146), ATM (COSM12791), TP53 (COSM45511) | PDGFRA (COSM22413), MET (COSM701), BRAF (COSM33729), SMO (COSM13146), ATM (COSM12791), TP53 (COSM45511) | 100% |
| 8 | PDGFRA (COSM22413), NRAS (COSM587, COSM583) | PIK3CA (COSM14052), ABL1 (COSM12576) RB1 (COSM1042), SMAD4 (COSM14221) | Discordant |
| 9 | CDKN2A (COSM12746) | NRAS (COSM577) | 100% |
| 10 | IDH1 (NOCOSM105), PIK3CA (COSM14052), PDGFRA (COSM22413), EGFR (COSM18419), RET (COSM978), HNF1A (COSM24923) | IDH1 (NOCOSM105), PIK3CA (COSM14052), PDGFRA (COSM22413), EGFR (COSM18419), RET (COSM978), HNF1A (COSM24923) | 100% |
| 11 | IDH1 (NOCOSM105), PDGFRA (COSM22413), TP53 (COSM43968, COSM99933, COSM10659, COSM44036) | IDH1 (NOCOSM105), PDGFRA (COSM22413), TP53 (COSM43968, COSM99933, COSM10659, COSM44036) | 100% |
| 12 | IDH1 (NOCOSM105), PDGFRA (COSM22413), STK11 (COSM20943) | IDH1 (NOCOSM105), PDGFRA (COSM22413), STK11 (COSM20943) | 100% |
| 13 | IDH1 (NOCOSM105), PDGFRA (COSM22413) | IDH1 (NOCOSM105), PDGFRA (COSM22413) | 100% |
| 14 | IDH1 (NOCOSM105), PDGFRA (COSM22413), PTEN (COSM5200), HNF1A (COSM24931) | IDH1 (NOCOSM105), PDGFRA (COSM22413), PTEN (COSM5200), HNF1A (COSM24931) | 100% |
| 15 | IDH1 (NOCOSM105), PDGFRA (COSM22413), ALK (COSM28057), BRAF (COSM18443), TP53 (COSM43692) | IDH1 (NOCOSM105), PDGFRA (COSM22413), ALK (COSM28057), BRAF (COSM18443), TP53 (COSM43692) | 100% |
| 16 | IDH1 (NOCOSM105), PDGFRA (COSM22413), TP53 (COSM44338, COSM44219), JAK3 (COSM34214) | IDH1 (NOCOSM105), PDGFRA (COSM22413), TP53 (COSM44338, COSM44219), JAK3 (COSM34214) | 100% |
| 17 | BRAF (COSM1130), SMAD4 (COSM14232) | BRAF (COSM1130), SMAD4 (COSM14232) | 100% |
| 18 | KIT (COSM1155), IDH2 (COSM33731) | KIT (COSM1155), IDH2 (COSM33731) | 100% |
| 19 | EGFR (COSM41663) | EGFR (COSM41663) | 100% |
| 20 | TP53 (COSM43872, COSM44328) | TP53 (COSM43872, COSM44328) | 100% |
| 21S | PDGFRA (COSM22413), KIT (COSM28026), PTEN (COSM28897) | PDGFRA (COSM22413), KIT (COSM28026), PTEN (COSM28897) | 100% |
| 22S | TP53 (COSM44120) | TP53 (COSM44120) | 100% |
| 23S | VHL (COSM25719), ATM (COSM21825), TP53 (COSM45332) | VHL (COSM25719), ATM (COSM21825), TP53 (COSM45332) | 100% |
| 24S | IDH1 (NOCOSM105), VHL (COSM18009), TP53 (COSM45189), SMAD4 (COSM14113) | IDH1 (NOCOSM105), VHL (COSM18009), TP53 (COSM45189), SMAD4 (COSM14113) | 100% |
| 25S | PIK3CA (COSM13570), EGFR (COSM13183), HNF1A (COSM24915) | PIK3CA (COSM13570), EGFR (COSM13183), HNF1A (COSM24915) | 100% |
| 26S | PIK3CA (COSM14052), PDGFRA (COSM22413), KIT (COSM 28026), TP53 (COSM44525) | PIK3CA (COSM14052), PDGFRA (COSM22413), KIT (COSM 28026), TP53 (COSM44525) | 100% |

TABLE 9-continued

| Sample ID | Circulogene | CLIA Lab 2 | Concordance |
|---|---|---|---|
| 27S | No mutation detected | No mutation detected | 100% |
| 28S | PDGFRA (COSM22413), KIT (COSM1273), PTPN11 (COSM13017) | PDGFRA (COSM22413), KIT (COSM1273), PTPN11 (COSM13017) | 100% |
| 29S | KIT (COSM28026), CSF1R (COSM954), PTEN (COSM5916) | KIT (COSM28026), CSF1R (COSM954), PTEN (COSM5916) | 100% |
| 30S | MPL (COSM43212), KRAS (COSM517), TP53 (COSM11449) | MPL (COSM43212), KRAS (COSM517), TP53 (COSM11449) | 100% |
| 31S | CTNNB1 (COSM5738), PIK3CA (COSM27134), PDGFRA (COSM 22413), KIT (COSM28026, COSM1243), PTEN (COSM5048), ATM (COSM21826), KRAS (COSM521), RB1 (COSM879), TP53 (COSM43968, COSM43980, COSM44413) | CTNNB1 (COSM5738), PIK3CA (COSM27134), PDGFRA (COSM 22413), KIT (COSM28026, COSM1243), PTEN (COSM5048), ATM (COSM21826), KRAS (COSM521), RB1 (COSM879), TP53 (COSM43968, COSM43980, COSM44413) | 100% |
| 32S | PDGFRA (COSM22413), KIT (COSM21983), EGFR (COSM28511, COSM28601), TP53 (COSM44129, COSM 11089) | PDGFRA (COSM22413), KIT (COSM21983), EGFR (COSM28511, COSM28601), TP53 (COSM44129, COSM 11089) | 100% |
| 33S | KIT (COSM1316), HRAS (COSM249860), ATM (COSM21826) | KIT (COSM1316), HRAS (COSM249860), ATM (COSM21826) | 100% |
| 34S | PTEN (COSM5121), TP53 (COSM10663, COSM99947, COSM43747, COSM10684, COSM43910) | PTEN (COSM5121), TP53 (COSM10663, COSM99947, COSM43747, COSM10684, COSM43910) | 100% |
| 35S | PDGFRA (COSM22413), KIT (COSM21983), APC (COSM18852), SMAD4 (COSM14096), GNAQ (COSM28760) | PDGFRA (COSM22413), KIT (COSM21983), APC (COSM18852), SMAD4 (COSM14096), GNAQ (COSM28760) | 100% |
| 36 | ERBB2 (COSM14060), TP53 (COSM44853) | ERBB2 (COSM14060), TP53 (COSM44853) | 100% |
| 37 | IDH1 (NOCOSM105), PDGFRA (COSM22413), TP53 (COSM44536, COSM43787), ERBB2 (COSM21985), GNAS (COSM123397, COSM27887), SMARCB1 (COSM1002) | IDH1 (NOCOSM105), PDGFRA (COSM22413), TP53 (COSM44536, COSM43787), ERBB2 (COSM21985), GNAS (COSM123397, COSM27887), SMARCB1 (COSM1002) | 100% |
| 38 | EGFR (COSM14243, COSM28603), KRAS (COSM12722, COSM528), TP53 (COSM44603, COSM44428, COSM43582) | EGFR (COSM14243, COSM28603), KRAS (COSM12722, COSM528), TP53 (COSM44603, COSM44428, COSM43582) | 100% |
| 39 | PIK3CA (COSM770), APC (COSM19718), RET (COSM966), TP53 (COSM11073, COSM99721, COSM45005, COSM44326), JAK3 (COSM34213) | PIK3CA (COSM770), APC (COSM19718), RET (COSM966), TP53 (COSM11073, COSM99721, COSM45005, COSM44326), JAK3 (COSM34213) | 100% |
| 40 | PDGFRA (COSM22413), APC (COSM19049, COSM27993), KIT (COSM1324), JAK3 (COSM34215) | PDGFRA (COSM22413), APC (COSM19049, COSM27993), KIT (COSM1324), JAK3 (COSM34215) | 100% |
| 41 | APC (COSM19049), EGFR (COSM28601), BRAF (COSM1120), TP53 (COSM43737, COSM44091, COSM44358, COSM45777, COSM44852) | APC (COSM19049), EGFR (COSM28601), BRAF (COSM1120), TP53 (COSM43737, COSM44091, COSM44358, COSM45777, COSM44852) | 100% |
| 42 | PDGFRA (COSM22413), KIT (COSM28026), HRAS (COSM249860), KRAS (COSM520), TP53 (COSM10660, COSM99729), SMAD4 (COSM14167) | PDGFRA (COSM22413), KIT (COSM28026), HRAS (COSM249860), KRAS (COSM520), TP53 (COSM10660, COSM99729), SMAD4 (COSM14167) | 100% |
| 43 | PDGFRA (COSM22413), EGFR (COSM6240, COSM6224), CDKN2A (COSM13281), HRAS (COSM249860), TP53 (COSM10660, COSM99729), SMARCB1 (COSM1090) | PDGFRA (COSM22413), EGFR (COSM6240, COSM6224), CDKN2A (COSM13281), HRAS (COSM249860), TP53 (COSM10660, COSM99729), SMARCB1 (COSM1090) | 100% |

TABLE 9-continued

| Sample ID | Circulogene | CLIA Lab 2 | Concordance |
|---|---|---|---|
| 44 | IDH1 (NOCOSM105), PDGFRA (COSM22413), STK11 (COSM29005) | IDH1 (NOCOSM105), PDGFRA (COSM22413), STK11 (COSM29005) | 100% |
| 45 | PDGFRA (COSM22413) | PDGFRA (COSM22413) | 100% |
| 46 | PDGFRA (COSM22413), KIT (COSM28026), HRAS (COSM249860), KRAS (COSM520), TP53 (COSM10660, COSM99729), SMAD4 (COSM14167) | PDGFRA (COSM22413), KIT (COSM28026), HRAS (COSM249860), KRAS (COSM520), TP53 (COSM10660, COSM99729), SMAD4 (COSM14167) | 100% |
| 47 | PDGFRA (COSM22413), EGFR (COSM6240, COSM6224), CDKN2A (COSM13281) HRAS (COSM249860), TP53 (COSM10660, COSM99729), SMARCB1 (COSM1090) | PDGFRA (COSM22413), EGFR (COSM6240, COSM6224), CDKN2A (COSM13281) HRAS (COSM249860), TP53 (COSM10660, COSM99729), SMARCB1 (COSM1090) | 100% |
| 48 | No mutation detected | No mutation detected | 100% |
| 49 | No mutation detected | No mutation detected | 100% |
| 50 | PDGFRA (COSM22413) | PDGFRA (COSM22413) | 100% |

These results show the CGD method compares very favorably with state of the art methods.

Example 9—Comparison of CGD Method to Tissue Biopsy Results

The present example illustrates the comparison of the CGD method to tissue biopsy. Plasma samples from breast cancer patients who had experienced relapse (n=13) and ovarian cancer patients (both pre- and post-chemotherapy) (n=15) were obtained. All subjects had tissue biopsy data available for comparison. For breast cancer patients, tissue biopsy data were available from two separate locations in the tumor. For ovarian cancer patients tissue biopsy data were available from both pre- and post-chemotherapy treatment; in addition, matched tissue genomic DNA was also extracted and provided for analysis. The results obtained cfDNA prepared from plasma samples was compared to the results from tissue biopsy.

The CGD method was performed according to protocol A. The analyzable pool of cfDNA obtained was subject to NGS analysis as described above.

For breast cancer patients who had experienced relapse, the results obtained with the CGD method showed strong agreement with the results obtained from tissue biopsy. Overall, there was a 69.2% concordance between the results obtained with the CGD method and the results obtained with tissue biopsy, which is consistent with reported concordance values in the art. The results are shown in Table 10.

TABLE 10

| | CGD Method | |
|---|---|---|
| Tissue Biopsy | Positive | Negative |
| Positive | 7 | 2 |
| Negative | 2 | 2 |

For the ovarian cancer comparison, the results obtained with the CGD method showed strong agreement with the results obtained from tissue biopsy, both pre- and post-chemotherapy treatment (see Tables 11 and 12 and FIG. 7). There was strong agreement in results between the two methods on KRAS, BRAF, PIK3CA and PTEN genes at both the patient level and mutation level (Table 11). The CGD method detected more genes with mutations and more mutations with individual genes as compared to tissue biopsy. The patterns with regard to the most frequently mutated genes were consistent between the CGD method and tissue biopsy (Table 12).

TABLE 11

| Tissue vs CGD n = 15 | KRAS | BRAF | PIK3CA | PTEN |
|---|---|---|---|---|
| Concordance (Patient Level) | 93.3% | 100% | 86.7% | 73.3% |
| Tissue vs CGD | KRAS (n = 64) | BRAF (n = 77) | PIK3CA (n = 101) | PTEN (N = 161) |
| Concordance (Mutation Level) | 98.4% | 100% | 98.8% | 99.4% |

TABLE 12

| | pre | post | pre | post |
|---|---|---|---|---|
| | cfDNA (plasma) | | DNA (tumor) | |
| # of mutated genes | 20 | 22 | 6 | 6 |
| Total # of mutations | 58 | 59 | 40 | 39 |
| Most frequently mutated genes | P53 (20/58) PI3KCA (6/58) KIT (5/58) EGFR (4/58) | P53 (17/59) KIT (8/59) PI3KCA (5/59) ATM (4/59) | P53 (25/40) KDR (5/40) KIT (5/40) PIK3CA (3/40) | P53(25/39) KDR (6/39) KIT (4/39) PIK3CA (2/39) |

When the results from the CGD method and tissue biopsy are compared according to treatment criteria (for example, pre- and post-chemotherapy treatment), the results CGD method and tissue biopsy provided consistent results at the gene level (FIG. 7). In FIG. 7, the data presented for each gene correspond to, from left to right, tissue biopsy pre-treatment, CGD method pre-treatment, tissue biopsy post-treatment and CGD method post-treatment.

These results show excellent agreement between the CGD method and the current state of the art tissue biopsy methods.

Example 10—Longitudinal Monitoring of Subjects Undergoing Cancer Therapy

In the present example, longitudinal monitoring of somatic alterations in plasma cfDNA was performed during therapy in 2 patients. The dynamics of mutation load was plotted and compared with cancer antigen (CA) markers and PET/CT imaging over the course of treatment. Imaging scans were evaluated using the Response Evaluation Criteria in Solid Tumors (RECIST).

In this example, the CGD method was performed according to protocol A. Samples for this example were plasma samples taken from two subjects over time. Total yield of amplified DNA was quantified using the Qubit 2.0 Fluorometer as described above. A concentration of 1-10 ng of the analyzable cfDNA pool was used to amplify 207 targeted loci using AmpliSeq Cancer Hotspot Panel, version 2 (Life Technologies, Carlsbad, Calif., USA), targeted for 2855 hotspot mutations within the 50 cancer driver genes, according to the supplier's protocol. Subsequent semiconductor-based sequencing was performed on Ion Chef and Ion Proton (Life Technologies, Carlsbad, Calif., USA), maintaining the number of reads as >200,000 per sample.

Subject 1 was a 69-year-old, non-smoking Chinese female patient with diagnosis of lung cancer with metastasis. Tissue biopsy showed sensitizing mutation in the epidermal growth factor receptor (EGF-R), while ALK, ROS-1, BRAF were negative (May 19, 2015). The subject initiated therapy with Tarceva (erlotinib hydrochloride, which targets EGF-R; 100 mg daily) and Avastin (bevacizumab) once a month. After near 5-month of therapy, the subject's carcinoma embryonic antigen (CEA), CA19-9 and CA125 levels all dropped significantly as determined by cfDNA analysis using the CGD method (FIG. XA). PET/CT scan evaluation also showed stable disease that was maintained for 101 days with decreases in tumor size and activity (FIG. XB). However, plasma cfDNA analysis using the CGD method detected two new somatic mutations that were maintained for approximately 50 days in the TP53 and PTEN genes. Detected tumor mutations gradually increased to 3, 7 and 8 mutations by the end of March 2016, indicating a progressive disease. The cfDNA analysis of March 2016 revealed 2 low-allele-frequency sub clones of EGFR, E114K (4.2%) and E868G (2.4%), implying a clonal evolution upon selection pressure by the drugs. PET/CT scans on Mar. 31, 2016 identified a new tumor mass (just beyond the level of resolution; about 1 cm$^3$), confirming the cfDNA analysis. Overall, this case demonstrates that the mutations detected by cfDNA analysis using the CGD method were closely associated with radiologically stable disease, with increases in the mutation load emerging ~2 months earlier than radiological progression. Furthermore, as PET/CT scans are recommended no more than two-times per year, the CGD methods offers an effective, safe alternative to longitudinal evaluation of subjects.

Subject 2 was a 79-year-old Iranian female patient with diagnosis of metastatic peri-pancreatic lymph node adenocarcinoma with an unknown primary. Immunohistochemistry on fine-needle biopsy was CK7 positive, while CK20, TTF, S100 and CD45 were all negative on Oct. 26, 2015. The subject was placed on XELOX therapy (chemotherapy regimen consisting of capecitabine combined with oxaliplatin) initially. Later, immunostaining also identified PD-L1 overexpression, therefore, she was then treated with XELIRI (a chemotherapy regimen consisting of capecitabine combined with irinotecan), Avastin (bevacizumab), and Opdivo (nivolumab). PET/CT scans on Feb. 11, 2016 showed significant decrease in tumor size and activity with >90% response rate (FIG. XB). Results plasma cfDNA analysis were in agreement with those of imaging, showing decreases in CEA and CA markers (CA125, CA27-29, CA19-9), indicating a stable disease maintained at least for 41 days (FIG. XA). Four somatic mutations were detected initially (FLT3 Y572C 6.5%; TP53 E165G 5.2%; TP53 Y104C 4.1%; TP53 C137Y 4.0%), then declined to 1 and zero mutation during the course of treatment. This case illustrated again the mutation analysis by blood-drop liquid biopsy correlated strongly with clinical outcomes in response to therapy.

Importantly, the CEA and CA protein markers are not necessarily specific to cancer cells and PET/CT scans suffer from resolution limitations. By contrast, cancer-associated somatic mutations detected herein by the CGD method are specific to malignancies, and plasma cfDNA with these mutations was shown to be indicative for the presence of malignancies. The results in this Example show that the levels of somatic mutations detected by cfDNA analysis using the CGD method correlated well with current standard of care test results and clinical outcomes and may provide the earliest indication of recurrence.

Example 11—Longitudinal Monitoring Using the CGD Method

The present example illustrates the use of the CGD method in longitudinal monitoring of cancer patients. Using the CGD method, enables clinicians to obtain real-time longitudinal information regarding treatment efficacy, residual disease, clonal evolution, drug resistance evolution and tumor recurrence. With accurate real-time information, clinicians can make more accurate decisions regarding therapeutic intervention, allowing the clinician to modify the current treatment to provide the most effective treatment in a cost-effective manner.

In this example, the CGD method was performed according to protocol A. Samples for this example were plasma samples taken from the subjects. The analyzable pool of cfDNA was subject to NGS analysis as described.

Table 13 shows exemplary results from analysis of patients with various cancers (CRC representing colorectal cancer; GIST representing gastrointestinal stromal tumor). The utility of longitudinal monitoring using the CGD method is evident from Table 13. For example, subject 1 with CRC showed a NRAS and PTEN mutations on initial testing in November 2015. During treatment, the patient was re-tested in December of 2015 with no mutations detected. In February 2015, the patient was re-tested and was positive for BRAF mutation (low frequency). As another example, subject 5 (lung cancer) was initially tested in November of 2015 and showed mutations in the TP53 gene. After further longitudinal testing in December 2015, January 2016 and February 2016, the alterations in tumor mutation pattern was evident. In this patient the original TP53 mutation was shown to decrease in frequency (although still present in February 2016), with the appearance of mutations in the KDR, ERBB4, VHL, CTNNb1 and RB1 genes detected in February 2016. Using such information provided in real-time, clinicians can alter therapeutic intervention to address the every-changing nature of the patient's tumor profile.

TABLE 13

| Indication | 1st Test | 2nd Test | 3rd Test | 4th Test |
|---|---|---|---|---|
| CRC | Nov. 30, 2015 NRAS (53.5%) PTEN (6.7%) | Dec. 21, 2015 No mut | Feb. 19, 2016 BRAF (1.9%) | |
| GIST | Nov. 2, 2015 Kit (49.8%) | Dec. 8, 2015 No mut | Feb. 5, 2016 No mut | |
| Lung | Nov. 10, 2015 TP53 (92.7%) VHL (4.6%) | Feb. 5, 2016 No mut | | |
| CRC | Dec. 8, 2015 BRAF (3.2%) | Dec. 21, 2015 EGFR (5.6%; 4.6%) SMAD4 (2.3%) | | |
| Lung | Nov. 30, 2015 TP53 (40%; 15.6%) | Dec. 21, 2015 PTEN (19.3%; 6.0%) | Jan. 19, 2016 TP53 (5.2%; 3.3%) EGFR (4.7%) | Feb. 12, 2016 KDR (98.6%) ERBB4 (5.8%) VHL (5.4%) CTNNB1 (3.9%) RB1 (3.7%) TP53 (3.1%; 2.0%) |
| Breast | Nov. 30, 2015 ERBB2 (2.7%) | Dec. 28, 2015 No mut | Jan. 29, 2016 TP53 (8.6%; 3.1%) | |
| Breast | 11-3015 PICK3CA (2.8%) | Dec. 28, 2015 No mut | Jan. 19, 2016 No mut | |
| Pancreatic | Nov. 30, 2015 TP53 (96.9%) CDKN2A (6.4%) SMARCB1 (5.9%) BRAS (5.0%) EGFR (4.8%) VHL (2.4%) IDH1 (2.0%) SMAD4 (2.0%) | Dec. 8, 2015 TP53 (95.2%) | | |

Example 12—Optimization of ISA Enzyme Mixture

As discussed herein, the CGD method may use a variety of enzyme mixtures to efficiently provide an amplifiable cfNA pool from cfDNA present in a sample. The present example illustrates the use of several different enzyme mixtures (1 to 6) on the efficiency of the CGD method (with the efficiency based on yield of the amplified cfDNA in ng/μL). The composition of enzyme mixtures 1 to 6 is provided in Table 14.

The CGD method was performed according to protocol A, with the exceptions noted below. Samples for this example were plasma samples taken from a single subject, with 20 μL of the sample being used for each experiment. Plasma samples were processed to produce the amplifiable cfDNA pool as described in protocol A with the exception that at step 8 of protocol A enzyme mixtures 1 to 6 were substituted for the enzyme mixture recited in protocol A. The amplifiable cfDNA pool was subject to PCR amplification as described in protocol A to produce the analyzable pool of cfDNA. Total yield of amplified DNA was quantified using the Qubit 2.0 Fluorometer together with dsDNA BR and HS assay kits as described above.

The results are shown in Table 14. All enzyme mixtures produced good results. The enzyme mixture of protocol A yielded 82.3 ng/μL of amplified DNA from the original sample cfDNA input. Enzyme mix 1 produced similar yields of amplified DNA (82.2 ng/μL) as compared to protocol A, while enzyme mix 2 and mix 6 produced decreased yields of amplified DNA (70.4 ng/μL and 58.6 ng/μL, respectively) as compared to protocol A (although such mixtures are suitable for use in the methods described herein). Enzyme mix 3, mix 4 and mix 5 produced increased yields of amplified DNA as compared to protocol A (97.1 ng/μL, 105.0 ng/μL and 96.4 ng/μL, respectively).

These results show the CGD method requires a 5'-3' polymerase activity, a 3'-5' exonuclease activity and a DNA ligase activity for efficient production of an amplifiable pool of cfDNA molecules from a cfDNA present in a sample. The addition of polynucleotide kinase activity also increases the efficiency of production of the amplifiable cfDNA pool. As shown in Table 14, addition activities may also be present without significantly inhibiting the efficiency of production of the amplifiable cfDNA pool.

TABLE 14

| Prot A | Enzyme ID | Enzyme Mix 1 | Enzyme Mix 2 | Enzyme Mix 3 | Enzyme Mix 4 | Enzyme Mix 5 | Enzyme Mix 6 |
|---|---|---|---|---|---|---|---|
| — | T4 DNA polymerase | 5 Units (1.75 μL) | 5 Units (1.75 μL) | 5 Units (1.75 μL) | 5 Units (1.75 μL) | 5 Units (1.75 μL) | 5 Units (1.75 μL) |
| — | T4 DNA ligase | 800 Units (2.5 μL) | 2.5 μL | 2.5 μL | 2.5 μL | 2.5 μL | 2.5 μL |
| 5 Units (2.5 μL) | Klenow fragment | 12.5 Units (2.5 μL) | 12.5 Units (2.5 μL) | 12.5 Units (2.5 μL) | 12.5 Units (2.5 μL) | 12.5 Units (2.5 μL) | — |
| 100 Units (2.5 μL) | T4 polynucleotide kinase | 12.5 Units (2.5 μL) | 12.5 Units (2.5 μL) | 12.5 Units (2.5 μL) | 12.5 Units (2.5 μL) | — | — |
| 1 Unit (0.75 μL) | Uracil-DNA glycosylase | 3.75 Units (0.75 μL) | 3.75 Units (0.75 μL) | 3.75 Units (0.75 μL) | — | — | — |
| — | Nb.BbvCI | 12.5 Units (1.25 μL) | 12.5 Units (1.25 μL) | — | — | — | — |
| — | E. coli Single-stranded Binding Protein | 120 ng (0.25 μL) | — | — | — | — | — |
| — | Water | — | (0.25 μL) | (1.5 μL) | (2.25 μL) | (4.75 μL) | (7.25 μL) |
| | Total Volume | 11.5 μL | 11.5 μL | 11.5 μL | 11.5 μL | 11.5 μL | 11.5 μL |
| 82.3 | Yield (ng/μL) | 82.2 | 70.4 | 97.1 | 105 | 96.4 | 58.6 |

Example 13—Optimization of ISA Buffer Solutions

As discussed herein, the CGD method may use a variety of enzyme mixtures to efficiently provide an analyzable cfNA pool from cfDNA present in a sample. The present example illustrates the use of several different enzyme mixtures on the efficiency of the methods of the present disclosure (with the efficiency based on yield of amplified cfDNA in ng/μL).

In this example, the master mix and universal buffers used in protocol A were replaced with either CG1 buffer or CG2 buffer in the combinations shown in Table 6 and the effect on the total yield of amplified cfDNA was determined. CG1 and CG2 when used as a replacement for master mix and/or universal buffer were added in the same volume as the component replaced as per protocol A.

Master mix (also referred to as L Buffer) was added to provide a final concentration in the reaction of: 40 μM dNTP and 2 μM adaptor molecule of SEQ ID NOS: 1 and 2.

Universal buffer (also referred to as S Buffer) was added to provide a final concentration in the reaction of: 50 mM NaCl, 25 mM Tris-Cl (pH 7-8), 10 mM $Mg_2Cl$, 2.5 mM DTT and 1 mM ATP.

CG1 buffer was added to provide a final concentration in the reaction of: 50 mM potassium acetate, 20 mM tris-acetate, pH 7.9, 10 mM magnesium acetate, 1 mM DTT, 1 mM ATP, 40 μM dNTP and 200 μg/ml BSA.

CG2 buffer was added to provide a final concentration in the reaction of: 2 μM adaptor molecule of SEQ ID NO: 5 (in nuclease free water).

The CGD method was performed according to protocol A, with the exceptions noted below. Samples for this example were plasma samples taken from a single subject, with 20 μL of the sample being used for each experiment. Plasma samples were processed to produce the amplifiable cfDNA pool as described in protocol A with the exception that at step 5 of protocol A CG1 and/or CG2 buffers were substituted for the master mix and/or universal buffer recited in protocol A. The amplifiable cfDNA pool was subject to PCR amplification as described in protocol A to produce the analyzable pool of cfDNA with the exception that when the adaptor molecule of SEQ ID NO: 5 was used in CG2 buffer, the primer 5'-ACTCACTATAGACCCTCAGCACCAC-3' (SEQ ID NO: 6) was used rather than the primer specified in protocol A. The enzyme mixture specified in protocol A was used in all reactions.

Total yield of amplified DNA was quantified using the Qubit 2.0 Fluorometer together with dsDNA BR and HS assay kits as described above.

The final concentration of the components of each reaction are provided below, with the results shown in Table 6.

Test 1
50 mM potassium acetate, 20 mM Tris-acetate (pH 7.9), 10 mM magnesium acetate, 1 mM DTT, 1 mM ATP, 40 μM dNTP, 200 ug/ml BSA from CG1 and 50 mM NaCl, 25 mM Tris-Cl (pH 7-8), 10 mM $Mg_2Cl$, 2.5 mM DTT and 1 mM ATP from S buffer Test 2
2 μM adaptor from CG2 and 50 mM NaCl, 25 mM Tris-Cl (pH 7-8), 10 mM $Mg_2Cl$, 2.5 mM DTT and 1 mM ATP from S buffer Test 3
50 mM potassium acetate, 20 mM Tris-acetate (pH 7.9), 10 mM magnesium acetate, 1 mM DTT, 1 mM ATP, 40 μM dNTP, 200 ug/ml BSA from CG1 and 40 μM dNTP and 2 μM adaptor from L Buffer Test 4
40 μM dNTP from L Buffer and 2 μM adaptor from CG2; note the adaptor molecules from the master mix were omitted in this test as they are provided Test 5
50 mM potassium acetate, 20 mM Tris-acetate (pH 7.9), 10 mM magnesium acetate, 1 mM DTT, 1 mM ATP, 40 μM dNTP, 200 ug/ml BSA from CG1 and 2 μM adaptor from CG2

Protocol A
50 mM NaCl, 25 mM Tris-Cl (pH 7-8), 10 mM $Mg_2Cl$, 2.5 mM DTT and 1 mM ATP from S buffer 40 μM dNTP and 2 μM adaptor from L Buffer Test 1 served as a negative control (as neither CG1 nor universal buffer contains the adaptor molecules required to produce the modified cfDNA molecules required for the amplifiable cfDNA pool). Test 2 shows that the presence of dNTP is required for efficient production of modified cfDNA required for the amplifiable cfDNA pool. Test 3 shows that substitution of CG1 buffer for universal buffer improved the total yield of amplified cfDNA as compared to protocol A. Test 4 shows that substitution of CG2 buffer for universal buffer improved the total yield of amplified cfDNA as compared to protocol A. Test 5 also shows that additional buffer components are not required to produce acceptable quantities of amplified cfDNA. Test 5 shows that the substitution of CG1 and CG2 buffers for both the master mix and the universal buffer also improved the total yield of amplified cfDNA.

The results are shown in Table 15. These results show that the methods of the present disclosure can be performed with a variety of buffer compositions, and as shown in Test 4 without the addition of buffer components, to produce an analyzable pool of cfDNA molecules.

TABLE 15

| Prot A | Test 1 | Test 2 | Test 3 | Test 4 | Test 5 |
|---|---|---|---|---|---|
| 95° C. 4 min | | | | | |
| Master Mix | CG1 | CG2 | Master Mix | Master Mix | CG1 |
| Universal Buffer | Universal Buffer | Universal Buffer | CG1 | CG2 | CG2 |
| 95° C. 2 min | | | | | |
| Yield (ng/μL) 82.3 | Undetectable | 3.10 | 109 | 127 | 90 |

Example 14—Optimization of ISA Enzyme Mixtures and Buffer Solutions

As shown in Examples 12 and 13, CGD method may use a variety of enzyme mixtures and buffer solutions to efficiently provide an analyzable cfNA pool from cfDNA present in a sample. The present example illustrates the optimization of the enzyme mixtures using CG1 and CG2 buffers on the efficiency of the methods of the present disclosure (with the efficiency based on yield of amplified cfDNA in ng/μL).

In this example, the master mix and universal buffers used in protocol A were replaced with CG1 buffer and CG2 buffer and the enzyme mixtures of Example 12 were tested with this combination. CG1 and CG2 when used as a replacement for master mix and/or universal buffer were added in the same volume as the component replaced as per protocol A.

The CGD method was performed according to protocol A or according to protocol A with the exceptions noted below (for enzyme mix 1 to 4). Samples for this example were plasma samples taken from a single subject, with 20 µL of the sample being used for each experiment. Plasma samples were processed to produce the amplifiable cfDNA pool as described in protocol A with the exception that at step 5 of protocol A CG1 and CG2 buffers were substituted for the master mix and universal buffer recited in protocol A and at step 8 the described enzyme mixtures 1 to 5 were substituted for the enzyme mixture of protocol A. The amplifiable cfDNA pool was subject to PCR amplification as described in protocol A to produce the analyzable pool of cfDNA with the exception that the primer 5'-ACTCACTATA-GACCCTCAGCACCAC-3' (SEQ ID NO: 6) was used rather than the primer specified in protocol A.

Total yield of amplified DNA was quantified using the Qubit 2.0 Fluorometer together with dsDNA BR and HS assay kits as described above.

CG1 buffer was added to provide a final concentration in the reaction of: 50 mM potassium acetate, 20 mM tris-acetate, pH 7.9, 10 mM magnesium acetate, 1 mM DTT, 1 mM ATP, 40 µM dNTP and 200 µg/ml BSA.

CG2 buffer was added to provide a final concentration in the reaction of: 2 µM adaptor molecule of SEQ ID NO: 5 (in nuclease free water).

The results are shown in Table 16. All enzyme mixtures produced good results. In this Example, enzyme mixes 2 and 3 provided 140 ng/µL of amplified cfDNA from the original sample cfDNA input, while enzyme mix 1, mix 4 and mix 5 provided 124 ng/µL, 112 ng/µL and 99.4 ng/µL, respectively, of amplified cfDNA from the original sample cfDNA input. All enzyme mixtures tested were suitable for use in the methods described herein.

These results are consistent with Example 12 and show the CGD method requires a 5'-3' polymerase activity, a 3'-5' exonuclease activity and a DNA ligase activity for efficient production of an analyzable pool of cfDNA molecules from input cfDNA present in a sample. The addition of polynucleotide kinase activity and uracil-DNA glycosylase activity also increases the efficiency of production of the analyzable pool of cfDNA molecules. As shown in Table 16, addition activities may also be present without significantly inhibiting the efficiency of production of the analyzable pool of cfDNA molecules.

TABLE 16

|  | Test 1 | Test 2 | Test 3 | Test 4 | Test 5 |
|---|---|---|---|---|---|
|  | Same CG1 CG2 Same Enzyme mix 1 | Same CG1 CG2 Same Enzyme mix 2 | Same CG1 CG2 Same Enzyme mix 3 | Same CG1 CG2 Same Enzyme mix 4 | Same CG1 CG2 Same Enzyme mix 5 |
| Yield (ng/µL) | 124 | 140 | 140 | 112 | 99.4 |

Example 15—Efficiency of ISA Between cfDNA in Plasma and Purified DNA

The present example illustrates the efficiency of ISA of cfDNA from a plasma sample and purified DNA (with the efficiency based on yield of amplified cfDNA or DNA in ng/4).

In this example, the CGD method was performed according to protocol A, with the exceptions noted below (for enzyme mix 1 to 5). Samples for this example were plasma samples taken from a single subject, with 20 µL of the sample being used for each experiment. Plasma samples were processed to produce the amplifiable cfDNA pool as described in protocol A with the exception that at step 5 of protocol A CG1 and CG2 buffers were substituted for the master mix and universal buffer recited in protocol A and at step 8 the described enzyme mixtures 1 to 5 were substituted for the enzyme mixture of protocol A. The amplifiable cfDNA pool was subject to PCR amplification as described in protocol A to produce the analyzable pool of cfDNA with the exception that the primer 5'-ACTCACTATA-GACCCTCAGCACCAC-3' (SEQ ID NO: 6) was used rather than the primer specified in protocol A. For purified DNA experiments, 10 ng input DNA was used in an equivalent volume of PBS.

Total yield of amplified DNA was quantified using the Qubit 2.0 Fluorometer together with dsDNA BR and HS assay kits as described above and are expressed as ng/µL.

The results are shown in Table 17, reporting yields in ng/µL. All enzyme mixtures produced good results. In this Example, enzyme mix 3, mix 4 and mix 5 produced yields of amplified cfDNA from the original sample cfDNA input equal to or greater than the yields obtained with 10 ng purified DNA. The yield of amplified cfDNA resulting from enzyme mix 1 and mix 2 as well as that of protocol A also showed good results. All enzyme mixtures tested were suitable for use in the methods described herein.

These results are consistent with previous Examples and demonstrate the efficiency of the methods of the present disclosure in amplifying cfDNA from biological samples are high and in the same range as when purified DNA is used as the sample input.

TABLE 17

| Sample Type | Prot A | Enzyme mix 1 | Enzyme mix 2 | Enzyme mix 3 | Enzyme mix 4 | Enzyme mix 5 |
|---|---|---|---|---|---|---|
| DNA (10 ng input) | 67.2 | 89.8 | 85.0 | 78.0 | 71.6 | 72.8 |
| Plasma Pure | 82.3 | 82.2 | 70.4 | 97.1 | 105 | 96.4 |

Example 16—Stability of Reagents Used in ISA

In order to evaluate the potential for preparing kits (such as pre-loaded 96-well plates) containing the reagents required for carrying out the CGD methods, the various buffers and enzyme mixtures required for implementation of the CGD method were pre-loaded into 96 well plates and stored for 5 months at either −20° C. or 4° C. for 5 months. In addition, the effect of storing the master mix and the enzyme components (in universal buffer), either together or separately, in the 96-well plates was also examined. The results for 6 samples using the stored reagents and fresh reagents were compared.

In this example, the CGD method was performed according to protocol A. Samples for this example were plasma samples taken from the subjects. Plasma samples were processed to produce the analyzable pool of cfDNA pool as described in protocol A. The analyzable pool of cfDNA was subject to NGS analysis as described. Total yield of cfDNA was quantified using the Qubit 2.0 Fluorometer as described above.

The results are shown in Table 18 (yields of amplified cfDNA shown in ng/μL). As shown, storage of the reagents required for performing the CGD method at −20° C. or 4° C. did not significantly impact the performance of the CGD method. In addition, the storage of the master mix and enzyme components together (referenced as combined) was somewhat more effective than storing each separately (referenced as separate).

TABLE 18

| Sample ID | Standard prep | Pre-loaded and stored at −20 Combined | Pre-loaded and stored at −20 Separate | Pre-loaded and stored at 4 Combined | Pre-loaded and stored at 4 Separate |
|---|---|---|---|---|---|
| 1 | 73.2 | 86.4 | 72.6 | 93.4 | 64.2 |
| 2 | 70 | 75.6 | 68.6 | 69.6 | 64.6 |
| 3 | 92.4 | 120 | 109 | 118 | 101 |
| 4 | 57 | 61 | 57 | 62.6 | 57.4 |
| 5 | 100 | 84.4 | 65.6 | 72.8 | 60.4 |
| 6 | 90.6 | 72 | 73 | 76.6 | 62 |

In addition, analyzable cfDNA pools prepare by the CGD method using reagents stored at −20° C. and 4° C. were subjected to agarose gel electrophoresis on a 2% gel and visualized using ethidium bromide (FIG. 10). In FIG. 10, lanes 1-10 show the results from 10 samples, with lanes 1-5 showing results from cfDNA being prepare using reagents stored at −20° C. and lanes 6-10 showing results from cfDNA being prepare using reagents stored at 4° C. In all cases, cfDNA showed strong staining intensity and normal size distribution. This results further confirms the stability of the reagents used in performing the CGD method.

These results collectively confirm the stability of the reagents used in performing the CGD method and allow the manufacture of kits for performing the CGD method.

Example 17—Quantification of cfDNA in a Sample

The present example illustrates the quantification of cfDNA concentration in a sample. In this example, the CGD method was performed according to protocol A. Samples for this example were plasma samples taken from the subjects. Plasma samples were processed to produce the analyzable pool of cfDNA as described in protocol A. For preparation of the standard curve using purified DNA, samples of purified DNA at concentrations of 0, 0.001, 0.005, 0.01, 0.025, 0.05, 0.1, 0.25, 0.5, and 1 ng/μL in 10 μL volumes and subject to CGD method as per protocol A. Total yield of amplified cfDNA or purified DNA was quantified using the Qubit 2.0 Fluorometer as described above.

FIG. 11 shows the linearity of the standard curve established using purified DNA at concentrations of 0, 0.001, 0.005, 0.01, 0.025, 0.05, 0.1, 0.25, 0.5, and 1 ng/μL as inputs in the CGD process at 18 cycles of amplification. By determining the yield (in ng/μL) of amplified cfDNA from the original cfDNA sample input, the concentration of cfDNA in the original sample can be determined by reference to the standard curve produced using the purified DNA. Table 20 shows the results of determination of cfDNA concentrations originally present in two clinical samples. cfDNA concentrations (in ng/μL) were determined from the two clinical samples using the CGD method. From the output yield of cfDNA, the original cfDNA concentrations in the sample were determined from the standard curve shown in FIG. 11.

|  | cfDNA Yield (ng/μL) | Original cfDNA concentration in sample (ng/μL) |
|---|---|---|
| Sample 1 | 0.424 | 0.0126 |
| Sample 2 | 0.302 | 0.0083 |

This Example shows the CGD method can be used to determine the original cfDNA concentration in a clinical sample, allowing the cfDNA concentration in a subject to be quickly and accurately determined and allowing diagnostic use of cfDNA concentrations in a variety of clinical settings.

Example 18—Pooling of Multiple Analyzable Pools of cfDNA for Analysis

The present example illustrates the use of pooling multiple analyzable pools of cfDNA molecules prior to analysis. As described above, in certain examples 1 to 10 μL of the analyzable pool of cfDNA (from a total volume of 20 μL; approximately 1-2 ng) is used to create the sequencing libraries for NGS analysis (for example, by Ion Torrent NGS). Such sampling may, in certain cases, lead to variations in uniformity in NGS sequencing applications. In this example, the cfDNA input used to create the sequencing libraries for NGS was increased to around 20 ng of cfDNA from the analyzable pool produced. To accomplish this end, the CGD method as described in protocol A was modified. First, the CGD method was changed to decrease the amplification cycles used to create the analyzable pool of cfDNA molecules from 25 cycle to 18 cycles to reduce the overall yield of cfDNA in the analyzable pool. Second, rather than taking the cfDNA input for analysis from a single analyzable pool of cfDNA, multiple analyzable pools were created from a single sample and combined (i.e., pooled) and the cfDNA input was taken from the combined analyzable pool of cfDNA. As discussed, the amount of cfDNA used in the NGS analysis was increased to around 20 ng. NGS coverage and NGS uniformity were compared using a cfDNA sample drawn from single analyzable pool of cfDNA produced using 25 cycles of amplification for NGS analysis versus using a cfDNA sample drawn from a combined pool of four separate analyzable pools of cfDNA produced using 18 cycles of amplification for NGS analysis.

In this example, the CGD method was performed according to protocol A. Samples for this example were plasma samples taken from the subjects. Plasma samples were processed to produce the analyzable cfDNA pool as described in protocol A. The analyzable pool of cfDNA was subject to NGS analysis as described. For the refined CGD method (designated CGD2), the analyzable pool of cfDNA was produced using 18 cycles of amplification and the cfDNA sample for NGS analysis was drawn from a combined pool of four separate analyzable pools of cfDNA. For clarification, for the comparison CGD method (referred to as CGD1), the analyzable pool of cfDNA was produced using 25 cycles of amplification and the cfDNA sample for NGS analysis was drawn from a single analyzable pool of cfDNA.

The results are shown in Table 20, reporting NGS coverage, NGS uniformity and percentage improvement in NGS Uniformity using combined analyzable pools of cfDNA. As shown below, combining analyzable pools of cfDNA consistently increased NGS uniformity. Furthermore, sample 14 shows the reproducibility of the CGD method, both when single analyzable cfDNA pools and combined analyzable cfDNA pools were analyzed by Ion Torrent NGS.

TABLE 20

| Method | | NGS Coverage | NGS Uniformity | % Uniformity Improvement |
|---|---|---|---|---|
| 1 | CGD1 | 7596 | 53.6 | 23.3 |
|   | CGD2 | 11809 | 66.1 | |
| 2 | CGD1 | 7444 | 30.4 | 113.8 |
|   | CGD2 | 12690 | 65.0 | |
| 3 | CGD1 | 6617 | 7.0 | 157.1 |
|   | CGD2 | 7492 | 18.0 | |
| 4 | CGD1 | 9888 | 4.7 | 87.9 |
|   | CGD2 | 6195 | 9.3 | |
| 5 | CGD1 | 6242 | 6.4 | 243.8 |
|   | CGD2 | 8634 | 22.0 | |
| 6 | CGD1 | 9358 | 11.9 | |
|   | CGD2 | 8958 | 11.9 | 171.1 |
|   |      | 7388 | 17.3 | |
| 7 | CGD1 | 8274 | 7.1 | |
|   | CGD2 | 6685 | 11.6 | 46.5 |
|   |      | 6909 | 9.2 | |
| 8 | CGD1 | 6498 | 9.2 | 184.8 |
|   | CGD2 | 9315 | 26.2 | |
| 9 | CGD1 | 10957 | 4.8 | 177.1 |
|   | CGD2 | 1373 | 13.3 | |
| 10 | CGD1 | 7157 | 5.8 | 108.6 |
|    | CGD2 | 8502 | 12.1 | |
| 11 | CGD1 | 8648 | 8.2 | 168.3 |
|    | CGD2 | 6040 | 22.0 | |
| 12 | CGD1 | 1069 | 4.6 | 234.8 |
|    | CGD2 | 8062 | 15.4 | |
| 13 | CGD1 | 1023 | 9.6 | 47.9 |
|    | CGD2 | 6387 | 14.2 | |
| 14 | CGD1 | 6193 | 61.4 | 16.2 |
|    |      | 10372 | 67.9 | |
|    |      | 9983 | 71.1 | |
|    |      | 10843 | 71.3 | |
|    |      | 8947 | 70.9 | |
|    |      | 9393 | 68.5 | |
|    | CGD2 | 10041 | 78.9 | |
|    |      | 12314 | 80.3 | |

Example 19—ISA of RNA Using the CGD Method

The methods of the present disclosure may also be used for ISA of cfRNA. In methods of ISA of cfRNA, the cfRNA in the sample is converted to double-strand DNA using standard methodology. The double-strand DNA is then treated in the same manner as cfDNA in a sample. An exemplary protocol for using the methods of the present disclosure is provided in the methods section.

In this example, the CGD method was performed according to protocol A. The sample for this example was a plasma samples taken from a single subject. Plasma samples were processed to produce the analyzable cDNA pool as described in protocol A with additional DNase I and reverse transcription steps to convert cfRNA to cDNA. The analyzable pool of cDNA was subject to NGS analysis as described.

FIG. 12 shows an amplification plot illustrating the successful ISA of cDNA produced from cfRNA. NGS sequencing mapped 933,674 reads with 98.91% of the reads on target. The average base coverage depth was 4.072 and the uniformity of base coverage was 59.56%. This example illustrates the successful application of the CGD method to cfRNA.

What is claimed:

1. A method of in situ amplification of a cell-free nucleic acid (cfNA) the method comprising the steps of: a providing a liquid sample containing a plurality of cfNA; b performing at least one processing step on the sample; c subjecting the sample to a sequential heating program and converting at least a portion of the cfNA in the sample to a modified cfNA using an enzyme mixture to add an exogenous nucleic acid sequence to at least one of the 5' or 3' ends of at least a portion of the cfNA in the sample to create an amplifiable cfNA pool, wherein the exogenous nucleic acid sequence contains a primer site capable of binding a primer and the exogenous nucleic acid sequence has a degenerate nucleic acid sequence flanking at least one side of the primer site; and d amplifying the amplifiable cfNA pool to produce an analyzable pool of cfNA wherein the cfNA in the sample is not subject to a nucleic acid purification step.

2. The method of claim 1, wherein the cfNA is selected from the group consisting of: cfDNA and cfRNA.

3. The method of claim 1, wherein the cfNA is cfRNA and the cfRNA is converted to double-strand DNA prior to step (c).

4. The method of claim 1, wherein at least a portion of the cfNA in the sample are ligated together.

5. The method of claim 1, wherein the cfNA in the sample has a fragment size distribution of 50 bp to 2,000 bp, 100 bp to 1,000 bp, 50 bp to 600 bp, 100 bp to 500 bp, 100 bp to 400 bp, 100 bp to 300 bp, 100 bp to 200 bp, 200 bp to 300 bp, 300 bp to 400 bp, 400 bp to 500 bp or 500 bp to 600 bp.

6. The method of claim 1, wherein the method is carried out in a single reaction vessel.

7. The method of claim 1 where the primer site is a universal primer site.

8. The method of claim 1, wherein the exogenous nucleic acid sequence is added to the 5' end of the cfNA, the 3' end of the cfNA or both the 5' end and the 3' end of at least a portion of the cfNA and wherein at least 50%, at least 60%, at least 70% at least 80, at least 90%, at least 95% or at least 99% of the cfNA in the sample are modified to contain the exogenous nucleic acid sequence.

9. The method of claim 1, wherein the enzyme mixture is selected from the group consisting of:
   a. a mixture comprising a DNA polymerase having a 5'-3' polymerase activity with or without a 3'-5' exonuclease activity and a DNA ligase;
   b. a mixture comprising a DNA polymerase having a 5'-3' polymerase activity with or without a 3'-5' exonuclease activity, a DNA ligase and a DNA polynucleotide kinase;
   c. a mixture comprising a DNA polymerase having a 5'-3' polymerase activity with or without a 3'-5' exonuclease activity, a DNA ligase, a DNA polynucleotide kinase and a uracil DNA glycosylase; and
   d. a mixture comprising a DNA polymerase having a 5'-3' polymerase activity with or without a 3'-5' exonuclease activity, a DNA ligase, a DNA polynucleotide kinase, a uracil DNA glycosylase and a single-strand DNA nucleic acid nicking enzyme.

10. The method of claim 1, wherein the enzyme mixture is selected from the group consisting of:
   a. a mixture comprising T4 DNA polymerase and T4 DNA ligase;

b. a mixture comprising Klenow fragment of DNA polymerase I and T4 DNA ligase;
c. a mixture comprising T4 DNA polymerase, T4 DNA ligase and Klenow fragment of DNA polymerase I;
d. a mixture comprising T4 DNA polymerase, T4 DNA ligase, Klenow fragment of DNA polymerase I and T4 polynucleotide kinase;
e. a mixture comprising T4 DNA polymerase, T4 DNA ligase, Klenow fragment of DNA polymerase I, T4 polynucleotide kinase and uracil-DNA glycosylase; and
f. a mixture comprising T4 DNA polymerase, T4 DNA ligase, Klenow fragment of DNA polymerase I, T4 polynucleotide kinase, uracil-DNA glycosylase and Nb.BbvC1.

11. The method of claim 1, wherein the exogenous nucleic acid sequence has the sequence of SEQ ID NOS: 1 and 2.

12. The method of claim 1, wherein the exogenous nucleic acid sequence is an oligonucleotide comprising a double-strand inverted repeat and a single-strand loop and wherein at least a portion of the cfNA in the sample is prepared to have a blunt end on the 5' end of the cfNA, the 3' end of the cfNA or both the 5' end and 3' end of the cfNA.

13. The method of claim 12, wherein each strand of the exogenous nucleic acid sequence is ligated to each strand of the cfNA at the 5' end of the cfNA, the 3' end of the cfNA or both the 5' end and the 3' end of the cfNA on at least a portion of the cfNA in the sample.

14. The method of claim 13, wherein the single-stranded loop is cleaved prior to step (d).

15. The method of claim 14, wherein the exogenous nucleic acid sequence has the sequence of SEQ ID NO: 10.

16. The method of claim 13, wherein the enzyme mixture comprises a DNA polymerase having a 5'-3' polymerase activity with or without a 3'-5' exonuclease activity, a DNA ligase, a DNA polynucleotide kinase and a uracil-DNA glycosylase.

17. The method of claim 1, wherein the exogenous nucleic acid sequence is an oligonucleotide comprising a double-strand inverted repeat and a single-strand loop and wherein at least a portion of the cfNA in the sample is prepared to have a tail sequence on at least one of the 3' end on the 5' end of the cfNA.

18. The method of claim 17, wherein each strand of the exogenous nucleic acid sequence is ligated to each strand of the cfNA at the 5' end of the cfNA, the 3' end of the cfNA or both the 5' end and the 3' end of the cfNA on at least a portion of the cfNA in the sample.

19. The method of claim 18, wherein the single-stranded loop is cleaved prior to step (d).

20. The method of claim 19, wherein the exogenous nucleic acid sequence has the sequence of SEQ ID NO: 9 or SEQ ID NO: 7.

21. The method of claim 18, wherein the enzyme mixture comprises a DNA polymerase having a 5'-3' polymerase activity with or without a 3'-5' exonuclease activity, a DNA ligase, a DNA polynucleotide kinase and a uracil-DNA glycosylase.

22. The method of claim 12, wherein one strand of the exogenous nucleic acid sequence is ligated to one strand of the cfNA at the 5' end of the cfNA, the 3' end of the cfNA or both the 5' end and the 3' end of the cfNA on at least a portion of the cfNA in the sample.

23. The method of claim 22, wherein the exogenous nucleic acid sequence has the sequence of SEQ ID NO: 5.

24. The method of claim 22, wherein the enzyme mixture comprises a DNA polymerase having a 5'-3' polymerase activity with or without a 3'-5' exonuclease activity, a DNA ligase, a DNA polynucleotide kinase, a single-strand DNA nucleic acid nicking enzyme and optionally a replication block activating activity.

25. The method of claim 1, wherein the exogenous nucleic acid sequence is an oligonucleotide comprising a double-strand inverted repeat, a single-strand loop and a replication block, wherein at least a portion of the cfNA in the sample is prepared to have a blunt end on the 5' end of the cfNA, the 3' end of the cfNA or both the 5' end and 3' end of the cfNA and wherein the replication block is inactive until acted on by a replication block activating activity.

26. The method of claim 25, wherein one strand of the exogenous nucleic acid sequence is ligated to one strand of the cfNA at the 5' end of the cfNA, the 3' end of the cfNA or both the 5' end and the 3' end of the cfNA on at least a portion of the cfNA in the sample.

27. The method of claim 26, wherein the exogenous nucleic acid sequence has the sequence of SEQ ID NO: 5.

28. The method of claim 26, wherein the enzyme mixture comprises a DNA polymerase having a 5'-3' polymerase activity with or without a 3'-5' exonuclease activity, a DNA ligase, a DNA polynucleotide kinase, a single-strand DNA nucleic acid nicking enzyme and a replication block activating activity.

29. The method of claim 1, wherein the at least one processing step is diluting the liquid sample, heating the liquid sample, fragmenting the cfNA in the liquid sample or a combination of the foregoing.

30. The method of claim 1, wherein the at least one processing step is fragmenting the cfNA in the liquid sample and the cfNA in the liquid sample has a fragment size distribution of 50 bp to 600 bp, 100 bp to 500 bp, 100 bp to 400 bp, 100 bp to 300 bp, 100 bp to 200 bp, 200 bp to 300 bp, 300 bp to 400 bp, 400 bp to 500 bp or 500 bp to 600 bp after the at least one processing step.

31. The method of claim 1, wherein the liquid sample is a serum sample, a plasma sample, a urine sample, a saliva sample or a cerebrospinal fluid sample.

32. The method of claim 1, wherein the volume of the liquid sample is from 10 µL to 50 µL.

33. A method of diagnosing a subject as suffering from or at risk for a disease, the method comprising the steps of:
a. providing an analyzable pool of cfNA produced by the method of claim 1;
b. analyzing the analyzable pool of cfNA to determine a characteristic of a cfNA in the analyzable pool of cfNA molecules that is associated with the disease; and
c. determining that the subject is suffering from or at risk for the disease based on the presence of the characteristic or determining that the subject is not suffering from or at risk for the disease based on the absence of the characteristic.

34. A method of monitoring the treatment of a subject that has been diagnosed with a disease and is undergoing treatment with a therapeutic regimen for the treatment of the disease, the method comprising the steps of:
a. providing an analyzable pool of cfNA from the subject by the method of claim 1;
b. analyzing the analyzable pool of cfNA to determine a characteristic of a cfNA in the analyzable pool of cfNA that is associated with the disease;
c. determining if the determined characteristic is compatible with the therapeutic regimen;
d. altering the therapeutic regimen if the determined characteristic indicates the therapeutic regimen is contraindicated or not recommended or continuing the therapeutic regimen if the determined characteristics indicates the therapeutic regimen continues to be recommended; and e. optionally repeating steps a) to d) at desired time intervals.

35. A method for determining the original concentration of a cell-free nucleic acid (cfNA) in a sample, the method comprising the steps of:

a. providing an amplifiable cfNA pool by the method of claim 1;

b. amplifying the amplifiable cfNA pool to produce an amplified pool of cfNA molecules;

c. determining the concentration of cfNA in the amplified pool of cfNA; and d. comparing the concentration of cfNA determined to a standard curve to determine the original concentration of cfNA in the sample.

* * * * *

SEQUENCE LISTING

```
<160> NUMBER OF SEQ ID NOS: 10

<210> SEQ ID NO 1
<211> LENGTH: 17
<212> TYPE: DNA
<213> ORGANISM: Artificial Sequence
<220> FEATURE:
<223> OTHER INFORMATION: adaptor sequence 1

<400> SEQUENCE: 1
attaaccctc actaaag                                                   17

<210> SEQ ID NO 2
<211> LENGTH: 20
<212> TYPE: DNA
<213> ORGANISM: Artificial Sequence
<220> FEATURE:
<223> OTHER INFORMATION: Adaptor sequence 2

<400> SEQUENCE: 2
taatacgact cactataggg                                                20

<210> SEQ ID NO 3
<211> LENGTH: 17
<212> TYPE: DNA
<213> ORGANISM: Artificial Sequence
<220> FEATURE:
<223> OTHER INFORMATION: artificial primer 1

<400> SEQUENCE: 3
attaaccctc actaaag                                                   17
```

```
<210> SEQ ID NO 4
<211> LENGTH: 20
<212> TYPE: DNA
<213> ORGANISM: Artificial Sequence
<220> FEATURE:
<223> OTHER INFORMATION: Artificial Primer 2

<400> SEQUENCE: 4
taatacgact cactataggg                                                  20

<210> SEQ ID NO 5
<211> LENGTH: 67
<212> TYPE: DNA
<213> ORGANISM: artificial sequence
<220> FEATURE:
<223> OTHER INFORMATION: adaptor
<220> FEATURE:
<221> NAME/KEY: modified_base
<222> LOCATION: (1)..(1)
<223> OTHER INFORMATION: thymine at 5' end of sequence contains a free
      OH rather than free phoshate
<220> FEATURE:
<221> NAME/KEY: misc_feature
<222> LOCATION: (15)..(19)
<223> OTHER INFORMATION: n is uridine for each occurrence

<400> SEQUENCE: 5
tgtgttgggt gtggnnnnna tttaatacga ctcactatag accctcagca ccaccacacc      60
caacaca                                                                67

<210> SEQ ID NO 6
<211> LENGTH: 25
<212> TYPE: DNA
<213> ORGANISM: Artificial Sequence
<220> FEATURE:
<223> OTHER INFORMATION: primer

<400> SEQUENCE: 6
actcactata gaccctcagc accac                                            25

<210> SEQ ID NO 7
<211> LENGTH: 68
<212> TYPE: DNA
<213> ORGANISM: Artificial Sequence
<220> FEATURE:
<223> OTHER INFORMATION: Adaptor 4
<220> FEATURE:
<221> NAME/KEY: misc_feature
<222> LOCATION: (15)..(19)
<223> OTHER INFORMATION: n is uridine for each occurence
<220> FEATURE:
<221> NAME/KEY: misc_feature
<222> LOCATION: (68)..(68)
<223> OTHER INFORMATION: n can be any nucleotide and may be absent, but
      if present, n may be repeated up to 9 times

<400> SEQUENCE: 7
tgtgttgggt gtggnnnnna tttaatacga ctcactatag accctcagca ccaccacacc      60 caacacan                                                               68

<210> SEQ ID NO 8
<211> LENGTH: 25
<212> TYPE: DNA
<213> ORGANISM: Artificial Sequence
<220> FEATURE:
<223> OTHER INFORMATION: Artificial primer 4

<400> SEQUENCE: 8
```

```
tgagtgatat ctgggagtcg aggtg                                              25

<210> SEQ ID NO 9
<211> LENGTH: 68
<212> TYPE: DNA
<213> ORGANISM: Artificial Sequence
<220> FEATURE:
<223> OTHER INFORMATION: Adaptor 5
<220> FEATURE:
<221> NAME/KEY: misc_feature
<222> LOCATION: (15)..(19)
<223> OTHER INFORMATION: n is uridine for each occurence

<400> SEQUENCE: 9
tgtgttgggt gtggnnnnna tttaatacga ctcactatag accctcagca ccaccacacc        60
caacacaa                                                                 68

<210> SEQ ID NO 10
<211> LENGTH: 62
<212> TYPE: DNA
<213> ORGANISM: Artificial Sequence
<220> FEATURE:
<223> OTHER INFORMATION: Adaptor 6
<220> FEATURE:
<221> NAME/KEY: misc_feature
<222> LOCATION: (15)..(19)
<223> OTHER INFORMATION: n is uridine for each occurence

<400> SEQUENCE: 10
tgtgttgggt gtggnnnnna tacgactcac tatagaccct cagcaccacc acacccaaca        60
ca                                                                       62
```